United States Patent [19]
Kanda et al.

[11] Patent Number: 6,080,771
[45] Date of Patent: *Jun. 27, 2000

[54] DC107 DERIVATIVES

[75] Inventors: Yutaka Kanda, Tokyo; Hitoshi Arai, Shizuoka; Hiroyuki Yamaguchi, Tokyo; Tadashi Ashizawa, Shizuoka; Shun-ichi Ikeda, Osaka; Chikara Murakata; Tatsuya Tamaoki, both of Shizuoka, all of Japan

[73] Assignee: Kyowa Hakko Kogyo Co., Ltd., Tokyo, Japan

[*] Notice: This patent is subject to a terminal disclaimer.

[21] Appl. No.: 09/133,363

[22] Filed: Aug. 13, 1998

Related U.S. Application Data

[63] Continuation-in-part of application No. PCT/JP97/04584, Dec. 12, 1997.

[30] Foreign Application Priority Data

Dec. 13, 1996 [JP] Japan .................................. 8-334321
Jan. 24, 1997 [JP] Japan .................................. 9-011598

[51] Int. Cl.$^7$ .................... C07D 513/08; C07D 513/18; C07D 519/00; A61K 31/425; A61K 31/70
[52] U.S. Cl. ...................... 514/366; 514/368; 514/369; 540/451; 540/460
[58] Field of Search .................. 540/451, 460; 514/366, 368, 369

[56] References Cited

U.S. PATENT DOCUMENTS 4,999,196 3/1991 Nakano et al. .................... 424/116
5,733,924 3/1998 Kanda et al. .................... 514/431

FOREIGN PATENT DOCUMENTS 786 462 7/1997 European Pat. Off. .

OTHER PUBLICATIONS

Yamada, et al., Heterocycles, vol. 43, No. 2, (1996) 267–270.
Kanda, et al., Bioorganic & Medicinal Chemistry Letters 8, (1998) 909–912.

Primary Examiner—Mukund J. Shah
Assistant Examiner—Bruck Kifle
Attorney, Agent, or Firm—Fitzpatrick, Cella, Harper & Scinto

[57] ABSTRACT

DC107 derivatives represented by formula (I) or pharmaceutically acceptable salts thereof which have antimicrobial activity and antitumor activity are provided:

(I)

wherein $R^1$ represents $CO(CR^{4A}R^{4B})_{n1}(O(CH_2)_{p1})_{n2}OR^5$ {wherein n1 represents an integer of 1 or 2; $R^{4A}$ and $R^{4B}$ are the same or different, and each represents hydrogen or lower alkyl; p1 and n2 each represents an integer of 1 to 10; and $R^5$ represents hydrogen, lower alkyl, or the like), or 8 Claims, No Drawings

DC107 DERIVATIVES

CROSS-REFERENCE TO RELATED APPLICATION

This is a continuation-in-part application of PCT/JP97/04584 filed on Dec. 12, 1997.

BACKGROUND OF THE INVENTION

1. Field of the Invention

The present invention relates to novel DC107 derivatives and pharmaceutically acceptable salts thereof which have antimicrobial activity and antitumor activity.

2. Brief Description of the Background

DC107 (leinamycin), which is disclosed in Japanese Published Unexamined Patent Application No. 112988/89, is a compound produced by microorganisms belonging to the genus Streptomyces. It shows not only antimicrobial activity against various bacteria but also antitumor activity, and has the following structure:

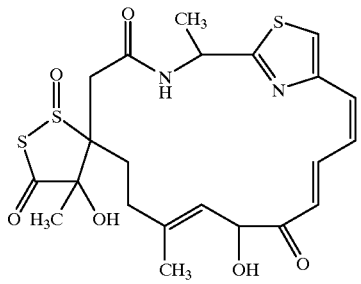

DC107

SUMMARY OF THE INVENTION

An object of the present invention is to provide novel DC107 derivatives and pharmaceutically acceptable salts thereof which have excellent antimicrobial and antitumor activities.

The present invention provides DC107 derivatives represented by formula (I) or pharmaceutically acceptable salts thereof:

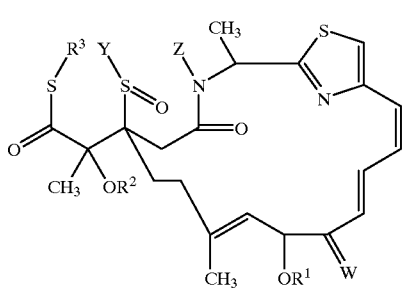

(I)

wherein $R^1$ represents:

CO $(CR^{4A}R^{4B})_{n1}(O(CH_2)_{p1})_{n2}OR^5$ (wherein n1 represents an integer of 1 or 2; $R^{4A}$ and $R^{4B}$ are the same or different, and each represents hydrogen or lower alkyl; p1 represents an integer of 1 to 10; n2 represents an integer of 1 to 10; and $R^5$ represents hydrogen, lower alkyl, —$SiQ^1Q^2Q^3$ (wherein $Q^1$, $Q^2$, and $Q^3$ are the same or different, and each represents lower alkyl or aryl), or CO $(CR^{5A}R^{5B})_{m1}(O(CH_2)_{p2})_{m2}OR^{5C}$ (wherein m1 represents an integer of 1 or 2; $R^{5A}$ and $R^{5B}$ are the same or different, and each represents hydrogen or lower alkyl; p2 represents an integer of 1 to 10; m2 represents an integer of 1 to 10; and $R^{5C}$ represents lower alkyl)}; or

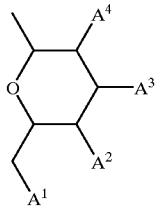

{wherein $A^1$, $A^2$, $A^3$, and $A^4$ are the same or different, and each represents hydrogen, hydroxy, lower alkanoyloxy, substituted or unsubstituted aralkyloxy, or —$OSiA^5A^6A^7$ (wherein $A^5$, $A^6$, and $A^7$ are the same or different, and each represents lower alkyl), or $A^3$ and $A^4$ may be combined with each other to represent a bond};

$R^2$ represents:

hydrogen; or $COR^6$ {wherein $R^6$ represents lower alkyl, aralkyl, substituted or unsubstituted aryl, a substituted or unsubstituted heterocyclic group, or —$(CR^{6A}R^{6B})_{n3}(O(CH_2)_{p3})_{n4}OR^{6C}$ (wherein n3, p3, and n4 have the same meaning as the above n1, p1, and n2, respectively; and $R^{6A}$, $R^{6B}$, and $R^{6C}$ have the same meaning as the above $R^{4A}$, $R^{4B}$, and $R^5$, respectively)}

$R^3$ represents:

lower alkyl;

lower alkenyl;

substituted or unsubstituted aralkyl;

lower alkoxyalkyl;

aralkyloxyalkyl;

substituted or unsubstituted aryloxyalkyl;

lower alkoxycarbonylalkyl;

lower alkanoyloxyalkyl;

alicyclic alkanoyloxyalkyl;

—$CH_2OCOR^7$ (wherein $R^7$ represents $(CH_2)_{n5}R^{7A}$ (wherein n5 represents an integer of 1 to 5; and $R^{7A}$ represents hydroxy, lower alkoxy, substituted or unsubstituted aralkyloxy, lower alkanoyloxy, —$OPO(OH)_2$, —$OSO_3H$, —$OSiR^{7B}_3$ (wherein $R^{7B}$s are the same or different, and each represents lower alkyl or aryl), lower alkanoyl, carboxy, lower alkoxycarbonyl, lower alkoxycarbonylamino, aralkoxycarbonylamino, lower alkoxycarbonyloxy, lower dialkylaminocarbonyloxy, halogen, nitro, maleimido, 2-pyrrolidinon-1-yl, or —$NHCOR^{7C}$ (wherein $R^{7C}$ represents a substituted or unsubstituted lower alkyl, substituted or unsubstituted alicyclic alkyl, substituted or unsubstituted aryl, substituted or unsubstituted aralkyl, a substituted or unsubstituted heterocyclic group,

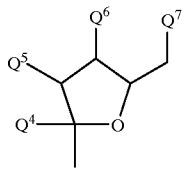

{wherein $Q^4$ to $Q^7$ are the same or different, and each represents hydrogen, hydroxy, lower alkanoyloxy, or —OSiQ$^8_3$ (wherein $Q^8$ has the same meaning as $R^{7B}$), or $Q^4$ and $Q^5$, or $Q^6$ and $Q^7$ are combined with each other to represent —OC(CH$_3$)$_2$O—}, or

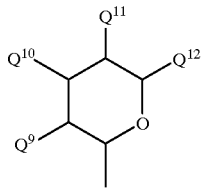

(wherein $Q^9$ to $Q^{12}$ have the same meaning as $Q^4$ to $Q^7$, respectively))), —C(CH$_3$)$_2$R$^{7D}$ {wherein R$^{7D}$ represents lower alkoxycarbonylamino, aralkyloxycarbonylamino, or —NHCOR$^{7E}$ (wherein R$^{7E}$ has the same meaning as R$^{7C}$)}, —(CH$_2$)$_{n6}$CHR$^{7F}$R$^{7G}$ (wherein n6 represents an integer of 0 to 3; R$^{7F}$ represents lower alkanoyl, carboxy, lower alkoxycarbonyl, substituted or unsubstituted aryl, substituted or unsubstituted lower alkyl, or substituted or unsubstituted aralkyl; and R$^{7G}$ has the same meaning as R$^{7D}$), alicyclic alkyl having a substituent, substituted or unsubstituted aryl, substituted or unsubstituted aralkyl, or —CH$_2$(OCH$_2$CH$_2$)$_{n7}$OR$^{7H}$ (wherein R$^{7H}$ represents hydrogen, lower alkyl, substituted or unsubstituted aryl, or substituted or unsubstituted aralkyl; and n7 represents an integer of 1 to 10));

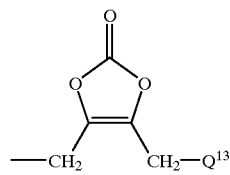

(wherein $Q^{13}$ represents hydrogen, halogen, hydroxy, lower alkoxyalkyl, —OSiR$^{7I}_3$ (wherein R$^{7I}$ has the same meaning as R$^{7B}$), —OCOQ$^{14}$ {wherein Q$^{14}$ represents hydrogen, alkyl, alicyclic alkyl, aralkyl, substituted or unsubstituted aryl, a substituted or unsubstituted heterocyclic group, lower alkoxy, alicyclic alkoxy, 9-fluorenylmethoxy, aralkyloxy, substituted or unsubstituted aryloxy, alkylamino, (hydroxyalkyl) amino, —(CH$_2$)$_{n8}$Q$^{14A}$ (wherein n8 represents an integer of 1 to 3, and Q$^{14A}$ represents carboxy, or lower dialkylamino), CQ$^{14B}_2$NQ$^{14C}$COQ$^{14D}$ (wherein Q$^{14B}$s are the same or different, and each represents hydrogen or lower alkyl, Q$^{14C}$ represents hydrogen or lower alkyl, and Q$^{14D}$ represents lower alkyl, lower alkoxy, aralkoxy, aryl, aryloxy, or 9-fluorenylmethoxy), or —CH$_2$(OCH$_2$CH$_2$)$_{n9}$OCH$_3$ (wherein n9 represents an integer of 1 to 10)}, or

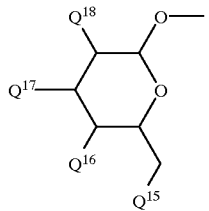

{wherein $Q^{15}$ represents hydrogen, hydroxy, —OSiR$^{7J}_3$ (wherein R$^{7J}$ has the same meaning as R$^{7B}$), or lower alkanoyloxy; and $Q^{16}$ to $Q^{18}$ are the same or different, and each represents hydroxy, —OSiR$^{7J}_3$ (wherein R$^{7J}$ has the same meaning as defined above), or lower alkanoyloxy, and $Q^{17}$ and $Q^{18}$ may be combined with each other to represent a bond});

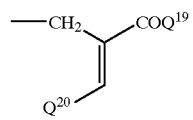

(wherein $Q^{19}$ represents hydroxy, lower alkoxy, or a substituted or unsubstituted heterocyclic group; and $Q^{20}$ represents hydrogen, lower alkyl, or aryl);

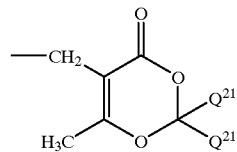

(wherein $Q^{21}$ represents alkyl);

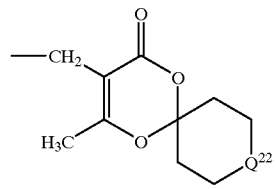

(wherein $Q^{22}$ represents CH$_2$, O, or N—CO$_2$Q$^{23}$ (wherein $Q^{23}$ represents lower alkyl)}; or phthalimidomethyl, or is combined with Y to represent a bond;

Y is combined together with R$^3$ to represent a bond or is combined together with Z to represent a bond;

Z represents a hydrogen atom, or is combined together with Y to represent a bond; and W represents:

oxygen; or

NR$^8$ (wherein R$^8$ represents hydroxy, lower alkoxy, lower alkenyloxy, aralkyloxy, substituted or unsubstituted arylsulfonylamino, or lower alkoxycarbonylamino).

DETAILED DESCRIPTION OF THE INVENTION

This application is based on Japanese applications No. 8-334321 filed on Dec. 13, 1996 and No. 9-11598 filed on Jan. 24, 1997, and PCT/JP97/04584 filed on Dec. 12, 1997, the entire contents of which are incorporated hereinto by reference.

Hereinafter, the compound represented by formula (I) will be called Compound (I). Compounds of other formula numbers with also be called in the same manner.

In the definitions of each group in formula (I), examples of the alkyl include linear or branched alkyl groups having 1 to 20 carbon atoms. Specific examples include methyl, ethyl, propyl, isopropyl, butyl, isobutyl, sec-butyl, tert-butyl, pentyl, isopentyl, hexyl, heptyl, octyl, nonyl, decyl, undecyl, dodecyl, pentadecyl, and the like. The alkyl moieties in the lower alkoxyalkyl, aralkyloxyalkyl, aryloxyalkyl, lower alkoxycarbonylalkyl, lower alkanoyloxyalkyl, alicyclic alkanoyloxyalkyl, alkylamino, and hydroxyalkylamino have the same meaning as the alkyl described above. Examples of the alicyclic alkyl include those having 3 to 8 carbon atoms. Specific examples include cyclopropyl, cyclobutyl, cyclopentyl, cyclohexyl, cycloheptyl, cyclooctyl, and the like. The alicyclic alkyl moiety in the alicyclic alkoxy and alicyclic alkanoylalkyl has the same meaning as the alicyclic alkyl described above.

The lower alkyl represents the above-described alkyls having 1 to 8 carbon atoms. The lower alkyl moieties in the lower alkoxy, lower alkyloxyalkyl, lower alkanoyl, lower alkanoyloxy, lower alkanoyloxyalkyl, lower alkoxycarbonyl, lower alkoxycarbonylalkyl, lower alkoxycarbonylamino, lower alkoxycarbonyloxy, lower dialkylamino, and lower dialkylaminocarbonyloxy have the same meaning as the lower alkyl described above.

Examples of the lower alkenyl moiety in the lower alkenyloxy include linear or branched alkenyls having 2 to 6 carbon atoms. Specific examples include vinyl, allyl, crotyl, prenyl, and the like.

Examples of the aralkyl moieties in the aralkyl, aralkyloxy, aralkyloxyalkyl, and aralkyloxycarbonylamino include those having 7 to 15 carbon atoms. Specific examples include benzyl, phenethyl, benzhydryl, naphthylmethyl, and the like.

Examples of the aryl moieties in the aryl, aryloxy, aryloxyalkyl and arylsulfonylamino include phenyl and naphthyl, and the like. The heterocyclic group is a fused or nonfused 3- to 8-membered heterocyclic group containing at least one hetero atom. Specific examples of the hetero atom include oxygen, sulfur, nitrogen, and the like. Specific examples of the heterocyclic group include 5- or 6-membered monocyclic nitrogen-containing aromatic heterocyclic groups and bicyclic nitrogen-containing aromatic heterocyclic groups in which 5-membered and 6-membered or two 6-membered rings are fused (for example, imidazolyl, pyridyl, indolyl, quinolyl, isoquinolyl, quinoxalinyl, quinazolinyl, and the like), and 5- or 6-membered nitrogen-containing alicyclic heterocyclic groups (for example, pyrrolidinyl, oxopyrrolidinyl, piperidyl, piperidino, piperazinyl, morpholino, thiomorpholino, homopiperidyl, homopiperazinyl, tetrahydropyridyl, and the like). Furthermore, 1,3-dioxolan-4-yl, 1,3-dioxan-4-yl, 1,3-dioxan-5-yl, and the like are preferred oxygen-containing alicyclic heterocyclic groups.

Examples of the substituent on the lower alkyl, alicyclic alkyl, aralkyl, aralkyloxy, aryl, aryloxy, aryloxyalkyl, arylsulfonylamino, or heterocycle include 1 to 3 substituents, which are the same or different, such as halogen, nitro, hydroxy, lower alkanoyl, lower alkanoyloxy, lower alkyl, lower alkoxy, aroyl, aroyloxy, lower alkoxycarbonyl, lower alkoxycarbonylamino, lower alkoxycarbonyloxy, lower dialkylcarbamoyloxy, lower alkoxyaralkyloxycarbonyl, —OPO(OH)$_2$, —OSO$_3$H, —OSiR$^{7B}_3$, carboxy, and the like. The halogen represents fluorine, chlorine, bromine, or iodine. The lower alkanoyl, lower alkanoyloxy, lower alkyl, lower alkoxy, lower alkoxycarbonyl, lower alkoxycarbonylamino, lower alkoxycarbonyloxy, and R$^{7B}$ have the same meaning as defined above, respectively. The aryl moieties in the aroyl and aroyloxy and the lower alkyl moiety in the lower dialkylcarbamoyloxy have the same meaning as defined above. The lower alkyl moiety and aralkyl moiety in the lower alkoxyaralkyloxycarbonyl have the same meaning as defined above.

Preferred examples of compounds (I) include DC107 derivatives according to claim 1 wherein R$^3$ is combined together with Y to represent a bond; and Z is hydrogen. Also preferred are DC107 derivatives according to claim 1 wherein Y is combined together with Z to represent a bond. Among these, more preferred are DC107 derivatives in which R$^1$ is CO(CR$^{4A}$R$^{4B}$)$_{n1}$(O(CH$_2$)$_{p1}$)$_{n2}$OR$^5$ (wherein n1, R$^{4A}$, R$^{4B}$, p1, n2, and R$^5$ have the same meanings as defined above). Among these, most preferred are DC107 derivatives in which n2 is 2 or 5.

Pharmaceutically acceptable salts of compounds (I) include pharmaceutically acceptable acid addition salts, metal salts, ammonium salts, organic-amine addition salts, and amino-acid addition salts. Examples of the acid addition salts include inorganic acid salts (for example, hydrochlorides,, hydrobromides, sulfates, phosphates, and the like), and organic acid salts (for example, formates, acetates, benzoates, maleates, fumarates, succinates, tartarates, citrates, oxalates, methanesulfonates, p-toluenesulfonates, and the like). Examples of the metal salts include alkali metal salts (for example, lithium salts, sodium salts, potassium salts, and the like), alkaline earth metal salts (for example, magnesium salts, calcium salts, and the like), aluminum salts, zinc salts, and the like. Examples of the ammonium salts include ammonium salts, tetramethylammonium salts, and the like. Examples of the organic-amine addition salts include addition salts with morpholine, piperidine, and the like. Examples of the amino-acid addition salts include addition salts with glycine, phenylalanine, asparagine, glutamic acid, lysine, and the like.

Processes for producing compounds (I) are described below.

In the processes shown below, if a group defined changes under the conditions used in a process employed or is unsuitable for carrying out the process, the group can be subjected to a method ordinarily used in organic synthesis chemistry, for example, protection of a functional group, leaving of a protecting group, or a method such as oxidation, reduction, hydrolysis, or the like, whereby the process can be easily carried out.

PROCESS 1

Among compounds (I), those in which R$^1$ is CO(CR$^{4A}$R$^{4B}$)$_{n1}$(O(CH$_2$)$_{p1}$)$_{n2}$OR$^{5a}$ {wherein n1, R$^{4A}$, R$^{4B}$, p1, and n2 have the same meaning as defined above; and R$^{5a}$ represents lower alkyl or —SiQ$^1$Q$^2$Q$^3$ (wherein Q$^1$, Q$^2$, and Q$^3$ have the same meaning as defined above)}, R$^2$ is hydrogen; R$^3$ is combined together with Y to represent a bond, Z represents hydrogen, and W is oxygen are referred to as compounds (Ia); those in which R$^1$ is CO(CR$^{4A}$R$^{4B}$)$_{n1}$(O(CH$_2$)$_{p1}$)$_{n2}$OR$^{5a}$ (wherein n1, R$^{4A}$, R$^{4B}$, p1, n2, and R$^{5a}$ have the same meaning as defined above), R$^2$ is hydrogen, $R^3$ is a substituent represented by $R^3$ described above and having no free hydroxy, amino, or carboxy group therein, Y and Z are combined with each other to represent a bond, and W is oxygen are referred to as compounds (Ib); those in which $R^1$ is CO $(CR^{4A}R^{4B})_{n1}(O(CH_2)_{p1})_{n2}OR^{5a}$ (wherein n1, $R^{4A}$, $R^{4B}$, p1, n2, and $R^{5a}$ have the same meaning as defined above), $R^2$ is $COR^{6a}$ {wherein $R^{6a}$ represents lower alkyl, aralkyl, substituted or unsubstituted aryl, a substituted or unsubstituted heterocyclic group, or $—(CR^{4A}R^{4B})_{n1}(O(CH_2)_{p1})_{n2}OR^{5a}$ (wherein n1, $R^{4A}$, $R^{4B}$, oxygen are referred to as compounds (Id). Furthermore, the compounds represented by formula (I) wherein $R^1$ and $R^2$ are hydrogen, $R^3$ is a substituent represented by $R^3$ described above and having no free hydroxy, amino, or carboxy group therein, Y and Z are combined with each other to represent a bond, and W is oxygen are referred to as compounds (IIa). Compounds (Ia), compounds (Ib), compounds (Ic), and compounds (Id) can be produced, for example, through the following synthesis routes using DC107 as a starting material.

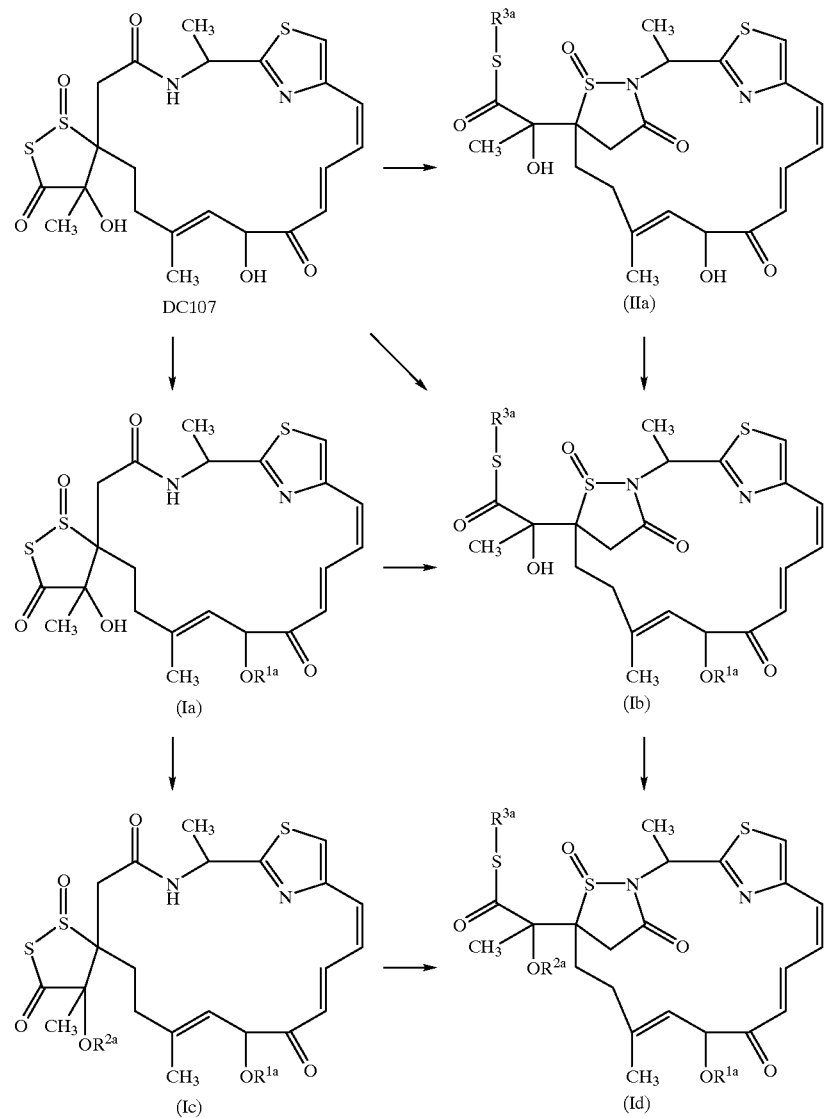

p1, n2, and $R^{5a}$ have the same meaning as defined above)}, $R^3$ is combined together with Y to represent a bond, Z represents hydrogen, and W is oxygen are referred to as compounds (Ic); and those in which $R^1$ is $CO(CR^{4A}R^{4B})_{n1}(O(CH_2)_{p1})_{n2}OR^{5a}$ (wherein n1, $R^{4A}$, $R^{4B}$, p1, n2, and $R^{5a}$ have the same meaning as defined above), $R^2$ is $COR^{6a}$ (wherein $R^{6a}$ has the same meaning as defined above), $R^3$ is a substituent represented by $R^3$ described above and having no free hydroxy, amino, or carboxy group; Y and Z are combined with each other to represent a bond, and W is (In the formulae, $R^{1a}$ represents $CO(CR^{4A}R^{4B})_{n1}(O(CH_2)_{p1})_{n2}OR^{5a}$ {wherein n1, $R^{4A}$, $R^{4B}$, p1, and n2 have the same meaning as defined above; and $R^{5a}$ represents lower alkyl or $—SiQ^1Q^2Q^3$ (wherein $Q^1$, $Q^2$, and $Q^3$ are the same or different, and each represents lower alkyl or aryl)}; $R^{2a}$ represents $COR^{6a}$ (wherein $R^{6a}$ has the same meaning as defined above); and $R^{3a}$ represents a substituent represented by $R^3$ described above and having no free hydroxy, amino, or carboxy group therein.)

Compounds (Ia) and (Ib) can be produced, for example, by the steps shown below based on the above synthesis routes according to the kinds of $R^{1a}$ and $R^{3a}$.

(Step 1)

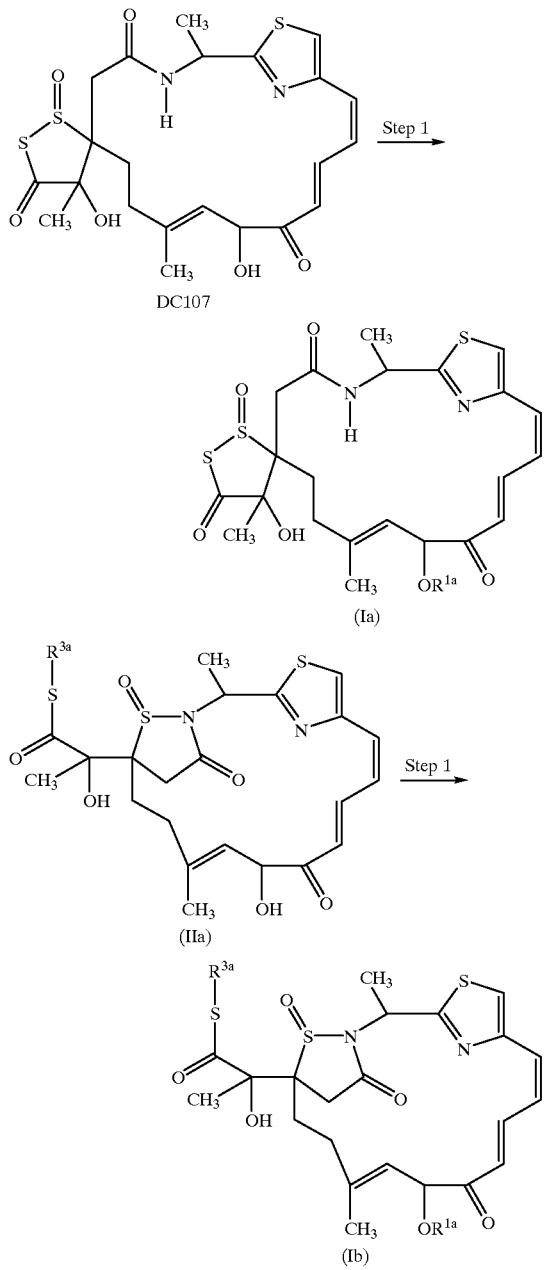

(In the formulae, $R^{1a}$ and $R^{3a}$ have the same meaning as defined above.)

Compound (Ia) or (Ib) can be obtained by reacting DC107 (described in Japanese Published Unexamined Patent Application No. 112988/89) or compound (IIa) {which can be produced from DC107 by the following step 2} with carboxylic acid (III) represented by the following formula:

$$R^{1a}OH \qquad \text{(III)}$$

(wherein $R^{1a}$ has the same meaning as defined above) in the presence of a condensing agent in a solvent inert to the reaction. Any solvent may be used for the reaction so long as it is inert to the reaction. Examples include chloroform, dichloromethane, ether, tetrahydrofuran, acetone, dimethylformamide, acetonitrile, and the like. Especially preferred are chloroform and dichloromethane. Any condensing agent may be used so long as it is used for the ordinary condensation of carboxylic acids with alcohols. For example, dicyclohexylcarbodiimide, 1-ethyl-3-(3-dimethylaminopropyl)carbodiimide hydrochloride, or the like is used. It is possible to accelerate the reaction by further adding dimethylaminopyridine or the like in an amount of 0.1 to 10 equivalents. Compound (III) and the condensing agent are generally used in an amount of 1 to 100 equivalents to DC107 or compound (IIa). The reaction terminates usually in 10 minutes to 24 hours at 0 to 30° C.

Alternatively, compound (Ia) or (Ib) can be obtained by reacting DC107 or compound (IIa) with compound (IV) represented by the following formula:

$$R^{1a}X \qquad \text{(IV)}$$

(wherein $R^{1a}$ has the same meaning as defined above; and X represents chlorine or bromine) or with compound (V) represented by the following formula:

$$R^{1a}_2O \qquad \text{(V)}$$

(wherein $R^{1a}$ has the same meaning as defined above) in the presence of a base. Use of DC107 gives compound (Ia), while use of compound (IIa) gives compound (Ib). Compound (IV) or (V) is used in an amount of generally at least 1 equivalent, preferably 1 to 100 equivalents, to DC107 or compound (IIa).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, diisopropylethylamine. These bases may be used alone or as a mixture thereof. It is possible to accelerate the reaction by further adding dimethylaminopyridine or the like in an amount of 0.1 to 2 equivalents. The base is used in an amount of generally at least 1 equivalent, preferably 1 to 200 equivalents, to DC107 or compound (IIa). The reaction terminates usually in 5 minutes to 24 hours at −20 to 50° C.

(Step 2)

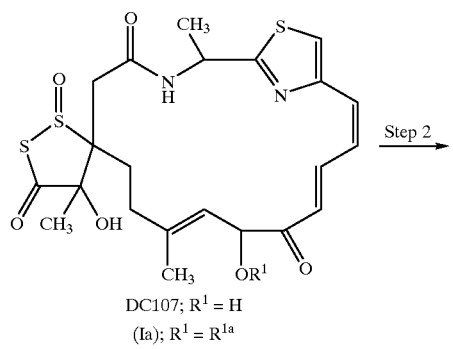

DC107; $R^1$ = H
(Ia); $R^1$ = $R^{1a}$

-continued

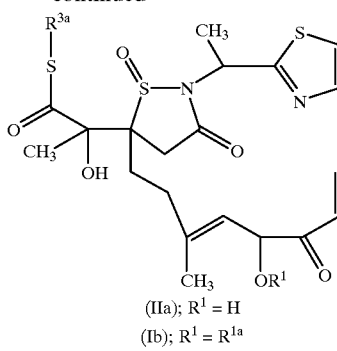

(IIa); $R^1$ = H
(Ib); $R^1$ = $R^{1a}$ (In the formulae, $R^{1a}$ and $R^{3a}$ have the same meaning as defined above.)

Compound (IIa) or (Ib) can be obtained by reacting DC107 or compound (Ia) with compound (VI) represented by the following formula:

$$R^{3a}X \quad (VI)$$

(wherein $R^{3a}$ and X have the same meaning as defined above) in the presence of a base in a solvent inert to the reaction. Use of DC107 gives compound (IIa), while use of compound (Ia) gives compound (Ib).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. The base may be an amine (for example, pyridine, imidazole, triethylamine, diisopropylethylamine, or the like) or a carbonate or bicarbonate of an alkali metal or alkaline earth metal (for example, sodium carbonate, potassium carbonate, calcium carbonate, sodium hydrogen carbonate, or the like). Dimethylaminopyridine or the like can also be used as a catalyst. It is also possible to accelerate the reaction by adding potassium iodide, sodium iodide, tetrabutylammonium iodide, or the like in an amount of 1 to 100 equivalents. Compound (VI) is generally used in an amount of at least 1 equivalent, preferably 1 to 100 equivalents, to DC107 or compound (Ia). The base is generally used in an amount of at least 1 equivalent, preferably 1 to 200 equivalents, to DC107 or compound (Ia). The reaction terminates usually in 10 minutes to 24 hours at 0 to 50° C.

Among compounds (I), those in which $R^2$ is $COR^{6a}$ (wherein $R^{6a}$ has the same meaning as defined above) can be produced by the following steps:

(Step 3-1)

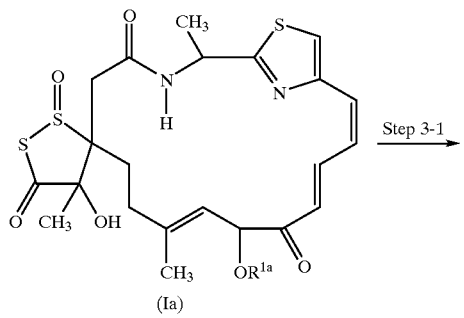

(Ia)

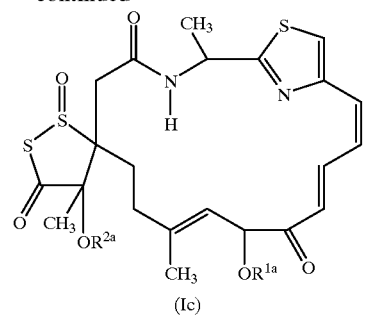

(Ic)

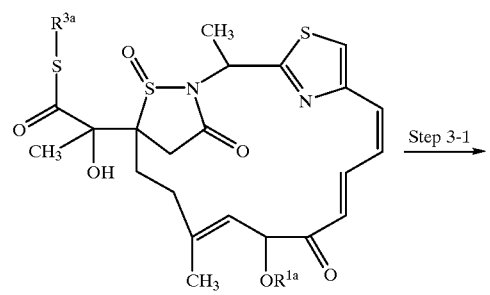

(Ib)

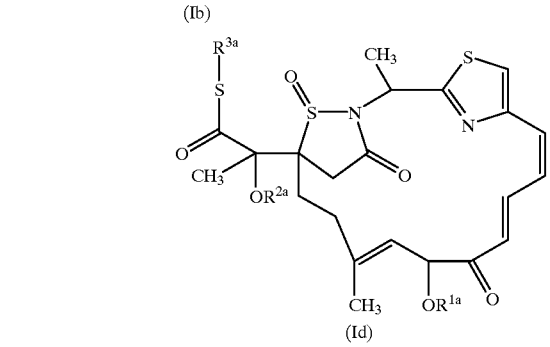

(Id)

(In the formulae, $R^{1a}$, $R^{2a}$, and $R^{3a}$ have the same meaning as defined above.)

Compound (Ic) or (Id) can be obtained by reacting compound (Ia) or (Ib) with compound (VII) represented by the following formula:

$$(R^{6a}CO)_2O \quad (VII)$$

(wherein $R^{6a}$ has the same meaning as defined above) or with compound (VIII) represented by the following formula:

$$R^{6a}COX \quad (VIII)$$

(wherein $R^{6a}$ and X each has the same meaning as defined above) in the presence of a base in a solvent inert to the reaction. Use of compound (Ia) gives compound (Ic), while use of compound (Ib) gives compound (Id). Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, diisopropylethylamine, and the like. These bases may be used alone or as a mixture thereof. Dimethylaminopyridine or the like can be further added in an amount of 0.1 to 10 equivalents.

Compound (VII) or (VIII) is used in an amount of generally at least 1 equivalent, preferably 1 to 100 equivalents, to compound (Ia) or (Ib). The base is generally used in an amount of at least 1 equivalent, preferably 1 to 500 equivalents, to compound (Ia) or (Ib). The reaction terminates usually in 5 minutes to 20 hours at −20 to 50° C.

(Step 3-2)

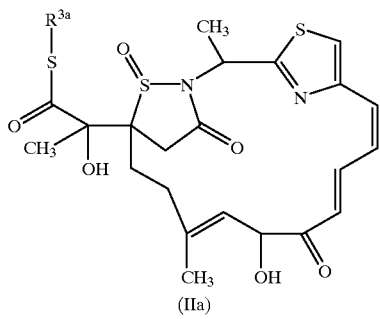
(IIa)

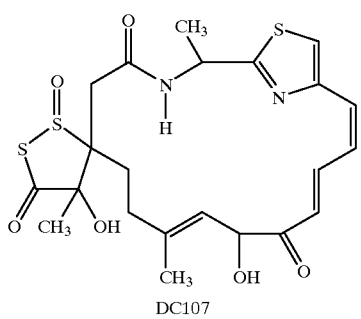
DC107

↓ Step 3-2      ↓ Step 3-2

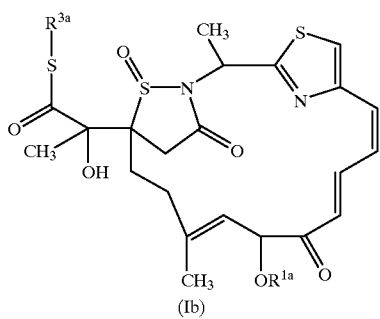
(Ib)

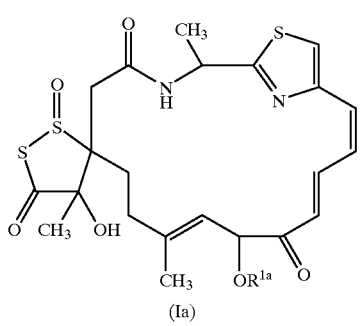
(Ia)

+      +

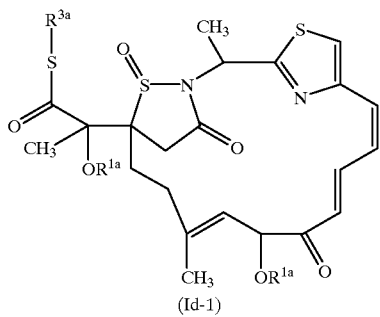
(Id-1)

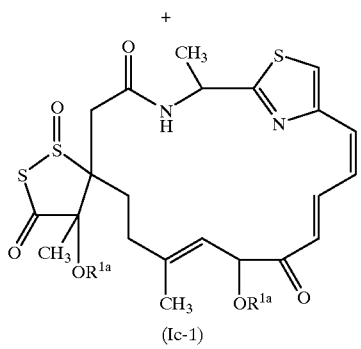
(Ic-1)

(In the formulae, $R^{1a}$ and $R^{3a}$ have the same meaning as defined above.)

If step 3-1 is conducted using DC107 or compound (IIa) as a starting material (step 3-2), compound (Ic-1) or (Id-1) in which $R^2$ and $R^{1a}$ are the same substituent can be obtained together with compound (Ia) or (Ib). In this case, the yields of (Ia) and (Ic-1) or of (Ib) and (Id-1) vary depending on conditions such as the kind and equivalent amount of the compound (IV) or (V), the solvent, and the like.

PROCESS 2

Among compounds (I), compounds (If) and (Ih) in which $R^1$ is $CO(CR^{4A}R^{4B})_{n1}(O(CH_2)_{p1})_{n2}OH$ (wherein n1, $R^{4A}$, $R^{4B}$, p1, and n2 each has the same meaning as defined above) can be produced by the following steps from compounds (Ie) or (Ig) which are compounds (I) in which $R^1$ is $CO(CR^{4A}R^{4B})_{n1}(O(CH_2)_{p1})_{n2}OR^{5b}$ {wherein n1, $R^{4A}$, $R^{4B}$, p1, and n2 have the same meaning as defined above, and $R^{5b}$ represents $-SiQ^1Q^2Q^3$ (wherein $Q^1$, $Q^2$, and $Q^3$ have the same meaning as defined above)}.

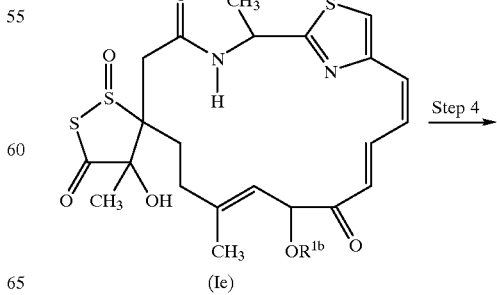
(Ie)

Step 4 →

-continued

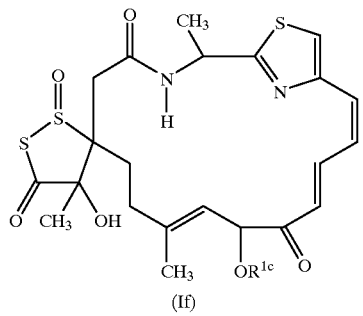
(If)

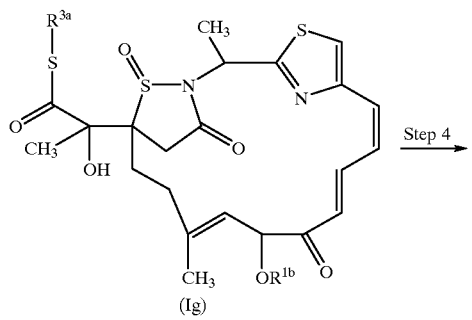
(Ig)

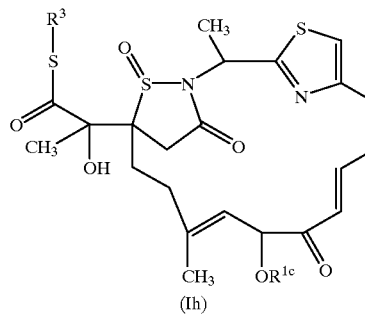
(Ih)

{In the formulae, $R^{3a}$ and $R^3$ have the same meaning as defined above; $R^{1b}$ represents $CO(CR^{4A}R^{4B})_{n1}(O(CH_2)_{p1})_{n2}OR_{5b}$ (wherein n1, $R^{4A}$, $R^{4B}$, p1, and n2 have the same meaning as defined above, and $R^{5b}$ represents $-SiQ^1Q^2Q^3$ (wherein $Q^1$, $Q^2$, and $Q^3$ have the same meaning as defined above)); and $R^{1c}$ represents $CO(CR^{4A}R^{4B})_{n1}(O(CH_2)_{p1})_{n2}OH$ (wherein n1, $R^{4A}$, $R^{4B}$, p1, and n2 have the same meaning as defined above).}

(Step 4)

Compound (If) or (Ih) can be produced by treating compound (Ie) or (Ig) in a solvent (for example, methanol, ethanol, tetrahydrofuran, acetonitrile, or the like) with 0.1 to 100 equivalents of an organic acid (for example, p-toluenesulfonic acid, camphorsulfonic acid, or the like) or an inorganic acid (for example, hydrochloric acid, sulfuric acid, or the like). The reaction terminates usually in 5 minutes to 24 hours at −30 to 30° C. Alternatively, compound (If) or (Ih) can be also synthesized by treating compound (Ie) or (Ig) in a solvent (for example, methanol, ethanol, tetrahydrofuran, acetonitrile, or the like) with 0.1 to 100 equivalents of a fluoride (for example, tetrabutylammonium fluoride, or the like) This reaction terminates usually in 5 minutes to 100 hours at −30 to 50° C. If compound (Ig) in which the substituent $R^{3a}$ has a substituent which is reactive to acids or fluorides (for example, a trialkylsilyl group, or the like) is used, the substituent (for example, a trialkylsilyl group, or the like) on $R^{3a}$ may be converted to a hydroxy group or the like.

PROCESS 3

Among compounds (I), compound (Ii) in which the substituent $R^3$ has a substituent represented by $R^{1a}O-$ can be synthesized by the following steps from compound (IIb) in which the substituent $R^3$ has a substituent readily convertible to a hydroxy group and ordinarily used in organic synthesis chemistry (for example, a trialkylsilyloxy group, an alkanoyloxy group, a lower alkoxyalkoxy group, or the like) via compound (IIc) in which the substituent $R^3$ has a hydroxy group.

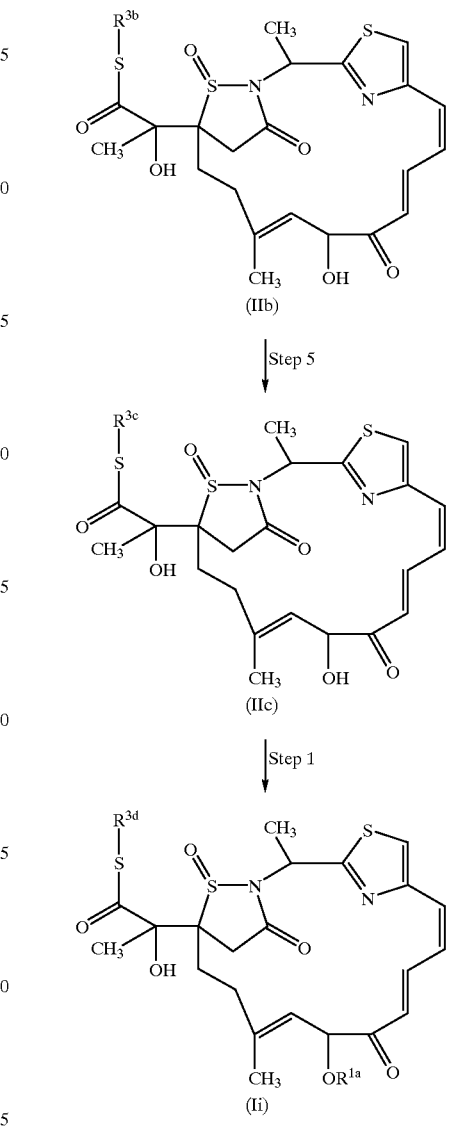

(In the formulae, $R^{1a}$ has the same meaning as defined above; $R^{3b}$ represents a substituent represented by $R^3$ described above and having a substituent readily convertible to a hydroxy group and ordinarily used in organic synthesis chemistry (for example, a trialkylsilyloxy group, an alkanoyloxy group, a lower alkoxyalkoxy group, or the like); $R^{3c}$ represents a substituent represented by $R^3$ described above and having a hydroxy group; and $R^{3d}$ represents a substituent represented by $R^3$ described above and having a substituent represented by $R^{1a}O-$.)

(Step 5)

Compound (IIc) can be synthesized from compound (IIb), in which the substituent $R^{3b}$ has a substituent readily convertible to a hydroxy group and ordinarily used in organic synthesis chemistry, by converting the substituent to a hydroxy group by a method ordinarily used in organic synthesis chemistry. For example, compound (IIb) in which the substituent $R^{3b}$ has a trialkylsilyloxy group is treated in a solvent (for example, water, acetic acid, methanol, ethanol, tetrahydrofuran, acetonitrile, or the like) with 0.1 to 100 equivalents of a fluoride (for example, tetrabutylammonium fluoride, hydrogen fluoride, or the like), whereby compound (IIb) can be converted to compound (IIc) in which the trialkylsilyloxy group has been converted to a hydroxy group. The reaction terminates usually in 5 minutes to 100 hours at −30 to 50° C. It is also possible to convert compound (IIb) to compound (IIc) by treating compound (IIb) in a solvent (for example, water, methanol, ethanol, tetrahydrofuran, acetonitrile, or the like) with 0.1 to 100 equivalents of an organic acid (for example, p-toluenesulfonic acid, camphorsulfonic acid, or the like) or an inorganic acid (for example, hydrochloric acid, sulfuric acid, or the like). This reaction terminates usually in 5 minutes to 24 hours at −30 to 30° C.

Compounds (IIb) in which the substituent $R^{3b}$ has another substituent (for example, an alkanoyloxy group, a lower alkoxyalkoxy group, or the like) can also be converted to compound (IIc), in which $R^{3b}$ has a hydroxy group, by an ordinary method used in organic synthesis chemistry (e.g., acid treatment, base treatment, or the like).

Compound (Ii) can be synthesized from compound (IIc) by the method shown in step 1. Namely, compound (Ii) can be synthesized by reacting compound (IIc) with carboxylic acid (III) represented by the following formula:

$$R^{1a}OH \qquad (III)$$

(wherein $R^{1a}$ has the same meaning as defined above) in the presence of a condensing agent in a solvent inert to the reaction. Any solvent may be used for the reaction so long as it is inert to the reaction. Examples include chloroform, dichloromethane, ether, tetrahydrofuran, acetone, dimethylformamide, acetonitrile, and the like. Especially preferred are chloroform and dichloromethane. Any condensing agent may be used so long as it is used for the ordinary condensation of carboxylic acids with alcohols. For example, dicyclohexylcarbodiimide, 1-ethyl-3-(3-dimethylaminopropyl)carbodiimide hydrochloride, or the like is used. It is possible to accelerate the reaction by further adding dimethylaminopyridine or the like in an amount of 0.1 to 10 equivalents. Compound (III) and the condensing agent are generally used in an amount of 1 to 100 equivalents to compound (IIc). The reaction terminates usually in 10 minutes to 24 hours at 0 to 30° C.

Alternatively, compound (Ii) can be obtained by reacting compound (IIc) with compound (IV) represented by the following formula:

$$R^{1a}X \qquad (IV)$$

(wherein $R^{1a}$ and X have the same meaning as defined above) or with compound (V) represented by the following formula:

$$R^{1a}{}_2O \qquad (V)$$

(wherein $R^{1a}$ has the same meaning as defined above) in the presence of a base. Compound (IV) or (V) is generally used in an amount of at least 1 equivalent, preferably 1 to 100 equivalents, to compound (IIc).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, and diiisopropylethylamine. These bases may be used alone or as a mixture thereof. It is possible to accelerate the reaction by further adding dimethylaminopyridine or the like in an amount of 0.1 to 2 equivalents. The base is generally used in an amount of at least 1 equivalent, preferably 1 to 200 equivalents, to compound (IIc). The reaction terminates usually in 5 minutes to 24 hours at −20 to 50° C.

PROCESS 4

Among compounds (I), those in which W is oxygen are referred to as compounds (Ij), and those in which W is $NR^8$ (wherein $R^8$ has the same meaning as defined above) are referred to as compounds (Ik). Compound (Ik) can be produced from compound (Ij), for example, by the following step.

(Step 6)

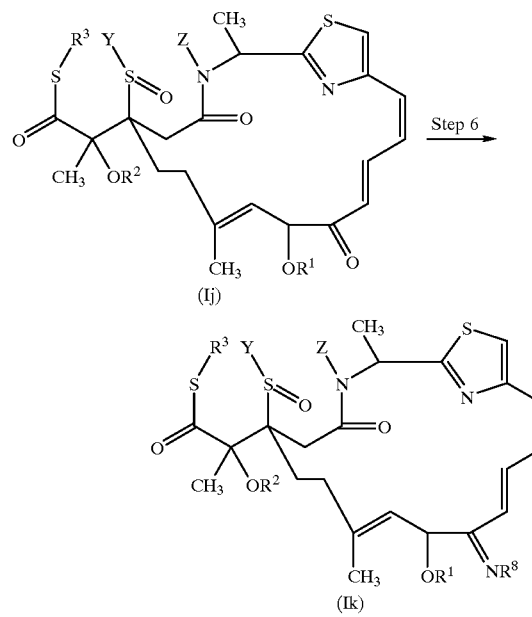

(In the formulae, $R^1$, $R^2$, $R^3$, Y, Z, and R have the same meaning as defined above.)

Compound (Ik) can be obtained by reacting compound (Ij) with compound (IX) represented by the following formula:

$$R^8NH_2 \qquad (IX)$$

(wherein $R^8$ has the same meaning as defined above) or with the hydrochloride thereof in a solvent inert to the reaction.

Examples of the solvent for use in the reaction include methanol, ethanol, dichloromethane, chloroform, tetrahydrofuran, dimethylformamide, acetonitrile, and the like. These may be used alone or as a mixture thereof. This reaction can be accelerated by adding pyridine or an acid. Preferred examples of the acid include organic acids, such as p-toluenesulfonic acid, camphorsulfonic acid, pyridinium p-toluenesulfonate, and the like. Inorganic acids, e.g., hydrochloric acid and sulfuric acid, can also be used.

Compound (IX) is generally used in an amount of 1 to 50 equivalents to compound (Ij). Pyridine or an acid may be used in an amount of 1 to 100 equivalents. The reaction terminates usually in 5 minutes to 24 hours at 0 to 30° C.

PROCESS 5

Among compounds (I), compound (In) in which $R^1$ is $CO(CR^{4A}R^{4B})_{n1}(O(CH_2)_{p1})_{n2}OCO(CR^{5A}R^{5B})_{m1}(O(CH_2)_{p2})_{m2}OR^{5C}$ (wherein n1, $R^{4A}$, $R^{4B}$, p1, n2, m1, $R^{5A}$, $R^{5B}$, p2, m2, and $R^{5C}$ have the same meaning as defined above) can be produced by the following step from compound (Im) which is compound (I) in which $R^1$ is $CO(CR^{4A}R^{4B})_{n1}(O(CH_2)_{p1})_{n2}OH$ (wherein n1, $R^{4A}$, $R^{4B}$, p1, and n2 have the same meaning as defined above).

(Step 7)

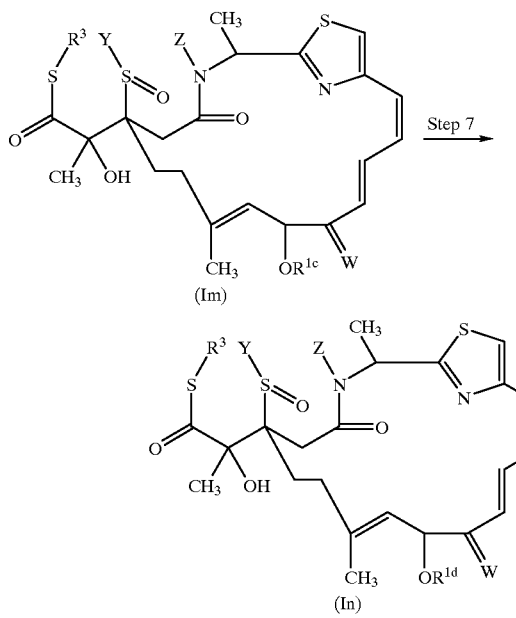

{In the formulae, $R^{1c}$, $R^3$, Y, Z, and W have the same meaning as defined above; and $R^{1d}$ represents $CO(CR^{4A}R^{4B})_{n1}(O(CH_2)_{p1})_{n2}OCO(CR^{5A}R^{5B})_{m1}(O(CH_2)_{p2})_{m2}OR^{5C}$ (wherein n1, $R^{4A}$, $R^{4B}$, p1, n2, m1, $R^{5A}$, $R^{5B}$, p2, m2, and $R^{5C}$ have the same meaning as defined above).}

Compound (In) can be obtained by reacting compound (Im) with carboxylic acid (X) represented by the following formula:

$$HOCO(CR^{5A}R^{5B})_{m1}(O(CH_2)_{p2})_{m2}OR^{5C} \tag{X}$$

(wherein m1, $R^{5A}$, $R^{5B}$, p2, m2, and $R^{5C}$ have the same meaning as defined above) in the presence of a condensing agent in a solvent inert to the reaction. Any solvent may be used for the reaction so long as it is inert to the reaction.

Examples include chloroform, dichloromethane, ether, tetrahydrofuran, acetone, dimethylformamide, acetonitrile, and the like. Especially preferred are chloroform and dichloromethane. Any condensing agent may be used so long as it is used for the ordinary condensation of carboxylic acids with alcohols. For example, dicyclohexylcarbodiimide, 1-ethyl-3-(3-dimethylaminopropyl)carbodiimide hydrochloride, or the like is used. It is possible to accelerate the reaction by further adding dimethylaminopyridine or the like in an amount of 0.1 to 10 equivalents. Compound (X) and the condensing agent are generally used in an amount of 1 to 100 equivalents to compound (Im). The reaction terminates usually in 10 minutes to 24 hours at 0 to 30° C.

Alternatively, compound (In) can be obtained by reacting compound (Im) with compound (XI) represented by the following formula:

$$XCO(CR^{5A}R^{5B})_{m1}(O(CH_2)_{p2})_{m2}OR^{5C} \tag{XI}$$

(wherein m1, $R^{5A}$, $R^{5B}$, p2, m2, $R_{5C}$ and X have the same meaning as defined above) or with compound (XII) represented by the following formula:

$$O(CO(CR^{5A}R^{5B})_{m1}(O(CH_2)_{p2})_{m2}OR^{5C})_2 \tag{XII}$$

(wherein m1, $R^{5A}$, $R^{5B}$, p2, m2, and $R^{5C}$ have the same meaning as defined above) in the presence of a base. Compound (XI) or (XII) is generally used in an amount of at least 1 equivalent, preferably 1 to 100 equivalents, to compound (Im).

Any solvent may be used for the reaction so long as it is inert to the reaction. Examples include chloroform, dichloromethane, ether, tetrahydrofuran, acetone, dimethylformamide, acetonitrile, and the like. These may be used alone or as a mixture thereof. Examples of the base include pyridine, triethylamine, diisopropylethylamine, and the like. These bases may be used alone or as a mixture thereof. It is possible to accelerate the reaction by further adding dimethylaminopyridine or the like in an amount of 0.1 to 2 equivalents. The base is used in an amount of generally at least 1 equivalent, preferably 1 to 200 equivalents, to compound (Im). The reaction terminates usually in 5 minutes to 24 hours at −20 to 50° C.

PROCESS 6

Among compounds (I), compounds (Ip) and (Iq) in which $R^1$ is

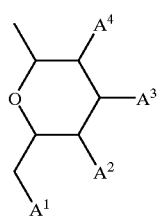

(wherein $A^1$, $A^2$, $A^3$, and $A^4$ have the same meaning as defined above) can be produced from compound (IId) by the following steps.

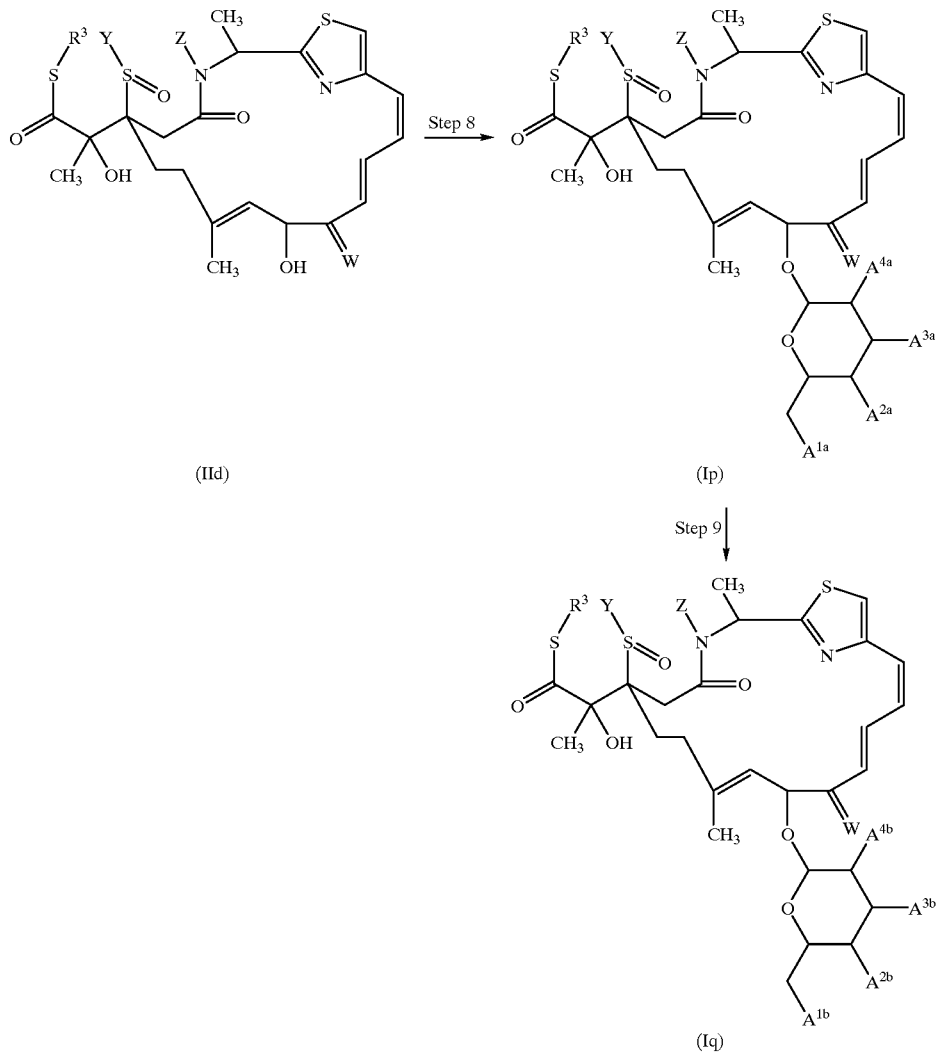

(IId)　　　(Ip)

Step 9 ↓

(Iq)

{In the formulae, $R^3$, Y, Z, and W have the same meaning as defined above; $A^{1a}$, $A^{2a}$, $A^{3a}$, and $A^{4a}$ are the same or different, and each represents hydrogen, lower alkanoyloxy, substituted or unsubstituted aralkyloxy) or $-OSiA^5A^6A^7$ (wherein $A^5$, $A^6$, and $A^7$ have the same meaning as defined above) or $A^{3a}$ and $A^{4a}$ may be combined with each other to represent a bond; and $A^{1b}$, $A^{2b}$, $A^{3b}$, and $A^{4b}$ have the same meaning as $A^1$, $A^2$, $A^3$, and $A^4$ defined above, provided that at least one of $A^{1b}$, $A^{2b}$, $A^{3b}$, and $A^{4b}$ represents a hydroxy group.}

(Step 8)

Compound (Ip) can be produced by reacting compound (IId) with a compound represented by the following formula:

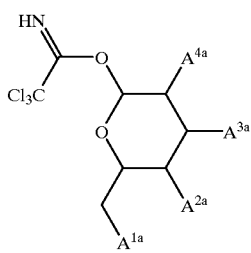

(wherein $A^{1a}$, $A^{2a}$, $A^{3a}$, and $A^{4a}$ have the same meaning as defined above) or

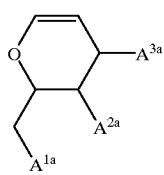

(wherein $A^{1a}$, $A^{2a}$, and $A^{3a}$ have the same meaning as defined above) in an inert solvent in the presence of an acid. The amount of the compound to be reacted with compound (IId) is 1 to 100 equivalents to compound (IId). Any solvent may be used for the reaction so long as it is inert to the reaction. Examples include chloroform, dichloromethane, ether, tetrahydrofuran, toluene, dimethylformamide, acetonitrile, and the like. Especially preferred are chloroform and dichloromethane. Examples of the acid include organic acids (for example, p-toluenesulfonic acid, camphorsulfonic acid, pyridinium p-toluenesulfonate, trifluoroacetic acid, trifluoromethanesulfonic acid, and the like), inorganic acids (for example, hydrochloric acid, sulfuric acid, and the like), and Lewis acids (for example, titanium tetrachloride, boron trifluoride/diethyl ether complex, and the like). The acid is generally used in an amount of 0.1 to 5 equivalents to compound (IId). The reaction terminates usually in 5 minutes to 24 hours at −30 to 100° C.

(Step 9)

Compound (Iq) can be synthesized from compound (Ip) by converting the substituents thereof represented by $A^{1a}$, $A^{2a}$, $A^{3a}$, and $A^{4a}$. For example, compound (Ip) in which the substituent represented by $A^{1a}$, $A^{2a}$, $A^{3a}$, or $A^{4a}$ is —$OSiA^5A^6A^7$ (wherein $A^5$, $A^6$, and $A^7$ have the same meaning as defined above) is treated in a solvent (for example, water, acetic acid, methanol, ethanol, tetrahydrofuran, acetonitrile, or the like) with 0.1 to 100 equivalents of a fluoride (for example, tetrabutylammonium fluoride, hydrogen fluoride, or the like), an organic acid (for example, p-toluenesulfonic acid, camphorsulfonic acid, or the like), or an inorganic acid (for example, hydrochloric acid, sulfuric acid, or the like), whereby compound (Ip) can be converted to compound (Iq) in which the substituent represented by —$OSiA^5A^6A^7$ (wherein $A^5$, $A^6$, and $A^7$ have the same meaning as defined above) has been converted to a hydroxy group. The reaction terminates usually in 5 minutes to 100 hours at −30 to 50° C.

Compounds (Ip) in which the substituent $R^1$ has another substituent (for example, an alkanoyloxy group, an aralkyloxy group, or the like) can be also converted to compound (Iq), in which the substituent $R^1$ has a hydroxy group, by an ordinary method used in organic synthesis chemistry (e.g., acid treatment, base treatment, oxidation reaction, or the like).

For converting a functional group of $R^1$, $R^2$, $R^3$, or W in producing compound (I), known methods (e.g., *Comprehensive Organic Transformations*, R. C. Larock (1989) can be used besides the steps described above.

The target compounds produced by the processes described above can be isolated and purified by purification techniques ordinarily used in organic synthesis chemistry, for example, neutralization, filtration, extraction, washing, drying, concentration, recrystallization, various chromatography, and the like.

Although some of the compounds (I) can exist as stereoisomers, e.g., diastereomers, the present invention includes all possible isomers including these and mixtures thereof.

Furthermore, compounds (I) and pharmaceutically acceptable salts thereof may be present in the form of an adduct with water or any of various solvents. However, these compounds also are included in the present invention.

Specific examples of compounds (I) obtained by the processes described above are shown in Table 1.

TABLE 1

Examples (1) of Compounds (I)

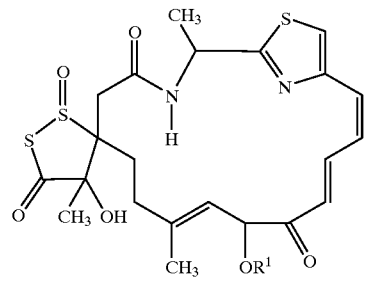

| Compound | $R^1$ |
|---|---|
| 1 | $COCH_2OCH_2CH_2OCH_3$ |
| 2 | $COCH_2(OCH_2CH_2)_2OCH_3$ |
| 3 | $COCH_2(OCH_2CH_2)_3OCH_3$ |
| 4 | $COCH_2(OCH_2CH_2)_4OCH_3$ |
| 5 | $COCH_2(OCH_2CH_2)_5OCH_3$ |
| 6 | $COCH_2(OCH_2CH_2)_6OCH_3$ |
| 7 | $COCH_2(OCH_2CH_2)_2OSi(C_6H_5)_2C(CH_3)_3$ |
| 8 | $COCH_2(OCH_2CH_2)_2OH$ |
| 9 | $COCH(CH_3)(OCH_2CH_2)_2OCH_3$ |
| 10 | $COC(CH_3)_2(OCH_2CH_2)_2OCH_3$ |
| 26 | $COCH_2(OCH_2CH_2)_4OSi(C_6H_5)_2C(CH_3)_3$ |
| 27 | $COCH_2(OCH_2CH_2)_4OH$ |
| 30 | $COCH_2(OCH_2CH_2)_2OCOCH_2(OCH_2CH_2)_2OCH_3$ |
| 31 | $COCH_2(OCH_2CH_2)_2OCOCH_2OCH_2CH_2OCH_3$ |
| 32 | $COCH_2OCH_2CH_2CH_2OSi(C_6H_5)_2C(CH_3)_3$ |
| 33 | $COCH_2OCH_2CH_2CH_2OH$ |
| 34 | $COCH_2OCH_2CH_2CH_2CH_2CH_2OSi(C_6H_5)_2C(CH_3)_3$ |
| 35 | $COCH_2OCH_2CH_2CH_2CH_2CH_2OH$ |
| 36 | $CO(CH_2CH_2O)_3CH_3$ |

TABLE 1-continued

Examples (2) of Compounds (I)

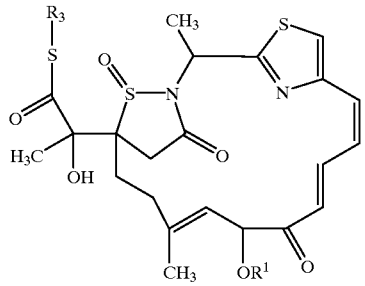

| Compound | R¹ | R³ |
|---|---|---|
| 11 | COCH$_2$(OCH$_2$CH$_2$)OCH$_3$ | DMDO |
| 12 | COCH$_2$(OCH$_2$CH$_2$)$_2$OCH$_3$ | DMDO |
| 13 | COCH$_2$(OCH$_2$CH$_2$)$_3$OCH$_3$ | DMDO |
| 14 | COCH$_2$(OCH$_2$CH$_2$)$_4$OCH$_3$ | DMDO |
| 15 | COCH$_2$(OCH$_2$CH$_2$)$_5$OCH$_3$ | DMDO |
| 16 | COCH$_2$(OCH$_2$CH$_2$)$_2$OSi(C$_6$H$_5$)$_2$C(CH$_3$)$_3$ | DMDO |
| 14 | COCH$_2$(OCH$_2$CH$_2$)$_4$OCH$_3$ | DMDO |
| 15 | COCOH$_2$(OCH$_2$CH$_2$)$_5$OCH$_3$ | DMDO |
| 16 | COCH$_2$(OCH$_2$CH$_2$)$_2$OSi(C$_2$H$_5$)$_2$C(CH$_3$)$_3$ | DMDO |
| 17 | COCH$_2$(OCH$_2$CH$_2$)$_2$OH | DMDO |
| 18 | COCH$_2$OCH$_2$CH$_2$OCH$_3$ | —CH$_2$—[dioxol-2-one]—CH$_2$OCOCH$_2$OCH$_2$CH$_2$OCH$_3$ |
| 19 | COCH$_2$(OCH$_2$CH$_2$)$_2$OCH$_3$ | —CH$_2$—[dioxol-2-one]—CH$_2$OCOCH$_2$(OCH$_2$CH$_2$)$_2$OCH$_3$ |
| 20 | COCH$_2$(OCH$_2$CH$_2$)$_5$OCH$_3$ | —CH$_2$—C(=CH$_2$)—CO$_2$Me |
| 21 | COCH$_2$(OCH$_2$CH$_2$)$_5$OCH$_3$ | —CH$_2$—[2,2-dimethyl-4H-1,3-dioxin-4-one ring] |
| 22 | COCH$_2$(OCH$_2$CH$_2$)$_2$OCH$_3$ | —CH$_2$OCO—CH$_2$—NHCO$_2$C(CH$_3$)$_3$ |
| 23 | COCH$_2$(OCH$_2$CH$_2$)$_2$OCH$_3$ | —CH$_2$OCO—CH$_2$CH$_2$—CH(NHCO$_2$C(CH$_3$)$_3$)—CO$_2$C(CH$_3$)$_3$ |
| 24 | COCH$_2$(OCH$_2$CH$_2$)$_5$OCH$_3$ | —CH$_2$OCO—CH$_2$—NHCO$_2$C(CH$_3$)$_3$ |

TABLE 1-continued
| 25 | COCH$_2$(OCH$_2$CH$_2$)$_5$OCH$_3$ | 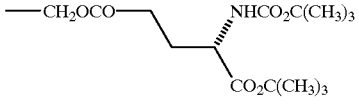 |
DMDO = 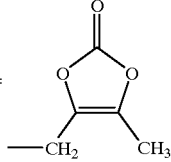
Examples (3) or Compounds (I)
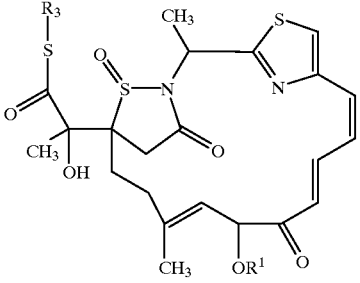
| Compound | R$^1$ | R$^3$ |
|---|---|---|
| 28 | COCH$_2$(OCH$_2$CH$_2$)$_2$OCH$_3$ | 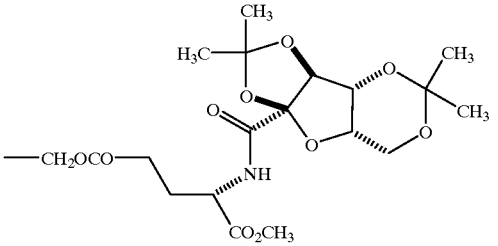 |
| 29 | COCH$_2$(OCH$_2$CH$_2$)$_2$OCH$_3$ | 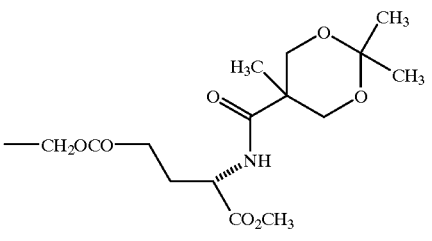 |
| 37 | COCH$_2$(OCH$_2$CH$_2$)$_4$OSi(C$_6$H$_5$)$_2$C(CH$_3$)$_3$ | DMDO |
| 38 | COCH$_2$(OCH$_2$CH$_2$)$_4$OH | DMDO |
| 39 | COCH$_2$(OCH$_2$CH$_2$)$_4$OCOCH$_2$(OCH$_2$CH$_2$)$_2$OCH$_3$ | DMDO |

TABLE 1-continued
| | | |
|---|---|---|
| 40 | COCH₂(OCH₂CH₂)₂OCH₃ | 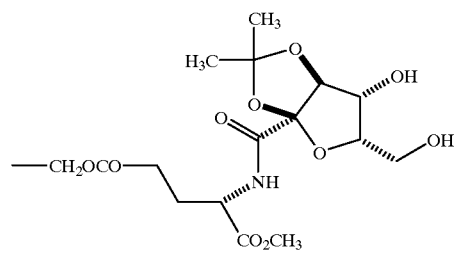 |
| 41 | COCH₂(OCH₂CH₂)₂OCH₃ | 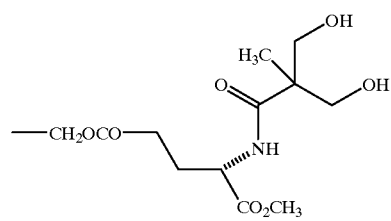 |
| 42 | COCH₂(OCH₂CH₂)₂OCH₃ | 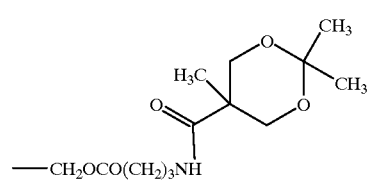 |
| 43 | COCH₂(OCH₂CH₂)₂OCH₃ | 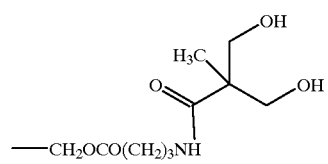 |
| 44 | COCH₂(OCH₂CH₂)₂OCH₃ | 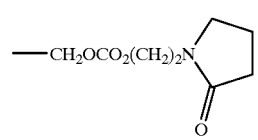 |
| 45 | COCH₂(OCH₂CH₂)₂OCH₃ | CH₂OCO(OCH₂CH₂)₂OCH₃ |
| 46 | COCH₂(OCH₂CH₂)₂OCH₃ | 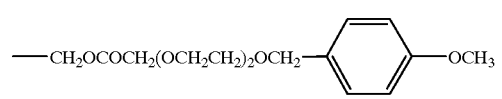 |
| 47 | COCH₂(OCH₂CH₂)₂OCH₃ | CH₂OCOCH₂(OCH₂CH₂)₂OH |

TABLE 1-continued

Examples (4) of Compounds (I)

| Compound | R¹ | Compound | R¹ |
|---|---|---|---|
| 48 | (sugar with OCH₂C₆H₅, OCH₂C₆H₅, OCH₂C₆H₅, OCH₂C₆H₅) | 59 | (sugar with OCOCH₃, OCOCH₃, OCOCH₃, OCOCH₃) |
| 49 | (sugar with OCOCH₃, OCOCH₃, OCOCH₃) | 60 | (dihydropyran with OCOCH₃, OCOCH₃) |
| 50 | (sugar with OCOCH₃, OCOCH₃) | 61 | (sugar with OSi(CH₃)₂C(CH₃)₃, OSi(CH₃)₂C(CH₃)₃, OSi(CH₃)₂C(CH₃)₃) |
| 51 | (sugar with OSi(CH₃)₂C(CH₃)₃, OSi(CH₃)₂C(CH₃)₃, OSi(CH₃)₂C(CH₃)₃) | 62 | (sugar with OH, OH, OH) |
| 52 | (sugar with OH, OH, OH) | 63 | (sugar with OSi(CH₃)₂C(CH₃)₃, OSi(CH₃)₂C(CH₃)₃) |

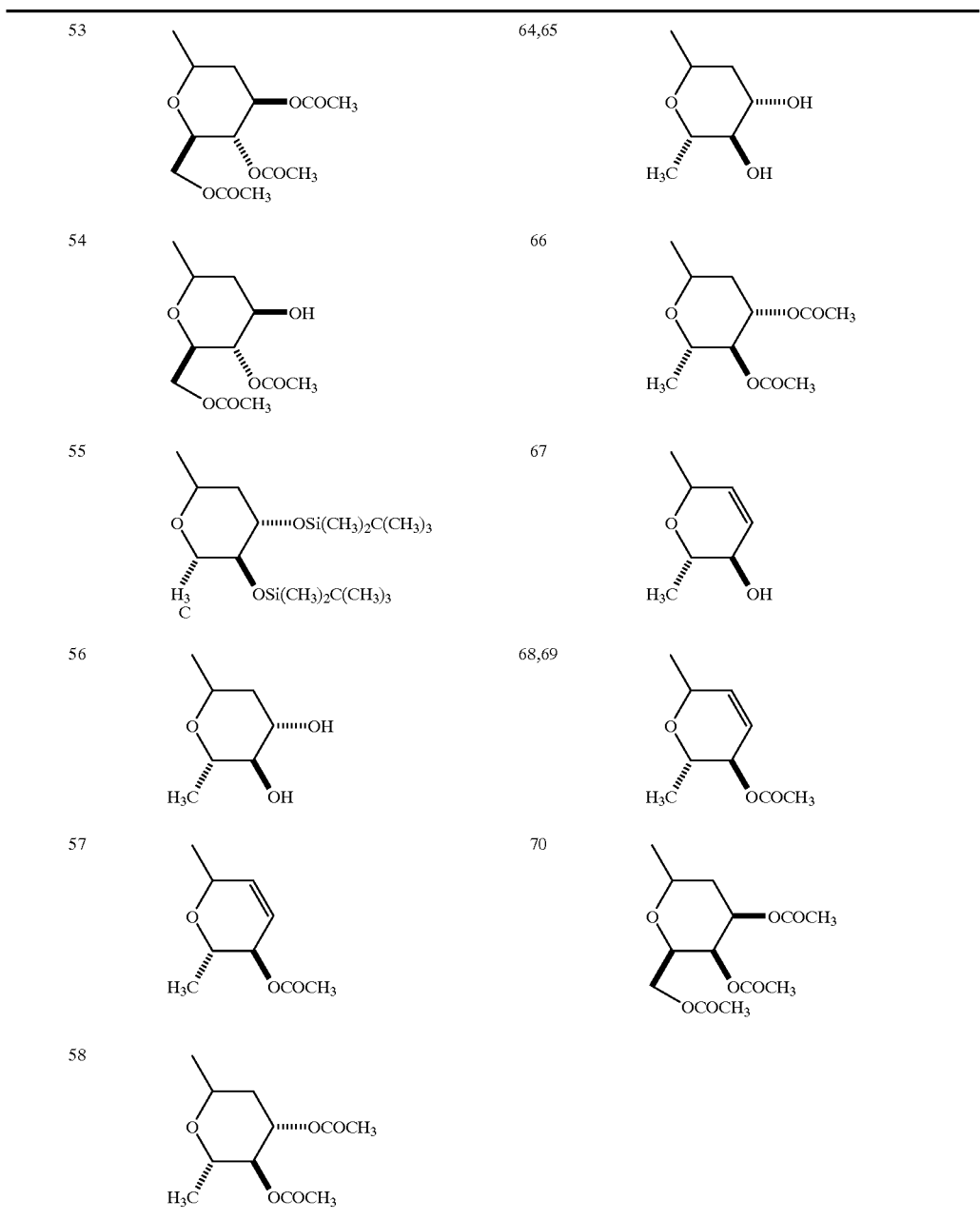

The antimicrobial activity and antitumor activity of representative compounds (I) will be demonstrated below with Test Examples.

TEST EXAMPLE 1

Antimicrobial Activity

Antimicrobial activity was determined by the agar dilution method using a culture medium (pH 7) prepared by dissolving 3 g of Bacto-Tryptone (manufactured by Difco, Co.), 3 g of meat extract, 1 g of yeast extract, 1 g of glucose, and 16 g of agar in 1 l of water. The antimicrobial activities of representative compounds are shown in Table 2 in terms of minimum inhibitory concentration (MIC).

TABLE 2

| | Antimicrobial Activity Microorganisms and MIC ($\mu$g/mL) | | | | |
|---|---|---|---|---|---|
| Compound | EH | SA | BS | KP | EC |
| 2 | 0.23 | 0.13 | 0.13 | 0.23 | 1.8 |
| 5 | 0.20 | 0.40 | 0.20 | 0.39 | 3.1 |
| 8 | 0.13 | 0.13 | 0.13 | 0.13 | 2.1 |
| 10 | 0.081 | 0.081 | 0.041 | 0.65 | 0.65 |
| 12 | 42 | 42 | 42 | 42 | 4.2 |
| 14 | 2.6 | 5.2 | 2.6 | — | — |
| 17 | 1.8 | 1.8 | 1.82 | 1.8 | — |
| 27 | 0.065 | 0.13 | 0.13 | 0.065 | 16.7 |

TABLE 2-continued

Antimicrobial Activity
Microorganisms and MIC ($\mu$g/mL)

| Compound | EH | SA | BS | KP | EC |
|---|---|---|---|---|---|
| 31 | 0.11 | 0.11 | 0.057 | 0.057 | 3.65 |
| 33 | 0.065 | 0.13 | 0.065 | 0.13 | 1.0 |
| 35 | 0.098 | 0.098 | 0.20 | 0.098 | 1.6 |
| 38 | 1.8 | 3.7 | 1.8 | 1.8 | — |
| 39 | 1.3 | 5.2 | 2.6 | 2.6 | — |
| 50 | 0.020 | 0.020 | 0.020 | 0.16 | 0.16 |
| 53 | 0.20 | 0.098 | 0.098 | 1.6 | 25 |
| 57 | 0.13 | 0.13 | 0.033 | 0.26 | 0.52 |

EH: *Enterococcus hirae* ATCC 10541
SA: *Staphylococcus aureus* ATCC 6538P
BS: *Bacillus substilis* NO. 10707
KP: *Klebisiella pneumoniae* ATCC 10031
EC: *Escherichia coli* ATCC 26

TEST EXAMPLE 2

HeLa $S_3$ Cell Growth Inhibition Test

In each well of a 96-well microtiter plate was placed 0.1 mL of HeLa $S_3$ cells having a concentration of $8 \times 10^3$ cells/mL and prepared in an MEM culture medium containing 10% fetal bovine serum and 2 mM glutamine. After the cells were incubated overnight at 37° C. in a carbon dioxide incubator, a test compound suitably diluted with a medium was added to the wells in an amount of 0.05 mL for each well. The cells were incubated at 37° C. for 72 hours in a carbon dioxide incubator. After the culture supernatant was removed, 0.1 mL of a culture medium containing 0.02% Neutral Red was added to each well. The cells were then incubated at 37° C. for 1 hour in a carbon dioxide incubator to dye the cells. After the culture supernatant was removed, each residue was rinsed once with physiological saline and the pigment was extracted with 0.001N hydrochloric acid/30% ethanol. The absorbance at 550 nm of each extract was measured with a microplate reader. The drug concentration required for the 50% inhibition of cell growth, which is referred to as $IC_{50}$, was calculated by comparing the absorbance for untreated cells with those for cells treated with the drug in known concentrations. The values of $IC_{50}$ of representative compounds are shown in Table 3.

TABLE 3

HeLa $S_3$ Cell Growth Inhibition Activity (1)

| Compound | $IC_{50}$ ($\mu$M) |
|---|---|
| 2 | 0.025 |
| 5 | 0.067 |
| 11 | 0.030 |
| 12 | 0.030 |
| 14 | 0.035 |
| 23 | 0.043 |
| 24 | 0.021 |
| 50 | 0.0035 |
| 53 | 0.016 |
| 57 | 0.016 |
| 66 | 0.0061 |
| 69 | 0.0032 |

TEST EXAMPLE 3

Antitumor Activity of Test Compounds Against Sarcoma 180 Mouse Solid Tumor

To a ddY mouse were intraperitoneally transplanted $5 \times 10^6$ sarcoma 180 cells. On the seventh day from the transplant, the cells were collected from the ascites, washed once with sterilized physiological saline, and then diluted with sterilized physiological saline to prepare a cell suspension having a concentration of $5 \times 10^7$ cells/mL. This suspension was transplanted in an amount of 0.01 mL to a subcutaneous part of the right axilla of each of male ddY mice each weighing 20±1 g.

A test compound was dissolved in physiological saline containing polyoxyethylene sorbitan monolaurate. At 24 hours after the tumor transplant, 0.2 mL of the solution was intravenously administered to the tail of each of a group of five mice.

The antitumor activity of each test compound was evaluated by measuring the major diameter (a) and minor diameter (b) of the tumor on the seventh day from the transplant and determining from these diameter values the value of $a \times b^2/2$, which corresponds to the volume of the tumor. The antitumor activity was expressed in terms of T/C ratio, i.e., the ratio of the volume for the group to which the test compound had been administered (T) to the volume for a control (untreated) group (C). The results are shown in Table 4.

TABLE 4

Antitumor Activity against S-180 Mouse Solid Tumor

| Compound | Dose (mg/kg) | T/C |
|---|---|---|
| 2 | 4.0 | 0.30 |
| 5 | 8.0 | 0.30 |
| 8 | 4.0 | 0.36 |
| 12 | 8.0 | 0.39 |
| 13 | 8.0 | 0.39 |
| 17 | 8.0 | 0.37 |
| 21 | 16 | 0.45 |
| 23 | 8.0 | 0.48 |
| 27 | 8.0 | 0.18 |
| 28 | 8.0 | 0.31 |
| 29 | 8.0 | 0.47 |
| 30 | 4.0 | 0.43 |
| 31 | 8.0 | 0.12 |
| 33 | 2.0 | 0.36 |
| 35 | 4.0 | 0.22 |
| 38 | 8.0 | 0.43 |
| 39 | 16 | 0.38 |
| 44 | 2.0 | 0.43 |
| 45 | 4.0 | 0.45 |
| 47 | 8.0 | 0.40 |
| 66 | 4.0 | 0.47 |
| 67 | 8.0 | 0.44 |
| 68 | 8.0 | 0.50 |

The compounds obtained according to the present invention are useful as antimicrobial agents and antitumor agents, and can be used as such or in various administration forms (with a pharmaceutically acceptable carrier). For example, if compound (I) is used as a parenteral agent, it may be used as a solution in a diluent ordinarily employed in this field, such as physiological saline, glucose parenteral solution, lactose parenteral solution, mannitol parenteral solution, or the like, or as an injectable powder comprising a mixture of the compound with a freeze-dried parenteral agent according to the Japanese Pharmacopeia or with sodium chloride or the like. An auxiliary agent, e.g., polyethylene glycol or HCO-60 (surfactant, manufactured by Nikko Chemicals Co., Ltd.), or a carrier, e.g., ethanol and/or liposome and cyclodextrin, may be added to those parenteral agents. Although those parenteral agents are usually administered intravenously, they can be also administered intraarterially, intraperitoneally, or intrathoracically.

Compounds (I) can be used also as a peroral agent after being mixed with an appropriate excipient, disintegrator, binder, lubricants, or the like, and molded into tablets, granules, powder, syrup, or the like.

The dose varies depending on administration method, kind of compound (I), age, condition, and the like, and the administration either method can be varied according to the condition and the dose. However, the compound can usually be administered parenterally as a parenteral agent or per-orally. For example, it can be administered in a dose of 0.01 to 6 mg/kg at an interval of 1 to 3 weeks.

EXAMPLES

Physicochemical properties of each of the compounds shown in the following Examples and Reference Examples were determined with the following apparatuses.

MS
   JEOL: JMS-D300 (measured by FAB method)
   JEOL: JMS-SX-102 (measured by FAB method)
   JEOL: HX/HX110A (measured by FAB method)
   Shimadzu: QP-1000 (measured by EI method)
$^1$H NMR Bruker: DMX500 (500 MHz)
   JEOL: a400 (400 MHz)
   JEOL: JNM-GX270 (270 MHz)
   JEOL: JNM-EX270 (270 MHz)
   JEOL:FX-100 (100 MHz)
IR JASCO: IR-810

In the physical data for compounds given in the following Examples and Reference Examples, "FABMS" means mass spectrum by the "FAB" method; "HRFABMS" means high-resolution mass spectrum by the "FAB" method; "calcd" means the theoretical value based on the molecular formula; and "found" means found value. In the Examples and Reference Examples, "Cbz" means carbobenzoxy, "Gly" means a glycine residue, "Glu" means a glutamic acid residue, "Bu$^t$" means tert-butyl, "Boc" means tert-butoxycarbonyl, "Ph" means phenyl, and "Me" means methyl. "ODS" means silica gel with modified with an octadecyl group. With respect to the NMR data for separated stereoisomers, those for the major and minor isomers are often indicated by "major isomer" and "minor isomer", respectively. If peak overlapping occurred, the peak is indicated by "overlapped with other peaks". Furthermore, "ca." and "approx." mean "approximately". A mixture of two diastereomers is indicated to this effect.

In the following Examples and Reference Examples, the term "ordinary post-treatment" means the following post-reaction treatment.

After completion of the reaction in each step, water, an acid, a buffer solution, or the like is added if necessary to the reaction mixture before the reaction mixture is extracted with a water-insoluble solvent, for example, ethyl acetate, ether, chloroform, dichloromethane, or the like. The extract is washed with water, brine, or the like, dried with anhydrous sodium sulfate, and then distilled under reduced pressure to remove the solvent.

Example 1

Synthesis of Compound 1

In dichloromethane (2.0 ml) were dissolved DC107 (51 mg, 0.10 mmol), 3,6-dioxaheptanoic acid (30 mg, 0.30 mmol), 1-ethyl-3-(3-dimethylaminopropyl)carbodiimide hydrochloride (58 mg, 0.30 mmol), and 4-dimethylaminopyridine (2.4 mg, 0.020 mmol) The resultant solution was stirred at 25° C. for 70 minutes. After the ordinary post-treatment, the reaction product was purified by thin-layer chromatography (developed with chloroform/methanol=97/3) to obtain Compound 1 (45 mg, yield 72%).

$^1$H NMR (CDCl$_3$, 400 MHz) δ ppm; 8.71 (dd, J=16.6, 11.5 Hz, 1H), 7.28 (s, 1H), 6.72 (br d, J=6.6 Hz, 1H), 6.64 (d, J=11.5 Hz, 1H), 6.34 (t, J=11.5 Hz, 1H), 6.02 (d, J=16.6 Hz, 1H), 5.88 (d, J=9.5 Hz, 1H), 5.76 (br d, J=9.5 Hz, 1H), 5.37 (dq, J=6.6, 6.6 Hz, 1H), 4.56 (br s, 1H), 4.10 (s, 2H), 3.70–3.47 (m, 4H), 3.32 (s, 3H), 3.09 (d, J=15.4 Hz, 1H), 3.01 (d, J=15.4 Hz, 1H), 2.41–1.70 (m, 4H), 1.74 (d, J=6.6 Hz, 3H), 1.74 (s, 3H), 1.71 (d, J=1.0 Hz, 3H)

FABMS m/z 627 (M+H)$^+$

HRFABMS calcd for C$_{27}$H$_{35}$N$_2$O$_9$S$_3$ (M+H)$^+$ 627.1505, found 627.1482

Example 2

Synthesis of Compound 2

In the same manner as in Example 1, Compound 2 (24 mg, yield 61%) was obtained from DC107 (30 mg, 0.059 mmol), 3,6,9-trioxadecanoic acid (31 mg, 0.18 mmol), 1-ethyl- 3-(3-dimethylaminopropyl)carbodiimide hydrochloride (34 mg, 0.18 mmol), and 4-dimethylaminopyridine (3.6 mg, 0.030 mmol).

$^1$H NMR (CDCl$_3$, 500 MHz) δ ppm; 8.70 (dd, J=16.6, 11.5 Hz, 1H), 7.29 (s, 1H), 6.67 (br d, J=5.5 Hz, 1H), 6.65 (d, J=11.5 Hz, 1H), 6.35 (t, J=11.5 Hz, 1H), 6.04 (d, J=16.6 Hz, 1H), 5.88 (d, J=9.8 Hz, 1H), 5.77 (br d, J=9.8 Hz, 1H), 5.37 (dq, J=6.6, 5.5 Hz, 1H), 4.33 (br 5, 1H), 4.12 (d, J=16.8 Hz, 1H), 4.08 (d, J=16.8 Hz, 1H), 3.72–3.48 (m, 8H), 3.35 (s, 3H), 3.10 (d, J=15.4 Hz, 1H), 3.03 (d, J=15.4 Hz, 1H), 2.40–1.68 (m, 4H), 1.75 (s, 3H), 1.74 (d, J=6.6 Hz, 3H), 1.72 (s, 3H)

FABMS m/z 671 (M+H)$^+$

HRFABMS calcd for C$_{29}$H$_{39}$N$_2$O$_{10}$S$_3$ (M+H)$^+$ 671.1767, found 671.1786

Example 3

Synthesis of Compound 3

In the same manner as in Example 1, Compound 3 (49 mg, yield 69%) was obtained from DC107 (51 mg, 0.10 mmol), 3,6,9,12-tetraoxatridecanoic acid (67 mg, 0.30 mmol), 1-ethyl-3-(3-dimethylaminopropyl)carbodiimide hydrochloride (58 mg, 0.30 mmol), and 4-dimethylaminopyridine (6.0 mg, 0.050 mmol).

$^1$H NMR (CDCl$_3$, 400 MHz) δ ppm; 8.69 (dd, J=16.6, 11.5 Hz, 1H), 7.29 (s, 1H), 6.76 (br d, J=6.6 Hz, 1H), 6.65 (d, J=11.2 Hz, 1H), 6.34 (dd, J=11.5, 11.2 Hz, 1H), 6.03 (d, J=16.6 Hz, 1H), 5.89 (d, J=9.5 Hz, 1H), 5.76 (br d, J=9.5 Hz, 1H), 5.37 (dq, J=6.6, 6.8 Hz, 1H), 4.40 (br s, 1H), 4.10 (s, 2H), 3.95–3.50 (m, 12H), 3.36 (s, 3H), 3.10 (d, J=15.6 Hz, 1H), 3.00 (d, J=15.6 Hz, 1H), 2.42–1.65 (m, 4H), 1.74 (s, 3H), 1.73 (d, J=6.8 Hz, 3H), 1.73 (d, J=1.0 Hz, 3H)

FABMS m/z 715 (M+H)$^+$

HRFABMS calcd for C$_{31}$H$_{43}$N$_2$O$_{11}$S$_3$ (M+H)$^+$ 715.2029, found 715.2009

Example 4

Synthesis of Compound 4

In the same manner as in Example 1, Compound 4 (37 mg, yield 49%) was obtained from DC107 (51 mg, 0.10 mmol), 3,6,9,12,15-pentaoxahexadecanoic acid (80 mg, 0.30 mmol), 1-ethyl-3-(3-dimethylaminopropyl) carbodiimide hydrochloride (58 mg, 0.30 mmol), and 4-dimethylaminopyridine (6.0 mg, 0.050 mmol).

$^1$H NMR (CDCl$_3$, 400 MHz) δ ppm; 8.68 (dd, J=16.6, 11.2 Hz, 1H), 7.29 (s, 1H), 6.66 (br d, J=6.2 Hz, 1H), 6.65

(d, J=11.7 Hz, 1H), 6.35 (dd, J=11.7, 11.2 Hz, 1H), 6.03 (d, J=16.6 Hz, 1H), 5.89 (d, J=9.8 Hz, 1H), 5.76 (br d, J=9.8 Hz, 1H), 5.38 (dq, J=6.2, 6.6 Hz, 1H), 4.15 (br s, 1H), 4.10 (s, 2H), 3.68–3.52 (m, 16H), 3.37 (s, 3H), 3.10 (d, J=15.4 Hz, 1H), 3.01 (d, J=15.4 Hz, 1H), 2.40–1.70 (m, 4H), 1.75 (d, J=6.6 Hz, 3H), 1.74 (s, 3H), 1.71 (d, J=1.0 Hz, 3H)

FABMS m/z 759 (M+H)$^+$

HRFABMS calcd for $C_{33}H_{47}N_2O_{12}S_3$ (M+H)$^+$ 759.2291, found 759.2289

Example 5

Synthesis of Compound 5

In the same manner as in Example 1, Compound 5 (39 mg, yield 52%) was obtained from DC107 (48 mg, 0.094 mmol), 3,6,9,12,15,18-hexaoxanonadecanoic acid (87 mg, 0.28 mmol), 1-ethyl-3-(3-dimethylaminopropyl)carbodiimide hydrochloride (54 mg, 0.28 mmol), and 4-dimethylaminopyridine (5.0 mg, 0.047 mmol).

$^1$H NMR (CDCl$_3$, 400 MHz) δ ppm; 8.68 (dd, J=16.6, 11.5 Hz, 1H), 7.30 (s, 1H), 6.66 (br d, J=6.6 Hz, 1H), 6.65 (d, J=11.5 Hz, 1H), 6.35 (t, J=11.5 Hz, 1H), 6.04 (d, J=16.6 Hz, 1H), 5.90 (d, J=9.8 Hz, 1H), 5.76 (br d, J=9.8 Hz, 1H), 5.38 (dq, J=6.6, 6.6 Hz, 1H), 4.37 (br s, 1H), 4.12 (s, 2H), 3.70–3.52 (m, 20H), 3.37 (s, 3H), 3.10 (d, J=15.4 Hz, 1H), 3.02 (d, J=15.4 Hz, 1H), 2.42–1.60 (m, 4H), 1.75 (d, J=6.6 Hz, 3H), 1.75 (s, 3H), 1.72 (d, J=1.0Hz, 3H)

FABMS m/z 803(M+H)$^+$

HRFABMS calcd for $C_{35}H51N_2O_{13}S_3$ (M+H)$^+$ 803.2553, found 803.2554

Example 6

Synthesis of Compound 6

In the same manner as in Example 1, Compound 6 (7.0 mg, yield 8.0%) was obtained from DC107 (51 mg, 0.10 mmol), 3,6,9,12,15,18,21-heptaoxadocosanoic acid (106 mg, 0.30 mmol), 1-ethyl-3-(3-dimethylaminopropyl)carbodiimide hydrochloride (58 mg, 0.30 mmol), and 4-dimethylaminopyridine (6.0 mg, 0.050 mmol).

$^1$H NMR (CDCl$_3$, 500 MHz) δ ppm; 8.66 (dd, J=16.5, 11.4 Hz, 1H), 7.29 (s, 1H), 6.85 (br d, J=6.3 Hz, 1H), 6.64 (d, J=11.4 Hz, 1H), 6.34 (t, J=11.4 Hz, 1H), 6.02 (d, J=16.5 Hz, 1H), 5.90 (d, J=9.6 Hz, 1H), 5.76 (br d, J=9.6 Hz, 1H), 5.37 (dq, J=6.3, 6.6 Hz, 1H), 4.50 (br s, 1H), 4.11 (s, 2H), 3.74–3.50 (m, 24H), 3.37 (s, 3H), 3.11 (d, J=15.5 Hz, 1H), 3.01 (d, J=15.5 Hz, 1H), 2.42–1.55 (m, 4H), 1.74 (d, J=6.6 Hz, 3H), 1.73 (s, 3H), 1.70 (d, J=1.0 Hz, 3H)

FABMS m/z 847 (M+H)$^+$

HRFABMS calcd for $C_{37}H_{55}N_2O_{14}S_3$ (M+H)$^+$ 847.2815, found 847.2830

Example 7

Synthesis of Compound 7

In the same manner as in Example 1, Compound 7 (62 mg, yield 58%) was obtained from DC107 (60 mg, 0.12 mmol), 8-tert-butyldiphenylsilyloxy-3,6-dioxaoctanoic acid (142 mg, 0.35 mmol), 1-ethyl-3-(3-dimethylaminopropyl)carbodiimide hydrochloride (67 mg, 0.35 mmol), and 4-dimethylaminopyridine (3.0 mg, 0.025 mmol).

$^1$H NMR (CDCl$_3$, 400 MHz) δ ppm; 8.71 (dd, J=16.6, 11.5 Hz, 1H), 7.70–7.62 (m, 4H), 7.45–7.32 (m, 6H), 7.24 (s, 1H), 6.66 (br d, J=6.4 Hz, 1H), 6.62 (d, J=11.2 Hz, 1H), 6.33 (dd, J=11.5, 11.2 Hz, 1H), 6.03 (d, J=16.6 Hz, 1H), 5.88 (d, J=9.8 Hz, 1H), 5.76 (br d, J=9.8 Hz, 1H), 5.35 (dq, J=6.4, 6.6 Hz, 1H), 4.34 (br s, 1H), 4.09 (m, 2H), 3.80–3.52 (m, 8H), 3.09 (d, J=15.4 Hz, 1H), 3.02 (d, J=15.4 Hz, 1H), 2.40–1.55 (m, 4H), 1.75 (s, 3H), 1.73 (d, J=6.6 Hz, 3H), 1.71 (d, J=1.0 Hz, 3H), 1.03 (s, 9H)

FABMS m/z 895 (M+H)$^+$

HRFABMS calcd for $C_{44}H_{55}N_2O_{10}SiS_3$ (M+H)$^+$ 895.2788, found 895.2817

Example 8

Synthesis of Compound 8

Compound 7 (30 mg, 0.034 mmol) obtained in Example 7 was dissolved in THF (3.0 ml). Thereto was added 3N hydrochloric acid (0.7 ml). This mixture was stirred at 20° C. for 8 hours. After the ordinary post-treatment, the reaction product was purified by thin-layer chromatography (developed with chloroform/methanol=96/4) to obtain Compound 8 (11 mg, yield 49%).

$^1$H NMR (CDCl$_3$, 500 MHz) δ ppm; 8.56 (dd, J=16.5, 11.5 Hz, 1H), 7.28 (s, 1H), 6.70 (br d, J=7.2 Hz, 1H), 6.66 (d, J=11.3 Hz, 1H), 6.35 (dd, J=11.5, 11.3 Hz, 1H), 6.04 (d, J=16.4 Hz, 1H), 5.93 (d, J=9.8 Hz, 1H), 5.72 (br d, J=9.8 Hz, 1H), 5.39 (dq, J=6.7, 7.2 Hz, 1H), 4.30 (br s, 1H), 4.13 (br s, 2H), 3.74–3.54 (m, 8H), 3.15 (d, J=15.6 Hz, 1H), 2.96 (d, J=15.6 Hz, 1H), 2.40–1.60 (m, 4H), 1.74 (d, J=6.6 Hz, 3H), 1.71 (s, 3H), 1.70 (d, J=1.0 Hz, 3H)

FABMS m/z 657 (M+H)$^+$

HRFABMS calcd for $C_{28}H_{36}N_2O_{10}S_3$ (M+H)$^+$ 657.1610, found 657.1598

Example 9

Synthesis of Compound 9

In the same manner as in Example 1, Compound 9 (22 mg, yield 32%) was obtained from DC107 (51 mg, 0.10 mmol), 2-methyl-3,6,9-trioxadecanoic acid (57 mg, 0.30 mmol), 1-ethyl-3-(3-dimethylaminopropyl)carbodiimide hydrochloride (57 mg, 0.30 mmol), and 4-dimethylaminopyridine (6.0 mg, 0.050 mmol). $^1$H NMR revealed that this Compound 9 was an approximately 2:1 mixture of diastereomers.

$^1$H NMR (CDCl$_3$, 400 MHz) δ ppm; major isomer8.73 (dd, J=16.7, 11.5 Hz, 1H), 7.28 (s, 1H), 6.66 (br d, J=6.6 Hz, 1H), 6.64 (d, J=11.5 Hz, 1H), 6.34 (t, J=11.5 Hz, 1H), 6.02 (d, J=16.7 Hz, 1H), 5.79 (br s, 2H), 5.38 (dq, J=6.6, 6.6 Hz, 1H), 4.34 (br s, 1H), 3.98 (q, J=6.6 Hz, 1H), 3.75–3.44 (m, 8H), 3.36 (s, 3H), 3.13–3.02 (m, 2H), 2.42–1.70 (m, 4H), 1.77 (d, J=6.6 Hz, 3H), 1.76 (d, J=1.0 Hz, 3H), 1.72 (s, 3H), 1.33 (d, J=6.6 Hz, 3H); minor isomer 8.74 (dd, J=16.7, 11.5 Hz, 1H), 7.28 (s, 1H), 6.66 (br d, J=6.6 Hz, 1H), 6.64 (d, J=11.5 Hz, 1H), 6.34 (t, J=11.5 Hz, 1H), 6.01 (d, J=16.7 Hz, 1H), 5.82 (br s, 2H), 5.38 (dq, J=6.6, 6.6 Hz, 1H), 4.36 (br s, 1H), 4.01 (q, J=6.6 Hz, 1H) 3.75–3.44 (m, 8H), 3.36 (s, 3H), 3.13–3.02 (m, 2H), 2.42–1.70 (m, 4H), 1.77 (d, J=6.6 Hz, 3H), 1.76 (d, J=1.0 Hz, 3H), 1.73 (s, 3H), 1.27 (d, J=6.6 Hz, 3H)

FABMS m/z 685 (M+H)$^+$

HRFABMS calcd for $C_{30}H_{41}N_2O_{10}S_3$ (M+H)$^+$ 685.1923, found 685.1908

Example 10

Synthesis of Compound 10

In the same manner as in Example 1, Compound 10 (18 mg, yield 26%) was obtained from DC107 (49 mg, 0.097 mmol), 2,2-dimethyl-3,6,9-trioxadecanoic acid (100 mg, 0.49 mmol), 1-ethyl-3-(3-dimethylaminopropyl) carbodiimide hydrochloride (94 mg, 0.49 mmol), and 4-dimethylaminopyridine (6.0 mg, 0.049 mmol).

$^1$H NMR (CDCl$_3$, 400 MHz) δ ppm; 8.69 (dd, J=16.7, 11.5 Hz, 1H), 7.28 (s, 1H), 6.68 (br d, J=6.6 Hz, 1H), 6.63 (d, J=11.5 Hz, 1H), 6.33 (t, J=11.5 Hz, 1H), 6.00 (d, J=16.6 Hz, 1H), 5.84 (br d, J=9.7 Hz, 1H), 5.76 (d, J=9.7 Hz, 1H), 5.39 (dq, J=6.6, 6.6 Hz, 1H), 4.32 (brs, 1H), 3.62–3.45 (m, 8H), 3.36 (s, 3H), 3.69 (d, J=15.4 Hz, 1H), 3.04 (d, J=15.4 Hz, 1H), 2.43–1.75 (m, 4H), 1.78 (d, J=6.6 Hz, 3H), 1.76 (s, 3H), 1.72 (d, J=1.0 Hz, 3H), 1.26 (s, 6H)

FABMS m/z 699 (M+H)$^+$

HRFABMS calcd for C$_{31}$H$_{43}$N$_2$O$_{10}$S$_3$ (M+H)$^+$ 699.2080, found 699.2081

Example 11

Synthesis of Compound 11

In the same manner as in Example. 1, Compound 11 (22 mg, yield 41%) was obtained from Compound A (45 mg, 0.072 mmol) obtained in Reference Example 1, 3,6-dioxaheptanoic acid (29 mg, 0.22 mmol), 1-ethyl-3-(3-dimethylaminopropyl)carbodiimide hydrochloride (42 mg, 0.22 mmol), and 4-dimethylaminopyridine (9.0 mg, 0.072 mmol).

IR (KBr) 3420, 3100, 2932, 1820, 1740, 1720, 1680, 1648, 1609, 1451, 1374, 1260, 1140, 973, 861, 768 cm$^{-1}$ $^1$H NMR (CDCl$_3$, 400 MHz) δ ppm, 9.17 (ddd, J=16.6, 11.5, 1.0 Hz, 1H), 7.42 (s, 1H), 6.61 (d, J=11.5 Hz, 1H), 6.32 (t, J=11.5 Hz, 1H), 6.03 (d, J=16.6 Hz, 1H), 5.76 (br s, 2H), 5.58 (q, J=6.6 Hz, 1H), 5.42 (br s, 1H), 4.12 (br s, 2H), 4.03 (d, J=17.8 Hz, 1H), 3.78 (br s, 2H), 3.70–3.63 (m, 2H), 3.52–3.47 (m, 2H), 3.31 (s, 3H), 2.50–2.20 (m, 3H), 2.28 (d, J=17.8 Hz, 1H), 2.14 (s, 3H), 1.89 (d, J=6.6 Hz, 3H) 1.79 (s, 3H), 1.71 (s, 3H), 1.60–1.45 (m, 1H)

FABMS m/z 739 (M+H)$^+$

HRFABMS calcd for C$_{32}$H$_{39}$N$_2$O$_{12}$S$_3$ (M+H)$^+$ 739.1665, found 739.1677

Example 12

Synthesis of Compound 12

In the same manner as in Example 1, Compound 12 (23 mg, yield 41%) was obtained from Compound A (45 mg, 0.059 mmol) obtained in Reference Example 1, 3,6,9-trioxadecanoic acid (39 mg, 0.22 mmol), 1-ethyl-3-(3-dimethylaminopropyl)carbodiimide hydrochloride (42 mg, 0.22 mmol), and 4-dimethylaminopyridine (9.0 mg, 0.072 mmol).

IR (KBr) 3420, 2930, 1810, 1720, 1680, 1650, 1610, 1452, 1370, 1260, 1190, 974, 861, 769 cm$^{-1}$ $^1$H NMR (CDCl$_3$, 500 MHz) δ ppm; 9.18 (ddd, J=16.6, 11.5, 0.8 Hz, 1H), 7.43 (s, 1H), 6.61 (d, J=11.5 Hz, 1H), 6.31 (t, J=11.5 Hz, 1H), 6.02 (d, J=16.6 Hz, 1H), 5.80–5.70 (m, 2H), 5.58 (q, J=6.6 Hz, 1H), 5.43 (br s, 1H), 4.11 (br s, 2H), 4.03 (d, J=17.7 Hz, 1H), 3.77 (br s, 2H), 3.70–3.45 (m, 8H), 3.34 (s, 3H), 2.44–2.23 (m, 3H), 2.28 (d, J=17.7 Hz, 1H), 2.14 (s, 3H), 1.89 (d, J=6.6 Hz, 3H), 1.79 (d, J=0.8 Hz, 3H), 1.71 (s, 3H), 1.53–1.47 (m, 1H)

FABMS m/z 783 (M+H)$^+$

HRFABMS calcd for C$_{34}$H$_{43}$N$_2$O$_{13}$S$_3$ (M+H)$^+$ 783.1927, found 783.1927

Example 13

Synthesis of Compound 13

In the same manner as in Example 1, Compound 13 (22 mg, yield 41%) was obtained from Compound A (40 mg, 0.064 mmol) obtained in Reference Example 1, 3,6,9,12-tetraoxatridecanoic acid (42 mg, 0.19 mmol), 1-ethyl-3-(3-dimethylaminopropyl)carbodiimide hydrochloride (37 mg, 0.19 mmol), and 4-dimethylaminopyridine (4.0 mg, 0.032 mmol).

$^1$H NMR (CDCl$_3$, 400 MHz) δ ppm; 9.16 (dd, J=16.6, 11.5 Hz, 1H), 7.43 (s, 1H), 6.62 (d, J=11.5 Hz, 1H), 6.32 (t, J=11.5 Hz, 1H), 6.03 (d, J=16.6 Hz, 1H), 5.76 (br s, 2H), 5.58 (q, J=6.6 Hz, 1H), 5.43 (br s, 1H), 4.11 (br s, 2H), 4.03 (d, J=11.6 Hz, 1H), 3.77 (br s, 2H), 3.70–3.50 (m, 12H), 3.36 (s, 3H), 2.50–1.45 (m, 4H), 2.28(d, J=17.6 Hz, 1H), 2.14 (s, 3H), 1.89 (d, J=6.6 Hz, 3H), 1.79 (s, 3H), 1.71 (s, 3H)

FABMS m/z 827 (M+H)$^+$

HRFABMS calcd for C$_{36}$H$_{47}$N$_2$O$_{14}$S$_3$ (M+H)$^+$ 827.2189, found 827.2173

Example 14

Synthesis of Compound 14

In the same manner as in Example 1, Compound 14 (25 mg, yield 35%) was obtained from Compound A (50 mg, 0.080 mmol) obtained in Reference Example 1, 3,6,9,12,15-pentaoxahexadecanoic acid (64 mg, 0.24 mmol), 1-ethyl-3-(3-dimethylaminopropyl)carbodiimide hydrochloride (46 mg, 0.24 mmol), and 4-dimethylaminopyridine (5.0 mg, 0.040 mmol).

IR (KBr) 3420, 2930, 2880, 1819, 1760, 1705, 1680, 1657, 1609, 1450, 1370, 1267, 1204, 1093, 975, 852, 768 cm$^{-1}$ $^1$H NMR (CDCl$_3$, 400 MHz) δ ppm; 9.16 (ddd, J=16.6, 11.5, 1.0 Hz, 1H), 7.43 (s, 1H), 6.62 (d, J=11.5 Hz, 1H), 6.32 (t, J=11.5 Hz, 1H), 6.03 (d, J=16.6 Hz, 1H), 5.76 (br s, 2H), 5.58 (q, J=6.6 Hz, 1H), 5.43 (br s, 1H), 4.11 (br s, 2H), 4.03 (d, J=17.6 Hz, 1H), 3.77 (br s, 2H), 3.68–3.52 (m, 16H), 3.37 (s, 3H), 2.48–2.20 (m, 3H), 2.28 (d, J=17.6 Hz, 1H), 2.14 (s, 3H), 1.89 (d, J=6.6 Hz, 3H), 1.79 (s, 3H), 1.71 (s, 3H), 1.55–1.45 (m, 1H)

FABMS m/z 870 (M+H)$^+$

HRFABMS calcd for C$_{38}$H$_{51}$N$_2$O$_{15}$S$_3$ (M+H)$^+$ 871.2452, found 871.2451

Example 15

Synthesis of Compound 15

In the same manner as in Example 1, Compound 15 (45 mg, yield 51%) was obtained from Compound A (60 mg, 0.096 mmol) obtained in Reference Example 1, 3,6,9,12,15,18-hexaoxanonadecanoic acid (90 mg, 0.29 mmol), 1-ethyl-3-(3-dimethylaminopropyl)carbodiimide hydrochloride (56 mg, 0.29 mmol), and 4-dimethylaminopyridine (6.0 mg, 0.048 mmol).

$^1$H NMR (CDCl$_3$, 400 MHz) δ ppm; 9.16 (ddd, J=16.6, 11.3, 1.0 Hz, 1H), 7.43 (s, 1H), 6.62 (d, J=11.5 Hz, 1H), 6.32 (t, J=11.5 Hz, 1H), 6.03 (d, J=16.6 Hz, 1H), 5.76 (br s, 2H), 5.57 (q, J=6.6 Hz, 1H), 5.44 (br s, 1H), 4.11 (s, 2H), 4.03 (d, J=17.6 Hz, 1H), 3.76 (br s, 2H), 3.70–3.50 (m, 20H), 3.37 (s, 3H), 2.48–1.45 (m, 4H), 2.28 (d, J=17.8 Hz, 1H), 2.14 (s, 3H), 1.89 (d, J=6.6 Hz, 3H), 1.79 (s, 3H), 1.70 (s, 3H)

FABMS m/z 915 (M+H)$^+$

HRFABMS calcd for C$_{40}$H$_{55}$N$_2$O$_{16}$S$_3$ (M+H)$^+$ 915.2713, found 915.2708

Example 16

Syntheses of Compounds 16 and 17

In the same manner as in Example 7, crude Compound 16 was obtained from Compound A (50 mg, 0.080 mmol)

obtained in Reference Example 1, 8-tert-butyldiphenylsilyloxy-3,6-dioxaoctanoic acid (97 mg, 0.24 mmol), 1-ethyl-3-(3-dimethylaminopropyl)carbodiimide hydrochloride (46 mg, 0.24 mmol), and 4-dimethylaminopyridine (5.0 mg, 0.040 mmol).

Compound 16

FABMS m/z 1029 (M+Na)$^+$

In the same manner as in Example 8, the Compound 16 obtained was treated with 3N hydrochloric acid (1.0 ml) in THF (3.0 ml) to thereby obtain Compound 17 (18 mg, yield 29%).

Compound 17

$^1$H NMR (CDCl$_3$, 400 MHz) δ ppm; 9.12 (ddd, J=16.6, 11.5, 1.0 Hz, 1H), 7.42 (s, 1H), 6.62 (d, J=11.5 Hz, 1H), 6.32 (t, J=11.5 Hz, 1H), 6.04 (d, J=16.6 Hz, 1), 5.77 (br s, 2H), 5.57 (q, J=6.6 Hz, 1H), 5.41 (br s, 1H), 4.12 (br s, 2H), 4.02 (d, J=17.8 Hz, 1H), 3.78 (br s, 2H), 3.77–3.55 (m, 8H), 2.50–1.50 (m, 4H), 2.28 (d, J=17.8 Hz, 1H), 2.14 (s, 3H), 1.90 (d, J=6.6 Hz, 3H), 1.80 (s, 3H), 1.71 (s, 3H)

FABMS m/z 769 (M+H)$^+$

HRFABMS calcd for C$_{33}$H$_{41}$N$_2$O$_{13}$S$_3$ (M+H)$^+$ 769.1771, found 769.1774

Example 17

Synthesis of Compound 18

Compound B (40 mg, 0.062 mmol) obtained in Reference Example 2 was dissolved in dichloromethane (4.0 ml). Thereto were added 3,6-dioxaheptanoic acid (0.021 ml, 0.19 mmol), 1-ethyl-3-(3-dimethylaminopropyl)carbodiimide hydrochloride (36 mg, 0.19 mmol), and 4-dimethylaminopyridine (3.8 mg, 0.31 mmol). This mixture was stirred at 25° C. for 5 minutes. After the ordinary post-treatment, the reaction product was purified by thin-layer chromatography (developed with chloroform/methanol=20/1) to obtain Compound 18 (16 mg, yield 30%).

$^1$H NMR (CDCl$_3$, 400 MHz) δ ppm; 9.19 (ddd, J=16.6, 11.5, 0.8 Hz, 1H), 7.42 (s, 1H), 6.62 (d, J=11.5 Hz, 1H), 6.32 (dd, J=11.5, 11.5 Hz, 1H), 6.03 (d, J=16.6 Hz, 1H), 5.76 (s, 2H), 5.58 (q, J=6.6 Hz, 1H), 5.44 (br, 1H), 5.07 (d, J=13.9 Hz, 1H), 5.02 (d, J=13.9 Hz, 1H), 4.22 (s, 2H), 4.02 (d, J=17.8 Hz, 1H), 3.93 (d, J=11.0 Hz, 1H), 3.77 (d, J=11.0 Hz, 1H), 3.75–3.65 (m, 4H), 3.60–3.48 (m, 4H), 3.48 (s, 6H), 3.42 (m, 2H), 2.50–2.18 (m, 4H), 2.30 (d, J=17.8 Hz, 1H), 1.89 (d, J=6.6 Hz, 3H), 1.79 (s, 3H), 1.70 (d, J=1.2 Hz, 3H)

FABMS m/z 871 (M+H)$^+$ calcd for C$_{37}$H$_{46}$N$_2$O$_{16}$S$_3$=870

Example 18

Synthesis of Compound 19

According to the synthesis of Compound 18, Compound 19 (16 mg, yield 56%) was obtained from Compound B (19 mg, 0.030 mmol) obtained in Reference Example 2, dichloromethane (1.9 ml), 3,6,9-trioxadecanoic acid (0.014 ml, 0.091 mmol), 1-ethyl-3-(3-dimethylaminopropyl)carbodiimide hydrochloride (17 mg, 0.091 mmol), and 4-dimethylaminopyridine (19 mg, 0.15 mmol).

$^1$H NMR (CDCl$_3$, 400 MHz) δ ppm; 9.18 (dd, J=16.7, 11.3 Hz, 1H), 7.43 (s, 1H), 6.62 (d, J=11.3 Hz, 1H), 6.32 (dd, J=11.3, 11.3 Hz, 1H), 6.02 (d, J=16.7 Hz, 1H), 5.76 (d, J=9.4 Hz, 1H), 5.74 (d, J=9.4 Hz, 1H), 5.57 (q, J=6.5 Hz, 1H), 5.07 (d, J=13.9 Hz, 1H), 5.00 (d, J=13.9 Hz, 1H), 4.21 (s, 2H), 4.02 (d, J=17.7 Hz, 1H), 3.95 (d, J=15.4 Hz, 1H), 3.88 (d, J=15.4 Hz, 1H), 3.80–2.80 (m, 16H), 3.37 (s, 6H), 3.33 (s, 2H), 2.49–1.92 (m, 4H), 2.29 (d, J=17.7 Hz, 1H), 1.88 (d, J=6.6 Hz, 3H), 1.79 (s, 3H), 1.68 (s, 3H)

FABMS m/z 959 (M+H)$^+$ calcd for C$_{41}$H$_{54}$N$_2$O$_{18}$S$_3$=958

Example 19

Synthesis of Compound 20

In the same manner as in Example 1, Compound 20 (23 mg, yield 43%) was obtained from Compound C (36 mg, 0.059 mmol) obtained in Reference Example 3, 3,6,9,12,15,18-hexaoxanonadecanoic acid (56 mg, 0.18 mmol), 1-ethyl-3-(3-dimethylaminopropyl)carbodiimide hydrochloride (34 mg, 0.18 mmol), and 4-dimethylaminopyridine (3.6 mg, 0.030 mmol).

$^1$H NMR (CDCl$_3$, 500 MHz) δ ppm; 9.19 (dd, J=16.6, 11.3 Hz, 1H), 7.43 (s, 1H), 7.43 (s, 1H), 6.62 (d, J=11.5 Hz, 1H), 6.31 (t, J=11.5 Hz, 1H), 6.24 (d, J=1.0 Hz, 1H), 6.02 (d, J=16.6 Hz, 1H), 5.86 (d, J=1.0 Hz, 1H), 5.75 (br s, 2H), 5.58 (q, J=6.6 Hz, 1H), 5.43 (br s, 1H), 4.10 (s, 2H), 3.78 (s, 3H), 3.78–3.52 (m, 22H), 3.37 (s, 3H), 2.45–1.40 (m, 4H), 2.28 (d, J=17.8 Hz, 1H), 1.88 (d, J=6.6 Hz, 3H), 1.78 (s, 3H), 1.70 (s, 3H)

FABMS m/z 901 (M+H)$^+$

HRFABMS calcd for C$_{40}$H$_{57}$N$_2$O$_{15}$S$_3$ (M+H)$^+$ 901.2921, found 901.2933

Example 20

Synthesis of Compound 21

In the same manner as in Example 1, Compound 21 (18 mg, yield 36%) was obtained from Compound D (35 mg, 0.053 mmol) obtained in Reference Example 4, 3,6,9,12,15,18-hexaoxanonadecanoic acid (49 mg, 0.16 mmol), 1-ethyl-3-(3-dimethylaminopropyl)carbodiimide hydrochloride (31 mg, 0.16 mmol), and 4-dimethylaminopyridine (3.2 mg, 0.027 mmol).

$^1$H NMR (CDCl$_3$, 400 MHz) δ ppm; 9.18 (dd, J=16.8, 11.5 Hz, 1H), 7.42 (s, 1H), 6.61 (d, J=11.5 Hz, 1H), 6.31 (t, J=11.5 Hz, 1H), 6.02 (d, J=16.6 Hz, 1H), 5.75 (br s, 2H), 5.57 (q, J=6.6 Hz, 1H), 5.36 (br s, 1H), 4.10 (s, 2H), 4.03 (d, J=17.8 Hz, 1H), 3.85 (d, J=13.8 Hz, 1H), 3.70 (d, J=13.8 Hz, 1H), 3.67–3.53 (m, 20H), 3.37 (s, 3H), 2.46–1.42 (m, 4H), 2.34 (d, J=17.8 Hz, 1H), 2.08 (s, 3H), 1.88 (d, J=6.6 Hz, 3H), 1.78 (s, 3H), 1.71 (s, 3H), 1.63 (s, 6H)

FABMS m/z 957 (M+H)$^+$

HRFABMS calcd for C$_{43}$H$_{61}$N$_2$O$_{16}$S$_3$ (M+H)$^+$ 957.3183, found 957.3184

Example 21

Synthesis of Compound 22

Compound E (10 mg, 0.014 mmol) obtained in Reference Example 5 was dissolved in dichloromethane (0.5 ml). Thereto were added 3,6,9-trioxadecanoic acid (14 mg, 0.079 mmol), 1-ethyl-3-(3-dimethylaminopropyl)carbodiimide hydrochloride (13 mg, 0.069 mmol), and dimethylaminopyridine (1.3 mg, 0.011 mmol). This mixture was stirred at 25° C. for 21 hours. The reaction mixture was purified as such by thin-layer chromatography (developed with chloroform/methanol=20/1), powdered with n-hexane/chloroform, and then dried to obtain Compound 22 (4.0 mg, yield 33%).

$^1$H NMR (CDCl$_3$, 270 MHz) δ ppm; 9.21 (dd, J=11.5, 16.8 Hz, 1H), 7.43 (s, 1H), 6.62 (d, J=11.5 Hz, 1H), 6.32 (t, J=11.5 Hz, 1H), 6.03 (d, J=16.8 Hz, 1H), 5.75 (br s, 2H), 5.59 (q, J=6.6 Hz, 1H), 5.5–5.4 (m, 3H), 4.98 (br s, 1H), 4.12 (s, 2H), 4.02 (d, J=17.8 Hz, 1H), 3.90 (br d, J=5.6 Hz, 2H), 3.7–3.5 (m, 8H), 3.35 (s, 3H), 2.5–1.5 (m, 4H), 2.31 (d, J=17.8 Hz, 1H), 1.87 (d, J=6.6 Hz, 3H), 1.72 (s, 3H), 1.62 (s, 3H), 1.45 (s, 9H)

FABMS m/z 880 (M+Na)$^+$ calcd for $C_{37}H_{51}N_3O_{14}S_3$= 857 #

Example 22

Synthesis of Compound 23

According to the method used in Example 21, Compound 23 (2.7 mg, yield 23%) was obtained from Compound F (10 mg, 0.012 mmol) obtained in Reference Example 6, dichloromethane (0.5 ml), 3,6,9-trioxadecanoic acid (13 mg, 0.070 mmol), 1-ethyl-3-(3-dimethylaminopropyl)carbodiimide hydrochloride (12 mg, 0.063 mmol), and dimethylaminopyridine (1.3 mg, 0.011 mmol).

$^1$H NMR (CDCl$_3$, 270 MHz) δ ppm; 9.22 (dd, J=11.1, 16.8 Hz, 1H), 7.43 (s, 1H), 6.62 (d, J=11.2 Hz, 1H), 6.32 (t, J=11.2 Hz, 1H), 6.03 (d, J=16.8 Hz, 1H), 5.75 (br s, 2H), 5.59 (q, J=6.6 Hz, 1H), 5.50 (br s, 1H), 5.40 (br s, 2H), 5.08 (br s, 1H), 4.20 (br s, 1H), 4.11 (s, 2H), 4.03 (d, J=17.8 Hz, 1H), 3.7–3.5 (m, 8H), 3.34 (s, 3H), 2.5–1.5 (m, 8H), 2.31 (d, J=17.8 Hz, 1H), 1.88 (d, J=6.6 Hz, 3H), 1.79 (s, 3H), 1.61 (s, 3H), 1.46 (s, 9H), 1.44 (s, 9H)

FABMS m/z 986 (M+H)$^+$ calcd for $C_{44}H_{63}N_3O_{16}S_3$=985

Example 23

Synthesis of Compound 24

Compound E (52 mg, 0.075 mmol) obtained in Reference Example 5 was dissolved in dichloromethane (2.6 ml). Thereto were added 3,6,9,12,15,18-hexaoxanonadecanoic acid (70 mg, 0.225 mmol), 1-ethyl-3-(3-dimethylaminopropyl)carbodiimide hydrochloride (72 mg, 0.38 mmol), and dimethylaminopyridine (1.8 mg, 0.015 mmol). This mixture was stirred at 25° C. for 29 hours. After the ordinary post-treatment, the reaction mixture was purified by thin-layer chromatography (developed with chloroform/methanol=20/1) to obtain Compound 24 (29 mg, yield 39%).

$^1$H NMR (CDCl$_3$, 270 MHz) δ ppm; 9.21 (dd, J=11.7, 16.6 Hz, 1H), 7.45 (s, 1H), 6.63 (d, J=11.5 Hz, 1H), 6.32 (t, J=11.5 Hz, 1H), 6.02 (d, J=16.6 Hz, 1H), 5.74 (br s, 2H), 5.59 (q, J=6.6 Hz, 1H), 5.55 (br s, 1H), 5.45 (br s, 2H), 5.07 (br s, 1H), 4.04 (d, J=17.8 Hz, 1H), 4.11 (s, 2H), 3.89 (br d, J=5.3 Hz, 2H), 3.7–3.5 (m, 20H), 3.38 (s, 3H), 2.5–1.6 (m, 4H), 2.32 (d, J=17.8 Hz, 1H), 1.88 (d, J=6.6 Hz, 3H), 1.79 (s, 3H), 1.69 (s, 3H), 1.45 (s, 9H)

FABMS m/z 990 (M+H)$^+$ calcd for $C_{43}H_{63}N_3O_{17}S_3$=989

Example 24

Synthesis of Compound 25

According to the method used in Example 23, Compound 25 (10 mg, yield 60%) was obtained from Compound F (13 mg, 0.015 mmol) obtained in Reference Example 6, dichloromethane (0.6 ml), 3,6,9,12,15,18-hexaoxanonadecanoic acid (14 mg, 0.045 mmol), 1-ethyl-3-(3-dimethylaminopropyl)carbodiimide hydrochloride (14 mg, 0.075 mmol), and dimethylaminopyridine (0.4 mg, 0.003 mmol).

$^1$H NMR (CDCl$_3$, 400 MHz) δ ppm; 9.21 (dd, J=11.5, 16.8 Hz, 1H), 7.44 (s, 1H), 6.63 (d, J=11.2 Hz, 1H), 6.32 (t, J=11.4 Hz, 1H), 6.03 (d, J=16.8 Hz, 1H), 5.75 (br s, 2H), 5.59 (q, J=6.6 Hz, 1H), 5.52 (br s, 1H), 5.40 (br s, 2H), 5.04 (br d, J=ca. 5 Hz, 1H), 4.20 (br s, 1H), 4.11 (s, 2H), 4.03 (d, J=17.8 Hz, 1H), 3.7–3.5 (m, 20H), 3.38 (s, 3H), 2.5–1.6 (m, 8H), 2.31 (d, J=17.8 Hz, 1H), 1.89 (d, J=6.6 Hz, 3H), 1.79 (s, 3H), 1.71 (s, 3H), 1.47 (s, 9H), 1.44 (s, 9H)

FABMS m/z 1140 (M+Na)$^+$ calcd for $C_{50}H_{75}N_3O_{17}S_3$= 1117

Example 25

Synthesis of Compound 26

In the same manner as in Example 1, Compound 26 (70 mg, yield 45%) was obtained from DC107 (80 mg, 0.16 mmol), 14-tert-butyldiphenylsilyloxy-3,6,9,12-tetraoxatetradecanoic acid (230 mg, 0.47 mmol), 1-ethyl-3-(3-dimethylaminopropyl)carbodiimide hydrochloride (90 mg, 0.47 mmol), and 4-dimethylaminopyridine (9.6 mg, 0.079 mmol).

$^1$H NMR (CDCl$_3$, 500 MHz) δ ppm; 8.69 (dd, J=16.6, 11.4 Hz, 1H), 7.70–7.34 (m, 10H), 7.27 (s, 1H), 6.63 (d, J=11.2 Hz, 1H), 6.62 (m, 1H), 6.36 (dd, J=11.4, 11.2 Hz, 1H), 6.03 (d, J=16.4 Hz, 1H), 5.88 (d, J=9.8 Hz, 1H), 5.76 (br d, J=9.8 Hz, 1H), 5.37 (dq, J=6.6, 6.6 Hz, 1H), 4.33 (br s, 1H), 4.09 (br s, 2H), 3.82–3.52 (m, 16H), 3.09 (d, J=15.4 Hz, 1H), 3.03 (d, J=15.4 Hz, 1H), 2.40–1.70 (m, 4H), 1.75 (s, 3H), 1.74 (d, J=6.6 Hz, 3H), 1.71 (d, J=1.0 Hz, 3H), 1.04 (s, 9H)

FABMS m/z 983 (M+H)$^+$

HRFABMS calcd for $C_{48}H_{63}N_2O_{12}SiS_3$ (M+H)$^+$ 983.3312, found 983.3334

Example 26

Synthesis of Compound 27

Compound 26 (70 mg, 0.071 mmol) obtained in Example 25 was dissolved in THF (4.0 ml). Thereto was added 3 N hydrochloric acid (1.0 ml). This mixture was stirred at 20° C. for 8 hours. After the ordinary post-treatment, the reaction product was purified by thin-layer chromatography (developed with chloroform/methanol=96/4) to obtain Compound 27 (15 mg, yield 28%).

$^1$H NMR (CDCl$_3$, 400 MHz) δ ppm; 8.63 (dd, J=16.6, 11.5 Hz, 1H), 7.28 (s, 1H), 6.66 (br d, J=6.4 Hz, 1H), (d, J=11.5 Hz, 1H), 6.35 (t, J=11.5 Hz, 1H), 6.04 (d, J=16.6 Hz, 1H), 5.91 (s, J=9.8 Hz, 1H), 5.76 (br d, J=9.8 Hz, 1H), 5.38 (dq, J=6.4, 6.6 Hz, 1H), 4.35 (br s, 1H), 4.12 (s, 2H), 3.73–3.66 (m, 16H), 3.11 (d, J=15.4 Hz, 1H), 3.00 (d, J=15.4 Hz, 1H), 2.73 (br s, 1H), 2.40–1.67 (m, 4H), 1.75 (d, J=6.6 Hz, 3H), 1.74 (s, 3H), 1.71 (d, J=1.0 Hz, 3H)

FABMS m/z 745 (M+H)$^+$

HRFABMS calcd for $C_{32}H_{45}N_2O_{12}S_3$ (M+H)$^+$ 745.2134, found 745.2160

Example 27

Synthesis of Compound 28

Compound G (100 mg, 0.106 mmol) obtained in Reference Example 7 was dissolved in dichloromethane (4.4 ml). Thereto were added 3,6,9-trioxadecanoic acid (95 mg, 0.53 mmol), 1-ethyl-3-(3-dimethylaminopropyl)carbodiimide hydrochloride (102 mg, 0.53 mmol), and dimethylaminopyridine (2.6 mg, 0.021 mmol). This mixture was stirred at room temperature for 17 hours. After the ordinary post-treatment, the reaction mixture was purified by silica gel column chromatography (eluted with chloroform/methanol=100/1) to obtain a crude reaction product (136 mg). This crude product was further purified by HPLC for fractionation (eluted with acetonitrile/water=50/50) to obtain Compound 28 (47 mg, yield 40%).

$^1$H NMR (CDCl$_3$, 270 MHz) δ ppm; 9.23 (dd, J=11.1, 16.8 Hz, 1H), 7.56 (br d, J=7.9 Hz, 1H), 7.44 (s, 1H), 6.62 (d, J=11.5 Hz, 1H), 6.32 (t, J=11.3 Hz, 1H), 6.03 (d, J=16.8 Hz, 1H), 5.77 (br d, J=ca. 9 Hz, 1H), 5.73 (br d, J=ca. 9 Hz, 1H), 5.59 (q, J=6.6 Hz, 1H), 5.48 (s, 1H), 5.39 (s, 2H), 4.64 (m, 1H), 4.58 (s, 1H), 4.33 (d, J=2.3 Hz, 1H), 4.17 (d, J=ca. 2 Hz, 1H), 4.13 (s, 2H), 4.11 (s, 2H), 4.03 (d, J=17.8 Hz, 1H), 3.75 (s, 3H), 3.7–3.5 (m, 8H), 3.35 (s, 3H), 2.6–1.7 (m, 8H), 2.30 (d, J=17.8 Hz, 1H), 1.88 (d, J=6.6 Hz, 3H), 1.79 (s, 3H), 1.71 (s, 3H), 1.53 (s, 3H), 1.52 (s, 3H), 1.44 (s, 3H), 1.32 (s, 3H)

FABMS m/z 1100 (M+H)$^+$ calcd for C$_{48}$H$_{65}$N$_3$O$_{20}$S$_3$=1099

Example 28

Synthesis of Compound 29

Compound H (100 mg, 0.119 mmol) obtained in Reference Example 8 was dissolved in dichloromethane (4.9 ml). Thereto were added 3,6,9-trioxadecanoic acid (106 mg, 0.595 mmol), 1-ethyl-3-(3-dimethylaminopropyl)carbodiimide hydrochloride (114 mg, 0.595 mmol), and dimethylaminopyridine (2.9 mg, 0.024 mmol). This mixture was stirred at room temperature for 18 hours. After the ordinary post-treatment, the reaction product was purified by silica gel chromatography (eluted with chloroform/methanol=100/1) to obtain Compound 29 (93 mg, yield 79%).

$^1$H NMR (CDCl$_3$, 270 MHz) δ ppm; 9.22 (dd, J=11.5, 16.8 Hz, 1H), 7.73 (br d, J=ca. 8 Hz, 1H), 7.43 (s, 1H), 6.62 (d, J=11.5 Hz, 1H), 6.32 (t, J=11.5 Hz, 1H), 6.03 (d, J=16.8 Hz, 1H), 5.75 (s, 2H), 5.58 (q, J=6.6 Hz, 1H), 5.50 (s, 1H), 5.39 (s, 2H), 4.72 (m, 1H), 4.11 (s, 2H), 4.03 (d, J=17.8 Hz, 1H), 4.0–3.5 (m, 12H), 3.76 (s, 3H), 3.34 (s, 3H), 2.5–1.6 (m, 8H), 2.32 (d, J=17.8 Hz, 1H), 1.88 (d, J=6.6 Hz, 3H), 1.79 (s, 3H), 1.71 (s, 3H), 1.48 (s, 6H), 0.99 (s, 3H)

FABMS m/z 1022 (M+Na)$^+$ calcd for C$_{44}$H$_{61}$N$_3$O$_{17}$S$_3$=999

Example 29

Synthesis of Compound 30

In the same manner as in Example 1, Compound 30 (21 mg, yield 63%) was obtained from Compound 8 (27 mg, 0.041 mmol), 3,6,9-trioxadecanoic acid (19 mg, 0.12 mmol), 1-ethyl-3-(3-dimethylaminopropyl)carbodiimide hydrochloride (24 mg, 0.12 mmol), and 4-dimethylaminopyridine (2.5 mg, 0.021 mmol).

$^1$H NMR (CDCl$_3$, 400 MHz) δ ppm; 8.63 (dd, J=16.6, 11.5 Hz, 1H), 7.29 (s, 1H), 6.65 (d, J=11.5 Hz, 1H), 6.60 (br d, J=6.6 Hz, 1H), 6.35 (t, J=11.5 Hz, 1H), 6.04 (d, J=16.6 Hz, 1H), 5.91 (d, J=9.8 Hz, 1H), 5.74 (br d, J=9.8 Hz, 1H), 5.38 (dq, J=6.6, 6.8 Hz, 1H), 4.30–4.24 (m, 3H), 4.16 (s, 2H), 4.11 (s, 2H), 3.75–3.52 (m, 14H), 3.37 (s, 3H), 3.12 (d, J=15.4 Hz, 1H), 2.99 (d, J=15.4 Hz, 1H), 2.42–1.67 (m, 4H), 1.74 (d, J=6.8 Hz, 3H), 1.73 (s, 3H), 1.71 (d, J=1.0 Hz, 3H)

FABMS m/z 817 (M+H)$^+$

HRFABMS calcd for C$_{35}$H$_{49}$N$_2$O$_4$S$_3$ (M+H)$^+$ 817.2346, found 817.2355

Example 30

Synthesis of Compound 31

In the same manner as in Example 1, Compound 31 (24 mg, yield 82%) was obtained from Compound 8 (25 mg, 0.038 mmol), 3,6-dioxaheptanoic acid (13 mg, 0.11 mmol), 1-ethyl-3-(3-dimethylaminopropyl)carbodiimide hydrochloride (22 mg, 0.11 mmol), and 4-dimethylaminopyridine (2.3 mg, 0.019 mmol).

$^1$H NMR (CDCl$_3$, 400 MHz) δ ppm; 8.63 (dd, J=16.6, 11.5 Hz, 1H), 7.29 (s, 1H), 6.65 (d, J=11.5 Hz, 1H), 6.59 (d, J=6.6 Hz, 1H), 6.35 (t, J=11.5 Hz, 1H), 6.04 (d, J=16.6 Hz, 1H), 5.91 (d, J=9.8 Hz, 1H), 5.74 (br d, J=9.8 Hz, 1H), 5.38 (dq, J=6.6, 6.6 Hz, 1H), 4.30–4.22 (m, 3H), 4.16 (s, 2H), 4.11 (s, 2H), 3.74–3.56 (m, 10H), 3.38 (s, 3H), 3.12 (d, J=15.6 Hz, 1H), 2.99 (d, J=15.6 Hz, 1H), 2.42–1.68 (m, 4H), 1.76 (d, J=6.6 Hz, 3H), 1.73 (s, 3H), 1.71 (d, J=1.0 Hz, 3H)

FABMS m/z 773 (M+H)$^+$

HRFABMS calcd for C$_{33}$H$_{45}$N$_2$O$_{13}$S$_3$ (M+H)$^+$ 773.2084, found 773.2077

Example 31

Synthesis of Compound 32

In the same manner as in Example 1, Compound 32 (81 mg, yield 49%) was obtained from DC107 (95 mg, 0.19 mmol), 6-tert-butyldiphenylsilyloxy-3-oxahexanoic acid (208 mg, 0.56 mmol), 1-ethyl-3-(3-dimethylaminopropyl)carbodiimide hydrochloride (107 mg, 0.56 mmol), and 4-dimethylaminopyridine (12 mg, 0.095 mmol).

FABMS m/z 865 (M+H)$^+$ calcd for C$_{43}$H$_{52}$N$_2$O$_9$S$_3$Si=864

Example 32

Synthesis of Compound 33

Compound 32 (81 mg, 0.094 mmol) obtained in Example 31 was dissolved in THF (12 ml). Thereto was added 10% aqueous perchloric acid solution (3.0 ml). This mixture was stirred at 20° C. for 5 hours. After the ordinary post-treatment, the reaction product was purified by thin-layer chromatography (developed with chloroform/methanol=95/5) to obtain Compound 33 (43 mg, yield 73%).

$^1$H NMR (CDCl$_3$, 400 MHz) δ ppm; 8.58 (dd, J=16.6, 11.5 Hz, 1H), 7.28 (s, 1H), 6.79 (br d, J=6.6 Hz, 1H), 6.65 (d, J=11.5 Hz, 1H), 6.35 (t, J=11.5 Hz, 1H), 6.04 (d, J=16.6 Hz, 1H), 5.93 (d, J=9.5 Hz, 1H), 5.76 (br d, J=9.5 Hz, 1H), 5.40 (dq, J=6.6, 6.6 Hz, 1H), 4.08 (br s, 1H), 4.07 (s, 2H), 3.76–3.59 (m, 4H), 3.16 (d, J=15.6 Hz, 1H), 2.99 (d, J=15.6 Hz, 1H), 2.60 (br s, 1H), 2.43–1.65 (m, 6H), 1.75 (d, J=6.6 Hz, 3H), 1.70 (s, 3H), 1.70 (s, 3H)

FABMS m/z 627 (M+H)$^+$

HRFABMS calcd for C$_{27}$H$_{35}$N$_2$O$_9$S$_3$ (M+H)$^+$ 627.1505, found 627.1528

Example 33

Synthesis of Compound 34

In the same manner as in Example 1, Compound 34 (92 mg, yield 62%) was obtained from DC107 (88 mg, 0.17 mmol), 7-tert-butyldiphenylsilyloxy-3-oxaheptanoic acid (200 mg, 0.52 mmol), 1-ethyl-3-(3-dimethylaminopropyl)carbodiimide hydrochloride (99.7 mg, 0.52 mmol), and 4-dimethylaminopyridine (10 mg, 0.085 mmol).

FABMS m/z 878 (M+H)$^+$ calcd for C$_{44}$H$_{54}$N$_2$O$_9$S$_3$Si=877

Example 34

Synthesis of Compound 35

Compound 34 (92 mg, 0.105 mmol) obtained in Example 33 was dissolved in THF (10 ml). Thereto was added 10% aqueous perchloric acid solution (3.0 ml). This mixture was stirred at 20° C. for 4 hours. After the ordinary post-treatment, the reaction product was purified by thin-layer chromatography (developed with chloroform/methanol=95/5) to obtain Compound 35 (52 mg, yield 73%).

$^1$H NMR (CDCl$_3$, 400 MHz) δ ppm; 8.62 (dd, J=16.6, 11.5 Hz, 1H), 7.28 (s, 1H), 6.86 (br d, J=6.6 Hz, 1H), 6.64 (d, J=11.5 Hz, 1H), 6.34 (t, J=11.5 Hz, 1H), 6.03 (d, J=16.6 Hz, 1H), 5.91 (d, J=9.5 Hz, 1H), 5.78 (br d, J=9.5 Hz, 1H), 5.39 (dq, J=6.6, 6.6 Hz, 1H), 4.19 (br s, 1H), 4.06 (s, 2H), 3.63–3.45 (m, 4H), 3.13 (d, J=15.6 Hz, 1H), 3.02 (d, J=15.6 Hz, 1H), 2.32–1.53 (m, 9H), 1.74 (d, J=6.6 Hz, 3H), 1.72 (s, 3H), 1.71 (d, J=1.0 Hz, 3H)

FABMS m/z 641 (M+H)$^+$

HRFABMS calcd for C$_{28}$H$_{37}$N$_2$O$_9$S$_3$ (M+H)$^+$ 641.1661, found 641.1665

Example 35

Synthesis of Compound 36

In the same manner as in Example 1, Compound 36 (10 mg, yield 8%) was obtained from DC107 (96 mg, 0.19 mmol), 4,7,10-trioxaundecanoic acid (290 mg, 1.51 mmol), 1-ethyl-3-(3-dimethylaminopropyl)carbodiimide hydrochloride (290 mg, 1.51 mmol), and 4-dimethylaminopyridine (12 mg, 0.40 mmol).

$^1$H NMR (CDCl$_3$, 400 MHz) δ ppm; 8.84 (dd, J=16.6, 11.5 Hz, 1H), 7.29 (s, 1H), 6.76 (br d, J=6.6 Hz, 1H), 6.63 (d, J=11.5 Hz, 1H), 6.33 (t, J=11.5 Hz, 1H), 6.00 (d, J=16.6 Hz, 1H), 5.33–5.24 (m, 2H), 5.35 (dq, J=6.6, 6.6 Hz, 1H), 4.53 (br s, 1H), 3.68–3.48 (m, 10H), 3.36 (s, 3H), 3.08 (d, J=15.4 Hz, 1H), 3.03 (d, J=15.4 Hz, 1H), 2.62–2.47 (m, 2H), 2.38–1.75 (m, 4H), 1.78 (s, 3H), 1.76 (d, J=6.6 Hz, 3H), 1.73 (s, 3H)

FABMS m/z 685 (M+H)$^+$

HRFABMS calcd for C$_{30}$H$_{41}$N$_2$O$_{10}$S$_3$ (M+H)$^+$ 685.1923, found 685.1904

Example 36

Synthesis of Compound 37

In the same manner as in Example 1, Compound 37 (170 mg, yield 62%) was obtained from Compound A (157 mg, 0.25 mmol) obtained in Reference Example 1, 14-tert-butyldiphenylsilyloxy-3,6,9,12-tetraoxatetradecanoic acid (370 mg, 0.76 mmol), 1-ethyl-3-(3-dimethylaminopropyl)carbodiimide hydrochloride (144 mg, 0.76 mmol), and 4-dimethylaminopyridine (15 mg, 0.13 mmol).

FABMS m/z 1095 (M+H)$^+$ calcd for C$_{53}$H$_{66}$N$_2$O$_{15}$S$_3$Si= 1094

Example 37

Synthesis of Compound 38

Compound 37 (170 mg, 0.155 mmol) obtained in Example 36 was dissolved in THF (12 ml). Thereto was added 10% aqueous perchloric acid solution (4.0 ml). This mixture was stirred at 20° C. for 5 hours. After the ordinary post-treatment, the reaction product was purified by thin-layer chromatography (developed with chloroform/methanol=95/5) to obtain Compound 38 (70 mg, yield 53%).

$^1$H NMR (CDCl$_3$, 400 MHz) δ ppm; 9.15 (ddd, J=16.6, 11.5, 1.0 Hz, 1H), 7.42 (s, 1H), 6.62 (d, J=11.5 Hz, 1H), 6.31 (t, J=11.5 Hz, 1H), 6.03 (d, J=16.6 Hz, 1H), 5.76 (br s, 2H), 5.57 (q, J=6.6 Hz, 1H), 5.45 (br s, 1H), 4.11 (br s, 2H), 4.03 (d, J=17.8 Hz, 1H), 3.77 (br s, 2H), 3.73–3.57 (m, 16H), 2.56–1.45 (m, 5H), 2.28 (d, J=17.8 Hz, 1H), 2.14 (s, 3H), 1.89 (d, J=6.6 Hz, 3H), 1.79 (s, 3H), 1.70 (s, 3H)

FABMS m/z 857 (M+H)$^+$

HRFABMS calcd for C$_{37}$H$_{49}$N$_2$O$_{15}$S$_3$ (M+H)$^+$ 857.2295, found 857.2283

Example 38

Synthesis of Compound 39

In the same manner as in Example 1, Compound 39 (18 mg, yield 66%) was obtained from Compound 38 (23 mg, 0.027 mmol) obtained in Example 37, 3,6,9-trioxadecanoic acid (14 mg, 0.081 mmol), 1-ethyl-3-(3-dimethylaminopropyl)carbodiimide hydrochloride (16 mg, 0.081 mmol), and 4-dimethylaminopyridine (1.6 mg, 0.014 mmol).

$^1$H NMR (CDCl$_3$, 400 MHz) δ ppm; 9.16 (ddd, J=16.6, 11.5, 1.0 Hz, 1H), 7.43 (s, 1H), 6.62 (d, J=11.5 Hz, 1H), 6.32 (t, J=11.5 Hz, 1H), 6.03 (d, J=16.6 Hz, 1H), 5.73 (br s, 2H), 5.57 (q, J=6.6 Hz, 1H), 5.42 (br s, 1H), 4.33–4.27 (m, 2H), 4.18 (br s, 2H), 4.11 (br s, 2H), 4.03 (d, J=17.8 Hz, 1H), 3.78 (br s, 2H), 3.77–3.53 (m, 22H), 3.59 (s, 3H), 2.48–1.45 (m, 4H), 2.28 (d, J=17.8 Hz, 1H), 2.14 (s, 3H), 1.89 (d, J=6.6 Hz, 3H), 1.79 (s, 3H), 1.71 (s, 3H)

FABMS m/z 1017 (M+H)$^+$

HRFABMS calcd for C$_{44}$H$_{61}$N$_2$O$_{19}$S$_3$ (M+H)$^+$ 1017.3030, found 1017.3047

Example 39

Synthesis of Compound 40

Compound 28 (30 mg, 0.027 mmol) obtained in Example 27 was dissolved in THF (4 ml). Thereto was added hydrochloric acid (1 M, 4 ml). This mixture was stirred at room temperature for 3 hours. The reaction mixture was subjected to the ordinary post-treatment, and the resultant residue was purified by thin-layer chromatography (silica gel; developed with chloroform/methanol=9/1) to obtain Compound 40 (18 mg, yield 94%).

$^1$H NMR (CDCl$_3$, 270 MHz) δ ppm; 9.21 (dd, J11.7, 16.7 Hz, 1H), 7.57 (br d, J=8.6 Hz, 1H), 7.44 (s, 1H), 6.63 (d, J=11.5 Hz, 1H), 6.32 (t, J=11.6 Hz, 1H), 6.03 (d, J=16.6 Hz, 1H), 5.75 (s, 2H), 5.58 (q, J=6.6 Hz, 1H), 5.51 (br s, 1H), 5.43 (d, J=ca. 11 Hz, 1H), 5.37 (d, J=ca. 11 Hz, 1H), 4.63 (m, 1H), 4.53 (s, 1H), 4.43 (m, 1H), 4.30 (m, 1H), 4.2–3.9 (2H, overlapped with other peaks), 4.11 (s, 2H), 4.03 (br s, 2H), 3.8–3.5 (m, 8H) 3.77 (s, 3H), 3.35 (s, 3H), 3.0 (br s, 1H), 2.5–1.4 (m, 8H), 2.39 (d, J=17.5 Hz, 1H), 1.88 (d, J=6.6 Hz, 3H), 1.68 (s, 3H), 1.79 (s, 3H), 1.57 (s, 3H), 1.48 (s, 3H)

FABMS m/z 1060 (M+H)$^+$ calcd for C$_{45}$H$_{61}$N$_3$O$_{20}$S$_3$= 1059

Example 40

Synthesis of Compound 41

Compound 29 (63 mg, 0.063 mmol) obtained in Example 28 was dissolved in THF (9 ml). Thereto was added 1 N hydrochloric acid (9 ml). This mixture was stirred at room temperature for 75 minutes. The reaction mixture was subjected to the ordinary post-treatment, and the resultant residue was purified by thin-layer chromatography (silica gel; developed with chloroform/methanol=9/1) to obtain Compound 41 (36 mg, yield 59%).

$^1$H NMR (CDCl$_3$, 270 MHz) δ ppm; 9.21 (dd, J=11.6, 16.8 Hz, 1H), 7.60 (br d, J=ca. 8 Hz, 1H), 7.44 (s, 1H), 6.62

(d, J=11.5 Hz, 1H), 6.32 (t, J=11.5 Hz, 1H), 6.03 (d, J=16.8 Hz, 1H), 5.75 (s, 2H), 5.64 (br s, 1H-), 5.57 (q, J=6.6 Hz, 1H), 5.39 (s, 2H), 4.60 (m, 1H), 4.12 (s, 2H), 4.08 (d, J=ca. 18 Hz, 1H), 3.8–3.4 (m, 14H), 3.76 (s, 3H), 3.34 (s, 3H), 2.6–1.4 (m, 8H), 2.33 (d, J=17.8 Hz, 1H), 1.88 (d, J=6.6 Hz, 3H), 1.79 (s, 3H), 1.67 (s, 3H), 1.10 (s, 3H)

FABMS m/z 982 (M+Na)$^+$ calcd for $C_{41}H_{57}N_3O_{17}S_3$=959

Example 41

Synthesis of Compound 42

Compound I (21 mg, 0.027 mmol) obtained in Reference Example 9 was dissolved in dichloromethane (1.0 mL). Thereto were added 3,6,9-trioxadecanoic acid (27 mg, 0.15 mmol), 1-ethyl-3-(3-dimethylaminopropyl)carbodiimide hydrochloride (21 mg, 0.11 mmol), and dimethylaminopyridine (0.5 mg). This mixture was stirred at room temperature for 6 hours. The reaction mixture was subjected to the ordinary post-treatment, and the resultant residue was purified by thin-layer chromatography (silica gel; developed with chloroform/methanol=20/1) to obtain Compound 42 (19 mg, yield 75%).

$^1$H NMR (CDCl$_3$, 270 MHz) δ ppm; 9.21 (dd, J=11.4, 16.8 Hz, 1H), 7.43 (s, 1H), 7.14 (br s, 1H), 6.62 (d, J=11.4 Hz, 1H), 6.31 (t, J=11.4 Hz, 1H), 6.02 (d, J=16.8 Hz, 1H), 5.75 (br s, 2H), 5.58 (q, J=6.4 Hz, 1H), 5.57 (s, 1H), 5.40 (s, 2H), 4.11 (s, 2H), 4.03 (d, J=17.8 Hz, 1H), 3.89 (d, J=12.4 Hz, 2H), 3.75 (d, J=12.4 Hz, 2H), 3.8–3.5 (m, 8H), 3.4–3.2 (m, 2H), 3.34 (s, 3H), 2.5–1.4 (m, 8H), 2.32 (d, J=17.8 Hz, 1H), 1.88 (d, J=6.4 Hz, 3H), 1.73 (s, 3H), 1.69 (s, 3H), 1.47 (s, 3H), 1.41 (s, 3H) 0.99 (s, 3H)

FABMS m/z 942 (M+H)$^+$ calcd for $C_{42}H_{59}N_3O_{15}S_3$=941

Example 42

Synthesis of Compound 43

Compound I (166 mg, 0.119 mmol) obtained in Reference Example 9 was dissolved in dichloromethane (10 mL). Thereto were added 3,6,9-trioxadecanoic acid (180 mg, 1.01 mmol), 1-ethyl-3-(3-dimethylaminopropyl)carbodiimide hydrochloride (200 mg, 1.04 mmol), and dimethylaminopyridine (5 mg, 0.04 mmol). This mixture was stirred at room temperature for 4.5 hours. The reaction mixture was subjected to the ordinary post-treatment, and the resultant residue was dissolved in tetrahydrofuran (20 mL). Hydrochloric acid (1 M, 20 mL) was added to the solution, and this mixture was stirred at room temperature for 1 hour. The reaction mixture was subjected to the ordinary post-treatment, and the resultant residue was purified by HPLC for fractionation (ODS; eluted with acetonitrile/water=35/65) to obtain Compound 43 (64 mg, yield 34%).

$^1$H NMR (CDCl$_3$, 270 MHz) δ ppm; (major peaks) 9.22 (dd, J=11.4, 16.6 Hz, 1H), 7.44 (s, 1H), 7.20 (br t, J=5.7 Hz, 1H), 6.63 (d, J=11.4 Hz, 1H), 6.32 (t, J=11.4 Hz, 1H), 6.02 (d, J=16.6 Hz, 1H), 5.74 (br s, 2H), 5.70 (s, 1H), 5.57 (q, J=6.9 Hz, 1H), 5.38 (s, 2H), 4.11 (s, 2H), 4.07 (d, J=17.8 Hz, 1H), 3.8–3.5 (m, 12H), 3.34 (s, 3H), 3.28 (m, 2H), 2.6–1.4 (m, 8H), 2.34 (d, J=17.8 Hz, 1H), 1.88 (d, J=6.9 Hz, 3H), 1.79 (s, 3H), 1.65 (s, 3H), 1.06 (s, 3H)

FABMS m/z 902 (M+H)$^+$ calcd for $C_{39}H_{55}N_3O_{15}S_3$=901

Example 43

Synthesis of Compound 44

Compound J (20 mg, 0.29 mmol) obtained in Reference Example 10 was dissolved in dichloromethane (1.5 mL). Thereto were added 3,6,9-trioxadecanoic acid (26 mg, 0.14 mmol), 1-ethyl-3-(3-dimethylaminopropyl)carbodiimide hydrochloride (28 mg, 0.14 mmol), and dimethylaminopyridine (0.7 mg, 0.006 mmol). This mixture was stirred at room temperature for 2.5 hours. The reaction mixture was subjected to the ordinary post-treatment, and the resultant residue was purified by thin-layer chromatography (silica gel; developed with chloroform/methanol=20/1) to obtain Compound 44 (12 mg, yield 50%).

$^1$H NMR (CDCl$_3$, 270 MHz) δ ppm; 9.21 (dd, J=11.5, 16.7 Hz, 1H), 7.42 (s, 1H), 6.62 (d, J=11.5 Hz, 1H), 6.31 (t, J=11.5 Hz, 1H), 6.02 (d, J=16.7 Hz, 1H), 5.84 (s, 1H), 5.75 (br s, 2H), 5.57 (q, J=6.6 Hz, 1H), 5.44 (s, 2H), 4.4–4.2 (m, 2H), 4.11 (s, 2H), 4.03 (d, J=17.8 Hz, 1H), 3.7–3.3 (m, 12H), 3.34 (s, 3H), 2.6–1.6 (m, 8H), 2.34 (d, J=17.8 Hz, 1H), 1.88 (d, J=6.6 Hz, 3H), 1.79 (s, 3H), 1.68 (s, 3H)

FABMS m/z 878 (M+Na)$^+$ calcd for $C_{37}H_{49}N_3O_{14}S_3$=855

Example 44

Synthesis of Compound 45

Compound K (30 mg, 0.044 mmol) obtained in Reference Example 11 was dissolved in dichloromethane (2.0 mL). Thereto were added 3,6,9-trioxadecanoic acid (39 mg, 0.22 mmol), 1-ethyl-3-(3-dimethylaminopropyl)carbodiimide hydrochloride (42 mg, 0.22 mmol), and dimethylaminopyridine (1.1 mg, 0.009 mmol). This mixture was stirred at room temperature for 5.5 hours. The reaction mixture was subjected to the ordinary post-treatment, and the resultant residue was purified by silica gel chromatography (eluted with chloroform/methanol=20/1) to obtain Compound 45 (22 mg, yield 60%).

$^1$H NMR (CDCl$_3$, 270 MHz) δ ppm; 9.23 (dd, J=11.5, 16.7 Hz, 1H), 7.44 (s, 1H), 6.63 (d, J=11.2 Hz, 1H), 6.32 (t, J=11.4 Hz, 1H), 6.03 (d, J=16.7 Hz, 1H), 5.77 (br d, J=ca. 9 Hz, 1H), 5.72 (br d, J=ca. 9 Hz, 1H), 5.59 (q, J=6.6 Hz, 1H), 5.55 (s, 1H), 5.47 (d, J=11.2 Hz, 1H), 5.42 (d, J=11.2 Hz, 1H), 4.34 (m, 2H), 4.11 (s, 2H), 4.03 (d, J=17.8 Hz, 1H), 3.8–3.5 (m, 14H), 3.38 (s, 3H), 3.35 (s, 3H), 2.5–1.8 (m, 4H), 2.33 (d, J=17.8 Hz, 1H), 1.88 (d, J=6.6 Hz, 3H), 1.79 (s, 3H), 1.71 (s, 3H)

FABMS m/z 847 (M+H)$^+$ calcd for $C_{36}H_{50}N_2O_{15}S_3$=846

Example 45

Synthesis of Compound 46

Compound L (100 mg, 0.124 mmol) obtained in Reference Example 12 was dissolved in dichloromethane (6 mL). Thereto were added 3,6,9-trioxadecanoic acid (111 mg, 0.62 mmol), 1-ethyl-3-(3-dimethylaminopropyl)carbodiimide hydrochloride (119 mg, 0.62 mmol), and dimethylaminopyridine (3.0 mg, 0.025 mmol). This mixture was stirred at room temperature for 4.5 hours. The reaction mixture was subjected to the ordinary post-treatment, and the resultant residue was purified by silica gel chromatography (eluted with chloroform/methanol=20/1) to quantitatively obtain Compound 46.

$^1$H NMR (CDCl$_3$, 270 MHz) δ ppm; (major peaks) 9.22 (dd, J=11.5, 16.8 Hz, 1H), 7.43 (s, 1H), 7.36 (m, 2H), 7.07 (m, 2H), 6.62 (d, J=11.9 Hz, 1H), 6.32 (t, J=11.7 Hz, 1H), 6.02 (d, J=16.8 Hz, 1H), 5.74 (br s, 2H), 5.58 (q, J=6.6 Hz, 1H), 5.45 (s, 2H), 4.49 (s, 2H), 4.15 (s, 2H), 4.11 (s, 2H), 4.03 (d, J=17.8 Hz, 1H), 3.80 (s, 3H), 3.8–3.5 (m, 16H), 3.38 (s, 3H), 2.5–1.6 (m, 5H), 1.88 (d, J=6.6 Hz, 3H), 1.78 (s, 3H), 1.70 (s, 3H)

Example 46

Synthesis of Compound 47

A whole amount of Compound 46 synthesized in the same manner as in Example 45 from Compound L (100 mg, 0.124 mmol) obtained in Reference Example 12 was dissolved in chloroform (9.5 mL) and water (0.5 mL). Thereto was added DDQ (34 mg). This mixture was stirred at room temperature for 1.5 hours. The reaction mixture was subjected to the ordinary post-treatment, and the resultant residue was purified by silica gel chromatography (eluted with chloroform/methanol=50/1) and then by thin-layer chromatography (silica gel; developed with chloroform/methanol=9/1) to obtain Compound 47 (18 mg, yield 17%).

$^1$H NMR (CDCl$_3$, 270 MHz) δ ppm; (major peaks) 9.20 (dd, J=11.4, 16.8 Hz, 1H), 7.44 (s, 1H), 6.62 (d, J=11.4 Hz, 1H), 6.32 (t, J=11.4 Hz, 1H), 6.02 (d, J=16.8 Hz, 1H), 5.75 (s, 2H), 5.58 (q, J=6.7 Hz, 1H), 5.53 (br s, 1H), 5.47 (s, 2H), 4.16 (s, 2H), 4.11 (s, 2H), 4.02 (d, J=17.8 Hz, 1H), 3.8–3.5 (m, 14H), 3.50 (m, 2H), 3.34 (s, 3H), 2.6–1.6 (m, 4H), 2.31 (d, J=17.8 Hz, 1H), 1.88 (d, J=6.7 Hz, 3H), 1.79 (s, 3H), 1.70 (s, 3H)

FABMS m/z 847 (M+H)$^+$ calcd for C$_{36}$H$_{50}$N$_2$O$_{15}$S$_3$=846

Example 47

Synthesis of Compound 48

In dichloromethane (2.5 mL) were dissolved DC107 (7.4 mg, 0.015 mmol) and 2,3,4,6-tetrabenzylglucose-1-O-trichloroacetimidate (50 mg, 0.073 mmol). Thereto was added a boron trifluoride/diethyl ether complex (1.8 μL, 0.015 mmol) at 0° C. This mixture was stirred for 60 minutes. After the ordinary post-treatment, the reaction product was purified by thin-layer chromatography (developed with ether/methanol=95/5) to obtain Compound 48 (5.0 mg, yield 32%). This Compound 48 was an approximately 2:1 mixture of diastereomers.

$^1$H NMR (CDCl$_3$, 500 MHz) δ ppm; major isomer 8.74 (dd, J=16.5, 11.3 Hz, 1H), 7.36–7.07 (m, 21H), 6.67 (br d, J=6.4 Hz, 1H), 6.53 (d, J=11.6 Hz, 1H), 6.28 (dd, J=11.6, 11.3 Hz, 1H), 6.08 (d, J=16.5 Hz, 1H), 5.86 (br d, J=9.8 Hz, 1H), 5.22 (dq, J=6.7, 6.4 Hz, 1H), 5.15 (d, J=9.8 Hz, 1H), 4.98–4.36 (m, 10H), 3.75–3.33 (m, 6H), 3.20 (d, J=15.3 Hz, 1H), 2.96 (d, J=15.3 Hz, 1H), 2.42–1.80 (m, 4H), 1.82 (s, 3H), 1.64 (s, 3H), 1.63 (d, J=6.4 Hz, 3H) minor isomer; 9.10 (dd, J=16.5, 11.3 Hz, 1H), 7.36–7.07 (m, 21H), 6.97 (br d, J=6.4 Hz, 1H), 6.48 (d, J=11.6 Hz, 1H), 6.21 (dd, J=11.6, 11.3 Hz, 1H), 6.01 (d, J=16.5 Hz, 1H), 5.95 (br d, J=9.8 Hz, 1H), 5.28 (dq, J=6.7, 6.4 Hz, 1H), 5.05 (d, J=9.8 Hz, 1H), 4.90–4.36 (m, 10H), 3.75–3.33 (m, 6H), 3.21 (d, J=15.3 Hz, 1H), 2.93 (d, J=15.3 Hz, 1H), 2.42–1.80 (m, 4H), 1.82 (s, 3H), 1.77 (d, J=6.7 Hz, 3H), 1.64 (s, 3H)

FABMS m/z 1032 (M+H)$^+$

Example 48

Synthesis of Compound 49

In dichloromethane (2.0 mL) were dissolved DC107 (19 mg, 0.037 mmol) and 2,3,4,6-tetraacetylglucose-1-O-trichloroacetimidate (90 mg, 0.18 mmol). Thereto was added a boron trifluoride/diethyl ether complex (10 μL, 0.081 mmol) at 0° C. This mixture was stirred for 60 minutes. After the ordinary post-treatment, the reaction product was purified by thin-layer chromatography (developed with ether/methanol=95/5) to obtain Compound 49 (10 mg, yield 33%).

$^1$H NMR (CDCl$_3$, 500 MHz) δ ppm; 8.78 (dd, J=16.8, 11.6 Hz, 1H), 7.27 (s, 1H), 7.03 (br d, J=6.4 Hz, 1H), 6.60 (d, J=11.6 Hz, 1H), 6.32 (dd, J=11.6, 11.6 Hz, 1H), 5.98 (d, J=16.5 Hz, 1H), 5.89 (br d, J=9.2 Hz, 1H), 5.28 (dq, J=6.7, 6.4 Hz, 1H), 5.13 (dd, J=9.5, 9.2 Hz, 1H), 4.96 (dd, J=10.1, 9.5 Hz, 1H), 4.89 (br, 1H), 4.88 (dd, J=9.2, 1.2 Hz, 1H), 4.78 (dd, J=9.2, 7.9 Hz, 1H), 4.75 (d, J=7.9 Hz, 1H), 4.11 (dd, J=12.2, 6.1 Hz, 1H), 4.01 (dd, J=12.2, 2.4 Hz, 1H), 3.67 (ddd, J=10.1, 6.1, 2.4 Hz, 1H), 3.27 (d, J=15.1 Hz, 1H), 2.92 (d, J=15.1 Hz, 1H), 2.42–1.75 (m, 4H), 2.09 (s, 3H), 2.00 (s, 3H), 1.94 (s, 3H), 1.87 (s, 3H), 1.78 (s, 3H), 1.71 (d, J=1.2 Hz, 3H), 1.68 (d, J=6.7 Hz, 3H)

FABMS m/z 841 (M+H)$^+$

HRFABMS calcd for C$_{36}$H$_{45}$N$_2$O$_{15}$S$_3$ (M+H)$^+$ 841.1982, found 841.1983

Example 49

Synthesis of Compound 50

In dichloromethane (2.0 mL) were dissolved DC107 (15 mg, 0.029 mmol) and 3,4,6-tri-O-acetyl-D-glucal (60 mg, 0.22 mmol). Thereto was added camphorsulfonic acid (5.0 mg, 0.081 mmol). This mixture was stirred at 25° C. for 24 hours. After the ordinary post-treatment, the reaction product was purified by thin-layer chromatography (developed with ether/methanol=95/5) to obtain Compound 50 (4.0 mg, yield 19%).

IR (KBr) 3450, 2932, 1743, 1641, 1610, 1542, 1438, 1371, 1236, 1099, 1034, 888, 808 cm$^{-1}$ $^1$H NMR (CDCl$_3$, 500 MHz) δ ppm; 9.24 (dd, J=16.5, 11.3 Hz, 1H), 7.27 (s, 1H), 6.79 (br d, J=6.6 Hz, 1H), 6.66 (d, J=11.5 Hz, 1H), 6.38 (dd, J=11.5, 11.3 Hz, 1H), 6.04 (d, J=16.5 Hz, 1H), 5.84 (br d, J=9.8 Hz, 1H), 5.73 (br d, J=10.0 Hz, 1H), 5.54 (ddd, J=10.0, 2.7, 2.0 Hz, 1H), 5.29 (dq, J=6.6, 6.6 Hz, 1H), 5.23 (ddd, J=9.8, 1.5, 1.5 Hz, 1H), 5.17 (dd, J=9.8, 1.0 Hz, 1H), 4.99 (m, 2H), 4.22 (dd, J=12.2, 5.5 Hz, 1H), 4.11 (dd, J=12.2, 5.5 Hz, 1H), 3.96 (ddd, J=9.8, 5.5, 2.7 Hz, 1H), 3.18 (d, J=14.9 Hz, 1H), 2.93 (d, J=14.9 Hz, 1H), 2.37–1.70 (m, 4H), 2.08 (s, 3H) 2.06 (s, 3H), 1.87 (s, 3H), 1.76 (d, J=1.0 Hz, 3H), 1.72 (d, J=6.6 Hz, 3H)

FABMS m/z 723 (M+H)$^+$

Example 50

Synthesis of Compound 51

In dichloromethane (3.0 mL) were dissolved DC107 (58 mg, 0.11 mmol) and tri-O-tert-butyldimethylsilyl-D-glucal (277 mg, 0.55 mmol). Thereto was added camphorsulfonic acid (25 mg, 0.11 mmol). This mixture was stirred at 25° C. for 5 hours. After the ordinary post-treatment, the reaction product was purified by thin-layer chromatography (developed with chloroform/methanol=97/3) to obtain Compound 51 (30 mg, yield 26%).

FABMS m/z 999 (M+H)$^+$

Example 51

Synthesis of Compound 52

Compound 51 (30 mg, 0.024 mmol) obtained in Example 50 was dissolved in methanol (3.0 mL). Thereto was added 3 N hydrochloric acid (0.05 mL). This mixture was stirred at 25° C. for 5 hours. After the ordinary post-treatment, the reaction product was purified by thin-layer chromatography (developed with chloroform/methanol=95/5) to obtain Compound 52 (8.0 mg, yield 41%).

IR (KBr) 3420, 2932, 1711, 1641, 1611, 1533, 1449, 1375, 1256, 1195, 1096, 1061, 1017, 766 cm$^{-1}$ $^1$H NMR (CDCl$_3$+CD$_3$OD, 400 MHz) δ ppm; 8.98 (dd, J=16.6, 11.2 Hz, 1H), 7.51 (s, 1H), 6.71 (d, J=11.5 Hz, 1H), 6.33 (dd, J=11.5, 11.2 Hz, 1H), 5.98 (d, J=16.6 Hz, 1H), 5.86 (br d, J=9.3 Hz, 1H), 5.31 (q, J=6.6 Hz, 1H), 5.18 (d, J=9.3 Hz, 1H), 4.81 (br d, J=3.2 Hz, 1H), 3.83 (dd, J=12.0, 2.4 Hz, 1H), 3.82–3.73 (m, 1H), 3.67 (dd, J=12.0, 5.6 Hz, 1H), 3.54–3.46 (m, 1H), 3.20 (dd, J=9.5, 9.2 Hz, 1H), 3.19 (d, J=15.9 Hz, 1H), 2.95 (d, J=15.9 Hz, 1H), 2.46–1.50 (m, 6H), 1.76 (d, J=6.6 Hz, 3H), 1.69 (d, J=1.0 Hz, 3H), 1.65 (s, 3H)

FABMS m/z 657 (M+H)$^+$

Example 52

Syntheses of Compound 53 and Compound 54

To Compound 52 (14 mg, 0.021 mmol) obtained in Example 51 were added dichloromethane (1.0 mL), pyridine (0.1 mL), and acetic anhydride (0.05 mL). This mixture was stirred at 25° C. for 2.5 hours. After the ordinary post-treatment, the reaction product was purified by thin-layer chromatography (developed with chloroform/methanol=95/5) to obtain Compound 53 (1.5 mg, yield 10%) and Compound 54 (5.6 mg, yield 36%).

Compound 53

IR (KBr) 3430, 2930, 1741, 1642, 1612, 1528, 1449, 1369, 1232, 1123, 1095, 1043 cm$^{-1}$ $^1$H NMR (CDCl$_3$, 400 MHz) δ ppm; 9.24 (dd, J=16.7, 11.7 Hz, 1H), 7.29 (s, 1H), 6.79 (br d, J=6.3 Hz, 1H), 6.65 (d, J=11.5 Hz, 1H), 6.34 (dd, J=11.7, 11.5 Hz, 1H), 6.01 (d, J=16.7 Hz, 1H), 5.97 (d, J=9.8 Hz, 1H), 5.34 (dq, J=6.3, 6.6 Hz, 1H), 5.13–5.04 (m, 1H), 5.01 (dd, J=9.8, 1.2 Hz, 1H), 5.00 (br, 1H), 4.91 (dd, J=10.0, 9.5 Hz, 1H), 4.90 (br s, 1H), 4.28 (dd, J=12.2, 5.6 Hz, 1H), 4.04 (dd, J=12.2, 2.4 Hz, 1H), 3.90–3.83 (m, 1H), 3.29 (d, J=14.9 Hz, 1H), 2.92 (d, J=14.9 Hz, 1H), 2.40–1.65 (m, 6H), 2.08 (s, 3H), 2.03 (s, 3H), 1.90 (s, 3H), 1.89 (s, 3H), 1.86 (d, J=6.6 Hz, 3H), 1.74 (d, J=1.2 Hz, 3H)

FABMS m/z 783 (M+H)$^+$

Compound 54

IR (KBr) 3430, 2934, 1739, 1649, 1610, 1527, 1450, 1370, 1244, 1097, 1039, 969, 805 cm$^{-1}$ $^1$H NMR (CDCl$_3$, 400 MHz) δ ppm; 9.21 (dd, J=16.6, 11.5 Hz, 1H), 7.30 (s, 1H), 6.74 (br d, J=6.3 Hz, 1H), 6.65 (d, J=11.5 Hz, 1H), 6.36 (t, J=11.5 Hz, 1H), 6.02 (d, J=16.6 Hz, 1H), 5.93 (d, J=9.8 Hz, 1H), 5.30 (dq, J=6.3, 6.3 Hz, 1H), 5.09 (br s, 1H), 5.02 (dd, J=9.8, 1.2 Hz, 1H), 4.90 (d, J=3.2 Hz, 1H), 4.63 (dd, J=9.8, 9.5 Hz, 1H), 4.32 (dd, J=12.2, 5.4 Hz, 1H), 4.05 (dd, J=12.2, 2.4 Hz, 1H), 3.88–3.76 (m, 2H), 3.22 (d, J=14.7 Hz, 1H), 2.89 (d, J=14.7 Hz, 1H), 2.40–1.60 (m, 6H), 2.14 (s, 3H), 2.07 (s, 3H), 1.90 (s, 3H), 1.79 (d, J=6.6 Hz, 3H), 1.73 (d, J=1.2 Hz, 3H)

FABMS m/z 741 (M+H)$^+$

HRFABMS calcd for C$_{32}$H$_{41}$N$_2$O$_{12}$S$_3$ (M+H)$^+$ 741.1821, found 741.1792

Example 53

Synthesis of Compound 55

In dichloromethane (6.0 mL) were dissolved DC107 (100 mg, 0.20 mmol) and 6-deoxy-3,4-di-O-tert-butyldimethylsilyl-L-glucal (281 mg, 0.78 mmol). Thereto was added camphorsulfonic acid (45 mg, 0.19 mmol). This mixture was stirred at 25° C. for 3 hours. After the ordinary post-treatment, the reaction product was purified by thin-layer chromatography (developed with chloroform/methanol=97/3) to obtain Compound 55 (107 mg, yield 63%).

FABMS m/z 869 (M+H)$^+$

Example 54

Synthesis of Compound 56

Compound 55 (20 mg, 0.023 mmol) obtained in Example 53 was dissolved in tetrahydrofuran (2.0 mL). Thereto was added 3 N hydrochloric acid (0.5 mL). This mixture was stirred at 25° C. for 12 hours. After the ordinary post-treatment, the reaction product was purified by thin-layer chromatography (developed with chloroform/methanol=95/5) to obtain Compound 56 (4.0 mg, yield 27%).

IR (KBr) 3430, 2928, 1712, 1642, 1613, 1533, 1449, 1375, 1266, 1191, 1120, 1066, 1022, 976, 799 cm$^{-1}$ $^1$H NMR (CDCl$_3$, 400 MHz) δ ppm; 8.93 (dd, ,=16.6, 11.5 Hz, 1H), 7.22 (s, 1H), 6.72 (br d, J=6.1 Hz, 1H), 6.56 (d, J=11.3 Hz, 1H), 6.29 (dd, J=11.5, 11.3 Hz, 1H), 5.95 (d, J=16.6 Hz, 1H), 5.77 (d, J=10.0 Hz, 1H), 5.20 (dq, J=6.1, 6.3 Hz, 1H), 4.91 (br s, 1H), 4.81 (d, J=4.0 Hz, 1H), 4.79 (dd, J=10.0, 1.0 Hz, 1H), 3.63–3.33 (m, 2H), 3.14 (d, J=14.6 Hz, 1H), 2.96 (dd, J=9.3, 9.0 Hz, 1H), 2.80 (d, J=14.6 Hz, 1H), 2.30–1.10 (m, 6H), 1.81 (s, 3H), 1.65 (d, J=1.2 Hz, 3H), 1.65 (d, J=6.3 Hz, 3H), 1.11 (d, J=6.1 Hz, 3H)

FABMS m/z 641 (M+H)$^+$

HRFABMS calcd for C$_{28}$H$_{37}$N$_2$O$_9$S$_3$ (M+H)$^+$ 641.1661, found 641.1664

Example 55

Syntheses of Compound 57 and Compound 58

In dichloromethane (5.0 mL) were dissolved DC107 (95 mg, 0.19 mmol) and 6-deoxy-3,4-di-O-acetyl-L-glucal (0.20 mL, 1.0 mmol). Thereto was added camphorsulfonic acid (35 mg, 0.15 mmol). This mixture was stirred at 25° C. for 10 hours. After the ordinary post-treatment, the reaction product was purified by thin-layer chromatography (developed with ether/methanol=95/5) to obtain Compound 57 (38 mg, yield 30%) and Compound 58 (11 mg, yield 8%).

Compound 57

IR (KBr) 3340, 3096, 2982, 2936, 1720, 1642, 1613, 1529, 1449, 1402, 1375, 1238, 1195, 1154, 1100, 1034, 918, 893, 809 cm$^{-1}$ $^1$H NMR (CDCl$_3$, 400 MHz) δ ppm; 9.10 (ddd, J=16.6, 11.5, 1.0 Hz, 1H), 7.27 (s, 1H), 6.81 (br d, J=6.0 Hz, 1H), 6.63 (d, J=11.2 Hz, 1H), 6.37 (dd, J=11.5, 11.2 Hz, 1H), 6.04 (d, J=16.6 Hz, 1H), 5.89 (br d, J=9.8 Hz, 1H), 5.75 (d, J=10.2 Hz, 1H), 5.59 (dt, J=10.2, 2.4 Hz, 1H), 5.27 (dq, J=6.0, 6.3 Hz, 1H), 5.03 br s, 1H), 5.00–4.93 (m, 2H), 4.88 (dd, J=9.8, 1.2 Hz, 1H), 3.64 (dq, J=9.3, 6.3 Hz, 1H), 3.20 (d, J=14.7 Hz, 1H), 2.87 (d, J=14.7 Hz, 1H), 2.38–1.76 (m, 4H), 2.01 (s, 3H), 1.89 (s, 3H), 1.74 (d, J=1.2 Hz, 3H), 1.73 (d, J=6.3 Hz, 3H), 1.05 (d, J=6.3 Hz, 3H)

FABMS m/z 665 (M+H)$^+$

HRFABMS calcd for C$_{30}$H$_{37}$N$_2$O$_9$S$_3$ (M+H)$^+$ 665.1661, found 665.1672

Compound 58

IR (KBr) 3420, 2980, 2940, 1729, 1647, 1613, 1528, 1451, 1371, 1250, 1230, 1122, 1095, 1040, 943, 887, 805 cm$^{-1}$

¹H NMR (CDCl₃, 500 MHz) δ ppm; 9.07 (ddd, J=16.4, 11.5, 1.0 Hz, 1H), 7.29 (s, 1H), 6.79 (br d, J=6.2 Hz, 1H), 6.66 (d, J=11.2 Hz, 1H), 6.38 (dd, J=11.5, 11.2 Hz, 1H), 6.05 (d, J=16.6 Hz, 1H), 5.90 (br d, J=9.8 Hz, 1H), 5.28 (dq, J=6.2, 6.4 Hz, 1H), 5.03–4.92 (m, 1H), 4.99 (br s, 1H), 4.91 (br d, J=3.2 Hz, 1H), 4.83 (dd, J=9.8, 1.2 Hz, 1H), 4.65 (dd, J=9.7, 9.5 Hz, 1H), 3.73–3.63 (m, 1H), 3.23 (d, J=14.6 Hz, 1H), 2.87 (d, J=14.6 Hz, 1H), 2.38–1.50 (m, 6H), 1.97 (s, 3H), 1.92 (s, 3H), 1.90 (s, 3H), 1.74 (d, J=6.4 Hz, 3H), 1.73 (s, 3H), 1.06 (d, J=6.1 Hz, 3H)

FABMS m/z 725 (M+H)⁺

HRFABMS calcd for $C_{32}H_{41}N_2O_{11}S_3$ (M+H)⁺ 725.1872, found 725.1860

Example 56

Synthesis of Compound 59

In dichloromethane (2.0 mL) were dissolved Compound A (30 mg, 0.048 mmol) obtained in Reference Example 1 and 2,3,4,6-tetraacetylglucose-1-O-trichloroacetimidate (120 mg, 0.24 mmol). Thereto was added a boron trifluoride/diethyl ether complex (10 µL, 0.081 mmol) at 0° C. This mixture was stirred for 3 hours. After the ordinary post-treatment, the reaction product was purified by thin-layer chromatography (developed with ether/methanol=95/5) to obtain Compound 59 (8.5 mg, yield 19%).

IR (KBr) 3450, 2970, 2932, 1822, 1754, 1690, 1653, 1440, 1369, 1225, 1040, 980, 770 cm⁻¹

¹H NMR (CDCl₃, 500 MHz) δ ppm; 9.06 (ddd, J=16.5, 11.3, 0.9 Hz, 1H), 7.47 (s, 1H), 6.59 (d, J=11.6 Hz, 1H), 6.33 (dd, J=11.6, 11.3 Hz, 1H), 5.97 (d, J=16.5 Hz, 1H), 5.73 (br d, J=7.9 Hz, 1H), 5.54 (q, J=6.5 Hz, 1H), 5.51 (br s, 1H), 5.13 (dd, J=9.5, 9.3 Hz, 1H), 4.98 (dd, J=10.1, 9.5 Hz, 1H), 4.89 (dd, J=9.3, 7.9 H, 1H), 4.69 (d, J=7.9 Hz, 1H), 4.68 (br d, J=7.9 Hz, 1H), 4.09 (dd, J=12.2, 5.8 Hz, 1H), 4.03 (dd, J=12.2, 2.7 Hz, 1H), 4.01 (d, J=17.7 Hz, 1H), 3.81 (dd, J=15.3, 0.9 Hz, 1H), 3.7.3 (dd, J=15.3, 0.9 Hz, 1H), 3.63 (ddd, J=10.1, 5.8, 2.7 Hz, 1H), 2.40–1.55 (m, 4H), 2.33 (d, J=17.7 Hz, 1H), 2.14 (br s, 3H), 2.10 (s, 3H), 2.00 (s, 3H), 1.94 (s, 3H), 1.93 (s, 3H), 1.79 (d, J=6.5 Hz, 3H), 1.72 (d, J=1.2 Hz, 3H), 1.68 (s, 3H)

FABMS m/z 953 (M+H)⁺

Example 57

Synthesis of Compound 60

In dichloromethane (5.0 mL) were dissolved Compound A (84 mg, 0.14 mmol) obtained in Reference Example 1 and 3,4,6-tri-O-acetyl-D-glucal (184 mg, 0.68 mmol). Thereto was added camphorsulfonic acid (31 mg, 0.14 mmol). This mixture was stirred at 25° C. for 29 hours. After the ordinary post-treatment, the reaction product was purified by thin-layer chromatography (developed with ether/methanol=95/5) to obtain Compound 60 (7.7 mg, yield 7%).

IR (KBr) 3402, 2932, 1821, 1737, 1680, 1640, 1608, 1441, 1371, 1239, 1094, 1031, 768, 731 cm⁻¹

¹H NMR (CDCl₃, 400 MHz) δ ppm; 9.74 (dd, J=16.6, 11.5 Hz, 1H), 7.42 (s, 1H), 6.63 (d, J=11.2 Hz, 1H), 6.36 (dd, J=11.5, 11.2 Hz, 1H), 6.02 (d, J=16.6 Hz, 1H), 5.83 (br d, J=9.3 Hz, 1H), 5.76 (br d, J=10.2 Hz, 1H), 5.63 (ddd, J=10.2, 2.7, 2.2 Hz, 1H), 5.60 (q, J=6.6 Hz, 1H), 5.51 (br s, 1H), 5.28–5.23 (m, 1H), 5.05 (dd, J=9.3, 1.2 Hz, 1H), 5.01 (br s, 1H), 4.24 (dd, J=12.0, 5.5 Hz, 1H), 4.12 (dd, J=12.0, 2.5 Hz, 1H), 4.07 (d, J=17.6 Hz, 1H), 3.99–3.93 (m, 1H), 3.81 (d, J=15.2 Hz, 1H), 3.75 (d, J=15.2 Hz, 1H), 2.50–1.30 (m, 4H), 2.26 (d, J=17.6 Hz, 1H), 2.15 (s, 3H), 2.09 (s, 3H), 2.07 (s, 3H), 1.84 (d, J=6.6 Hz, 3H), 1.80 (d, J=1.0 Hz, 3H), 1.72 (s, 3H)

FABMS m/z 835 (M+H)⁺

HRFABMS calcd for $C_{37}H_{43}N_2O_{14}S_3$ (M+H)⁺ 835.1876, found 835.1886

Example 58

Synthesis of Compound 61

In dichloromethane (4.0 mL) were dissolved Compound A (80 mg, 0.13 mmol) obtained in Reference Example 1 and tri-O-tert-butyldimethylsilyl-D-glucal (190 mg, 0.39 mmol). Thereto was added camphorsulfonic acid (30 mg, 0.13 mmol). This mixture was stirred at 25° C. for 3 hours. After the ordinary post-treatment, the reaction product was purified by thin-layer chromatography (developed with chloroform/methanol=97/3) to obtain Compound 61 (70 mg, yield 49%).

FABMS m/z 1111 (M+H)⁺

Example 59

Synthesis of Compound 62

Compound 61 (70 mg, 0.063 mmol) obtained in Example 58 was dissolved in methanol (4.0 mL). Thereto was added 3 N hydrochloric acid (0.1 mL). This mixture was stirred at 25° C. for 5 hours. After the ordinary post-treatment, the reaction product was purified by thin-layer chromatography (developed with chloroform/methanol=95/5) to obtain Compound 62. (11 mg, yield 23%). This Compound 62 was an approximately 2:1 mixture of diastereomers.

¹H NMR (CDCl₃, 500 MHz) δ ppm; major isomer 9.46 (dd, J=16.6, 11.5 H, 1H), 7.40 (s, 1H), 6.61 (d, J=11.5 Hz, 1H), 6.35 (t, J=11.5 Hz, 1H), 6.02 (d, J=16.6 Hz, 1H), 5.80 (br d, J=9.0 Hz, 1H), 5.57 (q, J=6.6 Hz, 1H), 5.49 (br s, 1H), 4.71 (dd, J=9.5, 2.0 Hz, 1H), 4.67 (br d, J=9.0 Hz, 1H), 4.04 (d, J=17.8 Hz, 1H), 3.90–3.25 (m, 6H), 2.50–1.50 (m, 6H), 2.27 (d, J=17.8 Hz, 1H), 2.14 (s, 3H), 1.87 (d, J=6.6 Hz, 3H), 1.73 (d, J=1.0 Hz, 3H), 1.69 (s, 3H), minor isomer 9.48 (dd, J=16.6, 11.5 Hz, 1H), 7.43 (s, 1H), 6.64 (d, J=11.5 Hz, 1H), 6.35 (t, J=11.5 Hz, 1H), 6.02 (d, J=16.6 Hz, 1H), 5.83 (br d, J=9.0 Hz, 1H), 5.59 (q, J=6.6 Hz, 1H), 5.42 (br s, 1H), 4.93 (br d, J=5.7 Hz, 1H), 4.90 (br d, J=9.0 Hz, 1H), 4.03 (d, J=17.8 Hz, 1H), 3.90–3.25 (m, 6H), 2.50–1.50 (m, 6H), 2.31 (d, J=17.8 Hz, 1H), 2.14 (s, 3H), 1.94 (d, J=6.6 Hz, 3H), 1.75 (d, J=1.0 Hz, 3H), 1.69 (s, 3H)

FABMS m/z 769 (M+H)⁺

Example 60

Synthesis of Compound 63

In dichloromethane (4.0 mL) were dissolved Compound A (105 mg, 0.17 mmol) obtained in Reference Example 1 and 6-deoxy-3,4-di-O-tert-butyldimethylsilyl-L-glucal (242 mg, 0.68 mmol). Thereto was added camphorsulfonic acid (39 mg, 0.17 mmol). This mixture was stirred at 25° C. for 9 hours. After the ordinary post-treatment, the reaction product was purified by thin-layer chromatography (developed with chloroform/methanol=97/3) to obtain Compound 63 (71 mg, yield 43%).

FABMS m/z 980 (M+H)⁺

Example 61

Syntheses of Compound 64 and Compound 65

Compound 63 (71 mg, 0.072 mmol) obtained in Example 60 was dissolved in methanol (4.0 mL). Thereto was added 3 N hydrochloric acid (0.5 mL). This mixture was stirred at 25° C. for 3 hours. After the ordinary post-treatment, the reaction product was purified by thin-layer chromatography (developed with chloroform/methanol=95/5) to obtain Compound 64 (19 mg, yield 35%) and Compound 65 (6.0 mg, yield 11%), which is a diastereomer of Compound 64.

Compound 64

IR (KBr) 3420, 2980, 2936, 1817, 1720, 1680, 1646, 1609, 1450, 1376, 1267, 1208, 1117, 975, 770, 731 cm$^{-1}$ $^1$H NMR (CDCl$_3$, 500 MHz) δ ppm; 9.33 (ddd, J=16.6, 11.4, 1.0 Hz, 1H), 7.42 (s, 1H), 6.62 (d, J=11.5 Hz, 1H), 6.36 (dd, J=11.5, 11.4 Hz, 1H), 6.03 (d, J=16.6 Hz, 1H), 5.80 (br d, J=9.2 Hz, 1H), 5.57 (q, J=6.5 Hz, 1H), 5.44 (br s, 1H), 4.96 (br d, J=3.6 Hz, 1H), 4.72 (dd, J=9.2, 1.0 Hz, 1H), 4.04 (d, J=17.7 Hz, 1H), 3.84–3.70 (m, 3H), 3.57–3.50 (m, 1H), 3.06 (t, J=9.2 Hz, 1H), 2.44–1.45 (m, 6H), 2.30 (d, J=17.7 Hz, 1H), 2.14 (s, 3H), 1.90 (d, J=6.5 Hz, 3H), 1.75 (d, J=1.0 Hz, 3H), 1.69 (s, 3H), 1.18 (d, J=6.2 Hz, 3H)

FABMS m/z 753 (M+H)$^+$

HRFABMS calcd for C$_{33}$H$_{41}$N$_2$O$_{12}$S$_3$ (M+H)$^+$ 753.1821, found 753.1791

Compound 65

IR (KBr) 3420, 2934, 1819, 1720, 1687, 1645, 1607, 1448, 1376, 1264, 1208, 1120, 1067, 975, 769 cm$^{-1}$ $^1$H NMR (CDCl$_3$, 500 MHz) δ ppm; 9.63 (ddd, J=16.5, 11.6, 1.0 Hz, 1H), 7.41 (s, 1H), 6.62 (d, J=11.6 Hz, 1H), 6.35 (t, J=11.6 Hz, 1H), 6.00 (dd, J=16.5, 1.0 Hz, 1H), 5.78 (br d, J=8.8 Hz, 1H), 5.58 (q, J=6.7 Hz, 1H), 5.52 (br s, 1H), 5.06 (dd, J=8.8, 1.2 Hz, 1H), 4.47 (dd, J=9.8, 2.1 Hz, 1H), 4.04 (d, J=17.4 Hz, 1H), 3.77 (br s, 2H), 3.55–3.48 (m, 1H), 3.26–3.00 (m, 2H), 2.48–1.40 (m, 6H), 2.25 (d, J=17.4 Hz, 1H), 2.14 (s, 3H), 1.90 (d, J=6.7 Hz, 3H), 1.75 (d, J=1.2 Hz, 3H), 1.70 (s, 3H), 1.31 (d, J=6.2 Hz, 3H)

FABMS m/z 753 (M+H)$^+$

HRFABMS calcd for C$_{33}$H$_{41}$N$_2$O$_{12}$S$_3$ (M+H)$^+$ 753.1821, found 753.1797

Example 62

Synthesis of Compound 66

To Compound 64 (35 mg, 0.02 mmol) obtained in Example 61 were added dichloromethane (2.0 mL), pyridine (0.1 mL), and acetic anhydride (0.05 mL). This mixture was stirred at 25° C. for 3 hours. After the ordinary post-treatment, the reaction product was purified by thin-layer chromatography (developed with chloroform/methanol=96/4) to obtain Compound 66 (22 mg, yield 56%).

IR (KBr) 3400, 2936, 1822, 1736, 1685, 1650, 1610, 1444, 1371, 1229, 1120, 1092, 1037, 981, 941, 769 cm$^{-1}$ $^1$H NMR (CDCl$_3$, 400 MHz) δ ppm; 9.35 (ddd, J=16.6, 11.5, 1.0 Hz, 1H), 7.43 (s, 1H), 6.64 (d, J=11.7 Hz, 1H), 6.37 (dd, J=11.7, 11.5 Hz, 1H), 6.04 (d, J=16.6 Hz, 1H), 5.82 (br d, J=9.3 Hz, 1H), 5.57 (q, J=6.6 Hz, 1H), 5.44 (br s, 1H), 5.10–5.02 (m, 1H), 4.97 (br d, J=3.6 Hz, 1H), 4.71 (dd, J=9.3, 1.2 Hz, 1H), 4.69 (dd, J=9.7, 9.5 Hz, 1H), 4.03 (d, J=17.8 Hz, 1H), 3.83–3.70 (m, 3H), 2.43–1.40 (m, 6H), 2.30 (d, J=17.8 Hz, 1H), 2.14 (s, 3H), 1.99 (s, 3H), 1.94 (s, 3H), 1.91 (d, J=6.6 Hz, 3H), 1.75 (d, J=1.0 Hz, 3H), 1.69 (s, 3H), 1.06 (d, J=6.3 Hz, 3H)

FABMS m/z 837 (M+H)$^+$

HRFABMS calcd for C$_{37}$H$_{45}$N$_2$O$_{14}$S$_3$ (M+H)$^+$ 837.2033, found 837.2050

Example 63

Synthesis of Compound 67

In dichloromethane (3.0 mL) were dissolved Compound A (110 mg, 0.18 mmol) obtained in Reference Example 1 and 6-deoxy-3,4-di-O-p-methoxybenzyl-L-glucal (260 mg, 0.71 mmol). Thereto was added camphorsulfonic acid (20 mg, 0.089 mmol). This mixture was stirred at 25° C. for 2 hours. After the ordinary post-treatment, the residue was dissolved in dichloromethane (5.0 mL). Water (0.5 mL) and 2,3-dichloro-5,6-dicyano-p-benzoquinone (75 mg, 0.33 mmol) were added thereto, and this mixture was stirred at 25° C. for 5 hours. After the ordinary post-treatment, the reaction product was purified by thin-layer chromatography (developed with chloroform/methanol=95/5) to obtain Compound 67 (19 mg, yield 35%).

IR (KBr) 3420, 2980, 2936, 1817, 1681, 1645, 1609, 1449, 1377, 1266, 1208, 1149, 1095, 1031, 992, 885, 770, 733 cm$^{-1}$ $^1$H NMR (CDCl$_3$, 500 MHz) δ ppm; 9.52 (ddd, J=16.5, 11.4, 1.0 Hz, 1H), 7.47 (s, 1H), 6.60 (d, J=11.4 Hz, 1H), 6.35 (t, J=11.4 Hz, 1H), 6.05 (d, J=16.5 Hz, 1H), 5.85 (br d, J=10.2 Hz, 1H), 5.81 (br d, J=8.9 Hz, 1H), 5.61–5.52 (m, 1H), 5.56 (q, J=6.6 Hz, 1H), 5.51 (br s, 1H), 5.06 (br s, 1H), 4.70 (dd, J=8.9, 1.2 Hz, 1H), 4.04 (d, J=17.6 Hz, 1H), 3.82–3.73 (m, 3H), 3.50–3.43 (m, 1H), 2.46–1.34 (m, 4H), 2.28 (d, J=17.6 Hz, 1H), 2.14 (s, 3H), 1.85 (d, J=6.6 Hz, 3H), 1.74 (d, J=1.2 Hz, 3H), 1.70 (s, 3H), 1.13 (d, J=6.2 Hz, 3H)

FABMS m/z 735 (M+H)$^+$

HRFABMS calcd for C$_{33}$H$_{39}$N$_2$O$_{11}$S$_3$ (M+H)$^+$ 735.1716, found 735.1738

Example 64

Syntheses of Compound 68 and Compound 69

In dichloromethane (5.0 mL) were dissolved Compound A (90 mg, 0.14 mmol) obtained in Reference Example 1 and 6-deoxy-3,4-di-O-acetyl-L-glucal (0.27 mL, 1.4 mmol). Thereto was added camphorsulfonic acid (32 mg, 0.14 mmol). This mixture was stirred at 25° C. for 2 hours. After the ordinary post-treatment, the reaction product was purified by thin-layer chromatography (developed with ether/methanol=95/5) to obtain Compound 68 (25 mg, yield 23%) and Compound 69 (38 mg, yield 35%), which is a diastereomer of Compound 68.

Compound 68

IR (KBr) 3420, 3092, 2984, 2936, 2874, 1820, 1729, 1685, 1648, 1607, 1450, 1374, 1240, 1208, 1142, 1091, 1068, 1039, 976, 920, 808, 769 cm$^{-1}$ $^1$H NMR (CDCl$_3$, 500 MHz) δ ppm; 9.49 (ddd, J=16.5, 11.5, 1.0 Hz, 1H), 7.41 (s, 1H), 6.62 (d, J=11.5 Hz, 1H), 6.37 (t, J=11.5 Hz, 1H), 6.05 (d, J=16.5 Hz, 1H), 5.81 (br d, J=9.0 Hz, 1H), 5.80–5.60 (m, 2H), 5.57 (q, J=6.6 Hz, 1H), 5.48 (br s, 1H), 5.10–4.95 (m, 2H), 4.73 (dd, J=9.0, 1.2 Hz, 1H), 4.04 (d, J=17.6 Hz, 1H), 3.79 (d, J=15.5 Hz, 1H), 3.76 (d, J=15.5 Hz, 1H), 3.73–3.65 (m, 1H), 2.46–1.42 (m, 4H), 2.28 (d, J=17.6 Hz, 1H), 2.14 (s, 3H), 2.01 (s, 3H), 1.86 (d, J=6.6 Hz, 3H), 1.74 (d, J=1.2 Hz, 3H), 1.70 (s, 3H), 1.05 (d, J=6.3 Hz, 3H)

FABMS m/z 777 (M+H)$^+$

HRFABMS calcd for C$_{35}$H$_{41}$N$_2$O$_{12}$S$_3$ (M+H)$^+$ 777.1821, found 777.1809

Compound 69

IR (KBr) 3420, 3090, 2982, 2936, 1818, 1723, 1681, 1647, 1609, 1447, 1375, 1239, 1209, 1152, 1101, 1032, 980, 918, 809, 769, 733 cm$^{-1}$

¹H NMR (CDCl₃, 500 MHz) δ ppm; 9.65 (ddd, J=16.6, 11.5, 0.8 Hz, 1H), 7.41 (s, 1H), 6.62 (d, J=11.5 Hz, 1H), 6.35 (t, J=11.5 Hz, 1H), 6.01 (d, J=16.6 Hz, 1H), 5.87–5.69 (m, 3H), 5.57 (q, J=6.6 Hz, 1H), 5.52 (br s, 1H), 5.14–4.95 (m, 3H), 4.04 (d, J=17.8 Hz, 1H), 3.86–3.76 (m, 1H), 3.77 (br s, 2H), 2.47–1.35 (m, 4H), 2.26 (d, J=17.8 Hz, 1H), 2.14 (s, 3H), 2.05 (s, 3H), 1.84 (d, J=6.6 Hz, 3H), 1.76 (d, J=1.2 Hz, 3H), 1.70 (s, 3H), 1.24 (d, J=6.3 Hz, 3H)

FABMS m/z 777 (M+H)⁺

HRFABMS calcd for $C_{35}H_{41}N_2O_{12}S_3$ (M+H)⁺ 777.1821, found 777.1794

Example 65

Synthesis of Compound 70

In dichloromethane (5.0 mL) were-dissolved Compound A (100 mg, 0.16 mmol) obtained in Reference Example 1 and 3,4,6-tri-O-acetyl-D-galactal (219 mg, 0.80 mmol). Thereto was added camphorsulfonic acid (37 mg, 0.16 mmol). This mixture was stirred at 25° C. for 27 hours. After the ordinary post-treatment, the reaction product was purified by thin-layer chromatography (developed with chloroform/methanol=96/4) to obtain Compound 70 (19 mg, yield 13%)

IR (KBr) 3420, 2932, 1822, 1746, 1720, 1685, 1650, 1609, 1443, 1372, 1255, 1110, 1020, 770 cm⁻¹

¹H NMR (CDCl₃, 500 MHz) δ ppm; 9.46 (ddd, J=16.8, 11.3, 1.0 Hz, 1H), 7.42 (s, 1H), 6.63 (d, J=11.6 Hz, 1H), 6.34 (dd, J=11.6, 11.3 Hz, 1H), 6.02 (d, J=16.8 Hz, 1H), 5.85 (br d, J=9.5 Hz, 1H), 5.59 (q, J=6.7 Hz, 1H), 5.45 (br s, 1H), 5.27 (br d, J=2.7 Hz, 1H), 5.14–5.08 (m, 1H), 5.05 (d, J=3.4 Hz, 1H), 4.94 (dd, J=9.5, 1.2 Hz, 1H), 4.19 (dd, J=11.0, 7.0 Hz, 1H), 4.10 (br dd, J=7.0, 6.7 Hz, 1H), 4.03 (d, J=17.7 Hz, 1H), 4.00 (dd, J=11.0, 6.7 Hz, 1H), 3.78 (br s, 2H), 2.49–1.46 (m, 6H), 2.30 (d, J=17.7 Hz, 1H), 2.15 (s, 3H), 2.11 (s, 3H), 2.07 (s, 3H), 1.92 (d, J=6.7 Hz, 3H), 1.92 (s, 3H), 1.80 (d, J=1.2 Hz, 3H), 1.70 (s, 3H)

FABMS m/z 895 (M+H)⁺

HRFABMS calcd for $C_{39}H_{47}N_2O_{16}S_3$ (M+H)⁺ 895.2087, found 895.2059

Reference Examples for the present invention will be given below. The structures of the compounds synthesized in the Reference Examples are shown in Table 5.

TABLE 5

Structures of Compounds in Reference Examples

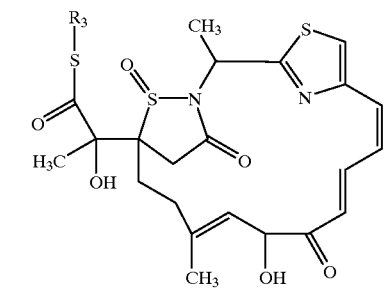

| Compound | R³ |
|---|---|
| A | 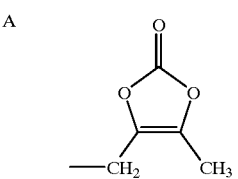 |
| B | 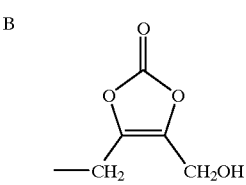 |
| C | 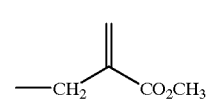 |
| D | 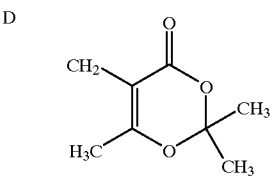 |
| E | 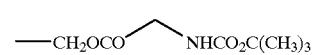 |
| F | 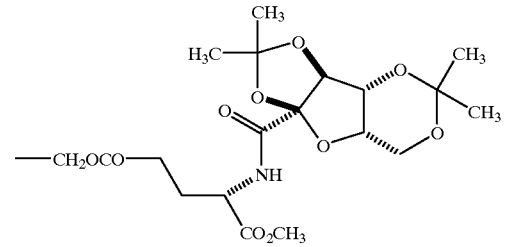 |

TABLE 5-continued

Structures of Compounds in Reference Examples

| Compound | R³ |
|---|---|
| G | —CH₂OCO— [2,2-dimethyl-1,3-dioxolane fused to 2,2-dimethyl-1,3-dioxane, with CONH-CH(CO₂CH₃)- linker] |
| H | —CH₂OCO— [2,2-dimethyl-1,3-dioxane with methyl, CONH-CH(CO₂CH₃)- linker] |
| I | —CH₂OCO—(CH₂)₃—CONH— [2,2,5-trimethyl-1,3-dioxane] |
| J | —CH₂OCO—CH₂CH₂—N(2-pyrrolidinone) |
| K | —CH₂OCO₂(CH₂CH₂O)₂CH₃ |
| L | —CH₂OCOCH₂O(CH₂CH₂O)₂—CH₂—C₆H₄—OCH₃ |

Reference Example 1

Synthesis of Compound A

DC107 (150 mg, 0.29 mmol) was dissolved in dimethylformamide (10 mL). Thereto were added potassium carbonate (1.2 g, 8.9 mmol), 4-chloromethyl-5-methyl-2-oxo-1,3-dioxolane (0.86 g, 5.8 mmol), and potassium iodide (245 mg, 1.47 mmol). This mixture was stirred at 25° C. for 1 hour. After the ordinary post-treatment, the reaction product was purified by silica gel column chromatography (eluted with chloroform) to obtain Compound A (125 mg, yield 69%).

IR (KBr) 3420, 2936, 1819, 1680, 1647, 1611, 1450, 1375, 1265, 1208, 1150, 1092, 980, 768 cm⁻¹

¹H NMR (CDCl₃, 400 MHz) δ ppm; 8.37 (ddd, J=16.3, 11.7, 1.0 Hz, 1H), 7.28 (s, 1H), 6.52 (d, J=11.7 Hz, 1H), 6.17 (dd, J=11.7, 11.7 Hz, 1H), 6.11 (d, J=16.3 Hz, 1H), 5.66 (br d, J=8.5 Hz, 1H), 5.34 (q, J=6.9 Hz, 1H), 4.88 (d, J=8.5 Hz, 1H), 3.83 (d, J=17.9 Hz, 1H), 3.69 (br s, 2H), 2.23–1.60 (m 4H), 2.18 (d, J=17.9 Hz, 1H), 2.07 (s, 3H), 1.95 (d, J=6.9 Hz, 3H), 1.71 (s, 3H), 1.68 (d, J=1.2 Hz, 3H)

FABMS m/z 623 (M+H)⁺

HRFABMS calcd for C₂₇H₃₁N₂O₉S₃ (M+H)⁺ 623.1192, found 623.1174

Reference Example 2

Synthesis of Compound B

In acetonitrile (1.5 mL) were dissolved DC107 (9.8 mg, 0.016 mmol) and 4-bromomethyl-5-(triethylsilyloxy)methyl-1,3-dioxolan-2-one (21 mg, 0.063 mmol). Thereto was added potassium carbonate (9.1 mg, 0.063 mmol). This mixture was stirred at 25° C. for 3 hours. After the ordinary post-treatment, the reaction product was purified by silica gel chromatography (eluted with n-hexane/ethyl acetate=3/2) to obtain a triethylsilylated Compound B (14 mg, yield 98%).

The triethylsilylated Compound B (9.1 mg, 0.012 mmol) was dissolved in tetrahydrofuran (0.3 mL). Thereto were added acetic acid (0.0014 mL, 0.024 mmol) and a 1.0 N tetrabutylammonium fluoride solution in tetrahydrofuran (0.024 mL, 0.024 mmol). This mixture was stirred at 0° C. for 5 minutes. After the ordinary post-treatment, the reaction product was purified by silica gel chromatography (eluted with n-hexane/ethyl acetate=1/5) to obtain Compound B (9.0 mg, quantitative yield).

¹H NMR (CDCl₃, 400 MHz) δ ppm; 8.43 (dd, J=16.4, 11.3 Hz, 1H), 7.35 (s, 1H), 6.59 (d, J=11.3 Hz, 1H), 6.23 (dd, J=11.3, 11.3 Hz, 1H), 6.18 (d, J=16.4 Hz, 1H), 5.72 (d, J=8.3 Hz, 1H), 5.41 (q, J=6.9 Hz, 1H), 5.22 (br s, 1H), 4.96 (d, J=8.3 Hz, 1H), 4.49 (d, J=5.4 Hz, 2H), 3.98 (d, J=17.8 Hz, 1H), 3.92 (d, J=15.3 Hz, 1H), 3.85 (br s, 1H) 3.79 (d, J=15.3 Hz, 1H), 2.88 (br, 1H), 2.34–2.15 (m, 4H), 2.28 (d, J=17.8 Hz, 1H), 2.00 (d, J=6.9 Hz, 3H), 1.74 (s, 3H), 1.70 (s, 3H)

FABMS m/z 639 (M+H)⁺ calcd for C₂₇H₃₀N₂O₁OS₃=638

Reference Example 3

Synthesis of Compound C

DC107 (55 mg, 0.11 mmol) was dissolved in acetonitrile (5.0 mL). Thereto were added potassium carbonate (45 mg, 0.33 mmol) and methyl 2-bromomethylacrylate (0.040 mL, 0.33 mmol). This mixture was stirred at 25° C. for 4.5 hours. After the ordinary post-treatment, the reaction product was purified by thin-layer chromatography (developed with chloroform/methanol=97/3) to obtain Compound C (36 mg, yield 54%).

IR (KBr) 3420, 3104, 2938, 1712, 1680, 1609, 1439, 1377, 1333, 1255, 1204, 1105, 986, 813 cm⁻¹

¹H NMR (CDCl₃, 400 MHz) δ ppm; 8.45 (ddd, J=16.4, 11.2, 1.0 Hz, 1H), 7.34 (s, 1H), 6.57 (d, J=11.7 Hz, 1H), 6.23 (br s, 1H), 6.23 (dd, J=11.7, 11.2 Hz, 1H), 6.17 (d, J=16.4

Hz, 1H), 5.85 (br s, 1H), 5.72 (br d, J=8.8 Hz, 1H), 5.47 (br s, 1H), 5.40 (q, J=6.8 Hz, 1H), 4.94 (dd, J=8.8, 3.7 Hz, 1H), 3.90 (d, J=17.8 Hz, 1H), 3.78–3.65 (m, 3H), 3.76 (s, 3H), 2.36–1.82 (m, 4H), 2.25 (d, J=17.8 Hz, 1H), 2.02 (d, J=6.8 Hz, 3H), 1.77 (s, 3H), 1.75 (d, J=1.0 Hz, 3H)

FABMS m/z 609 (M+H)$^+$

HRFABMS calcd for $C_{27}H_{33}N_2O_8S_3$ (M+H)$^+$ 609.1399, found 609.1418

Reference Example 4

Synthesis of Compound D

DC107 (102 mg, 0.20 mmol) was dissolved in acetonitrile (5.0 mL). Thereto were added potassium carbonate (55 mg, 0.40 mmol) and 5-bromomethyl-2,2,6-trimethyl-4H-1,3-dioxin-4-one (94 mg, 0.40 mmol). This mixture was stirred at 25° C. for 9 hours. After the ordinary post-treatment, the reaction product was purified by thin-layer chromatography (developed with chloroform/methanol=97/3) to obtain Compound D (84 mg, yield 63%).

IR (KBr) 3420, 2936, 1711, 1670, 1637, 1611, 1393, 1356, 1274, 1205, 1160, 1054, 985, 900, 780, 730 cm$^{-1}$ $^1$H NMR (CDCl$_3$, 400 MHz) δ ppm; 8.45 (dd, J=16.4, 11.2 Hz, 1H), 7.34 (s, 1H), 6.58 (d, J=11.7 Hz, 1H), 6.57 (dd, J=11.7, 11.2 Hz, 1H), 6.17 (d, J=16.4 Hz, 1H), 5.73 (br d, J=9.5 Hz, 1H), 5.40 (q, J=6.8 Hz, 1H), 5.38 (br s, 1H), 4.94 (dd, J=9.5, 3.7 Hz, 1H), 3.91 (d, J=17.8 Hz, 1H), 3.81 (d, J=13.8 Hz, 1H), 3.74 (d, J=3.7 Hz, 1H), 3.71 (d, J=13.8 Hz, 1H), 2.30 (d, J=17.8 Hz, 1H), 2.40–1.55 (m, 4H), 2.08 (s, 3H), 2.01 (d, J=6.8 Hz, 3H), 1.78 (s, 3H), 1.75 (d, J=1.0 Hz, 3H), 1.63 (s, 6H)

FABMS m/z 665 (M+H)$^+$

HRFABMS calcd for $C_{30}H_{37}N_2O_9S_3$ (M+H)$^+$ 665.1661, found 665.1635

Reference Example 5

Synthesis of Compound E

Boc—Gly—OH (3.20 g, 18.3 mmol) was dissolved in a mixture of dichloromethane (80 mL) and distilled water (80 mL). Sodium bicarbonate (4.14 g, 30 mmol) was added thereto little by little while giving care to bubbling. Thereto was further added tetrabutylammonium hydrogen sulfate (678 mg, 2.0 mmol). This mixture was stirred at room temperature. Ten minutes later, chloromethyl chlorosulfonate (3.53 g, 21.4 mmol) was added and this mixture was continuously stirred for 2.5 hours. After the progress of the reaction was ascertained by TLC, the reaction mixture was subjected to the ordinary post-treatment and then purified by column chromatography (silica gel; eluted with n-hexane/ethyl acetate=2/1 to 9/1) to obtain a chloromethyl ester (Boc—Gly—OCH$_2$Cl) (3.19 g, yield 78%).

$^1$H NMR (CDCl$_3$, 270 MHz) δ ppm; 5.75 (s, 2H), 5.1 (br s, 1H), 3.99 (d, J=6.9 Hz, 1H), 1.46 (s, 9H)

To a solution of the chloromethyl ester obtained (Boc—Gly—OCH$_2$Cl) (2.24 g, 10.0 mmol) and DC107 (510 mg, 1.00 mmol) in acetone (50 mL) were added powdered potassium iodide (1.66 g, 10.0 mmol) and potassium carbonate (1.38 g, 10.0 mmol). The resultant suspension was stirred at room temperature for 7 hours. The reaction mixture was subjected to the ordinary post-treatment and then purified by column chromatography (silica gel; eluted with chloroform/methanol=20/1) to obtain a crude reaction product (325 mg) containing the target compound. This crude product was purified by HPLC for fractionation (mobile phase: acetonitrile/water=45/55) to obtain Compound E (182 mg, yield 26%)

$^1$H NMR (CDCl$_3$, 270 MHz) δ ppm; 8.47 (dd, J=11.4, 16.6 Hz, 1H), 7.35 (s, 1H), 6.59 (d, J=11.4 Hz, 1H), 6.23 (t, J=11.4 Hz, 1H), 6.17 (d, J=16.6 Hz, 1H), 5.74 (br d, J=8.9 Hz, 1H), 5.5 (br s, 1H), 5.45 (s, 2H), 5.41 (q, J=6.9 Hz, 1H), 5.0 (br s, 1H), 4.95 (d, J=8.9 Hz, 1H), 3.90 (d, J=ca. 7 Hz, 2H), 3.88 (d, J=17.8 Hz, 1H), 3.8 (br s, 1H), 2.3–1.5 (m, 4H), 2.28 (d, J=17.8 Hz, 1H), 2.02 (d, J=6.9 Hz, 3H), 1.78 (s, 3H), 1.75 (d, J=1.0 Hz, 3H), 1.44 (s, 9H)

FABMS m/z 698 (M+H)$^+$ calcd for $C_{30}H_{39}N_3O_{10}S_3$=697

Reference Example 6

Synthesis of Compound F

In the same manner as in Reference Example 5, a chloromethyl ester (Boc—L—Glu(OCH$_2$Cl)—OBu$^t$) (1.86 g, yield 91%) was obtained from Boc—L—Glu (OH)—OBu$^t$ (1.76 g, 5.81 mmol) and chloromethyl chlorosulfonate (1.15 g, 6.97 mmol) through 2-hour reaction.

$^1$H NMR (CDCl$_3$, 270 MHz) δ ppm; 5.71 (s, 2H), 4.21 (m, 1H), 2.48 (m, 2H), 2.19 (m, 1H), 1.93 (m, 1H), 1.47 (s, 9H), 1.44 (s, 9H)

To a solution of the chloromethyl ester obtained (Boc—L—Glu(OCH$_2$Cl)—OBu$^t$) (176 mg, 0.500 mmol) and DC107 (26 mg, 0.051 mmol) in acetone (2.5 mL) were added powdered potassium iodide (83 mg, 0.50 mmol) and potassium carbonate (70 mg, 0.51 mmol). The resultant suspension was stirred at room temperature for 6.5 hours. The reaction mixture was subjected to the ordinary post-treatment and then purified by thin-layer chromatography (silica gel; developed with chloroform/methanol=20/1) to obtain Compound F (15 mg, yield 36%).

$^1$H NMR (CDCl$_3$, 270 MHz) δ ppm; 8.46 (dd, J=10.6, 16.1 Hz, 1H), 7.35 (s, 1H), 6.59 (d, J=11.9 Hz, 1H), 6.23 (t, J=11.6 Hz, 1H), 6.17 (d, J=16.2 Hz, 1H), 5.73 (br d, J=8.4 Hz, 1H), 5.50 (br s, 1H), 5.41 (q, 1H, overlapped with other peaks), 5.40 (s, 2H), 5.08 (br d, J=5.9 Hz, 1H), 4.95 (dd, J=4.0, 8.4 Hz, 1H), 4.16 (m, 1H), 3.89 (d, J=17.8 Hz, 1H), 3.77 (d, J=4.0 Hz, 1H), 2.4–1.2 (m, 8H), 2.28 (d, J=17.8 Hz, 1H), 2.02 (d, J=6.9 Hz, 3H), 1.78 (s, 3H), 1.75 (d, J=1.5 Hz, 3H), 1.45 (s, 9H), 1.43 (s, 9H)

FABMS m/z 826 (M+H)$^+$ calcd for $C_{37}H_{51}N_3O_{12}S_3$=825

Reference Example 7

Synthesis of Compound G

In dichloromethane (53 mL) were dissolved L—Glu (OCH$_2$Ph)—OMe.HCl (5.08 g, 17.4 mmol) and 2,3:4,6-di-O-isopropylidene-2-keto-L-gulonic acid monohydrate (5.00 g, 17.1 mmol). Thereto were added triethylamine (2.42 mL) and DCC (dicyclohexylcarbodiimide; 8.96 g, 43.4 mmol). This mixture was stirred at 25° C. for 12 hours. After the ordinary post-treatment, the reaction product was purified by silica gel column chromatography (eluted with n-hexane/ethyl acetate=2/1 to 1/1) to obtain a condensate (6.84 g, yield 78%). All the condensate was dissolved in ethyl acetate (300 mL), and 10% palladium/carbon (containing 50 w % water; 1.19 g) was added thereto. This mixture was stirred in a hydrogen atmosphere at 25° C. for 1.5 hours. The reaction mixture was filtered, and the filtrate was concentrated to obtain carboxylic acid (5.93 g, quantitative). From this carboxylic acid (5.70 g, 13.7 mmol) and chloromethyl chlorosulfonate (2.60 g, 15.8 mmol) was obtained the corresponding chloromethyl ester (3.41 g, yield 54%) through 2.5-hour reaction.

¹H NMR (CDCl₃, 270 MHz) δ ppm; 7.57 (br d, J=8.6 Hz, 1H), 5.72 (d, J=5.9 Hz, 1H), 5.65 (d, J=5.9 Hz, 1H), 4.67 (m, 1H), 4.59 (s, 1H), 4.34 (d, J=2.0 Hz, 1H), 4.18 (m, 1H), 4.14 (d, J=2.0 Hz, 2H), 3.77 (s, 3H), 2.6–1.9 (m, 4H), 1.54 (s, 3H), 1.54 (s, 3H), 1.45 (s, 3H), 1.33 (s, 3H)

To a solution of the chloromethyl ester obtained (2.50 g, 5.37 mmol) and DC107 (250 mg, 0.490 mmol) in acetone (13 ml) were added powdered potassium iodide (830 mg, 5.00 mmol) and potassium carbonate (346 mg, 2.51 mmol). The resultant suspension was stirred at 25° C. for 15 hours. The reaction mixture was subjected to the ordinary post-treatment and then purified by silica gel column chromatography (eluted with chloroform/methanol=100/1 to 50/1) to obtain a crude reaction product (716 mg). This crude product was purified by HPLC for fractionation (ODS column; eluted with acetonitrile/water=50/50) to obtain Compound G (64 mg, yield 14%).

¹H NMR (CDCl₃, 270 MHz) δ ppm; 8.46 (dd, J=11.2, 16.5 Hz, 1H), 7.57 (br d, J=8.3 Hz, 1H), 7.36 (s, 1H), 6.59 (d, J=11.6 Hz, 1H), 6.23 (t, J=11.4 Hz, 1H), 6.18 (d, J=16.2 Hz, 1H), 5.73 (br d, J=9.2 Hz, 1H), 5.54 (br s, 1H), 5.41 (q, J=6.9 Hz, 1H), 5.38 (s, 2H), 4.96 (dd, J=3.8, 8.7 Hz, 1H), 4.62 (m, 1H), 4.57 (s, 1H), 4.32 (br d, J=2.0 Hz, 1H), 4.17 (br d, J=2.0 Hz, 1H), 4.12 (br s, 2H), 3.89 (d, J=17.8 Hz, 1H), 3.79 (d, J=3.8 Hz, 1H), 3.74 (s, 3H), 2.5–1.4 (m, 8H), 2.28 (d, J=17.8 Hz, 1H), 2.02 (d, J=6.9 Hz, 3H), 1.77 (s, 3H), 1.76 (d, J=1.0 Hz, 3H), 1.53 (s, 3H), 1.52 (s, 3H), 1.43 (s, 3H), 1.31 (s, 3H)

FABMS m/z 940 (M+H)⁺ calcd for $C_{41}H_{53}N_3O_{16}S_3$=939

Reference Example 8

Synthesis of Compound H

In the same manner as in Reference Example 7, a condensate (7.14 g, yield 88%) was obtained from L—Glu (OCH₂Ph)—OMe.HCl (5.76 g, 20.0 mmol), 2,2-bis (hydroxymethyl)propionic acid diisopropylidene acetal (3.48 g, 20.0 mmol), triethylamine (3.07 ml), and DCC (dicyclohexylcarbodiimide; 7.43, 36.0 mmol). All the condensate was dissolved in ethanol (200 ml), and 10% palladium/carbon (containing 50 wt % water; 1.13 g) was added thereto. This mixture was stirred in a hydrogen atmosphere at 25° C. for 3 hours. The reaction mixture was filtered, and the filtrate was concentrated to obtain carboxylic acid (6.26 g, quantitative). From this carboxylic acid (5.24 g, 16.5 mmol) and chloromethyl chlorosulfonate (3.14 g, 19.0 mmol) was obtained the corresponding chloromethyl ester (4.42 g, yield 73%) through 4-hour reaction.

¹H NMR (CDCl₃, 270 MHz) δ ppm; 7.78 (br d, J=7.6 Hz, 1H), 5.72 (d, J=6.1 Hz, 1H), 5.67 (d, J=6.1 Hz, 1H), 4.75 (m, 1H), 4.0–3.7 (m, 4H), 3.77 (s, 3H), 2.6–2.0 (m, 4H), 1.49 (s, 6H), 1.00 (s, 3H)

To a solution of the chloromethyl ester obtained (365 mg, 1.00 mmol) and DC107 (51 mg, 0.10 mmol) in acetone (2.5 ml) were added powdered potassium iodide (166 mg, 1.00 mmol) and potassium carbonate (69 mg, 0.50 mmol). The resultant suspension was stirred at 25° C. for 16.5 hours. The reaction mixture was subjected to the ordinary post-treatment and then purified by thin-layer chromatography (developed with chloroform/methanol=20/1) to obtain Compound H (40 mg, yield 47%).

¹H NMR (CDCl₃, 270 MHz) δ ppm; 8.47 (dd, J=11.2, 16.4 Hz, 1H), 7.74 (br d, J=7.6 Hz, 1H), 7.36(s, 1H), 6.59 (d, J=11.6 Hz, 1H), 6.23 (t, J=11.4 Hz, 1H), 6.17 (d, J=16.4 Hz, 1H), 5.72 (d, J=8.6 Hz, 1H), 5.58 (br s, 1H), 5.42 (q, J=6.9 Hz, 1H), 5.39 (s, 2H), 4.95 (br d, J=8.6 Hz, 1H), 4.71 (m, 1H), 4.0–3.7 (m, 6H), 3.75 (s, 3H), 2.5–1.6 (m, 9H), 2.02 (d, J=6.9 Hz, 3H), 1.75 (s, 6H), 1.47 (s, 6H), 0.98 (s, 3H)

FABMS m/z 840 (M+H)⁺ calcd for $C_{37}H_{49}N_3O_{13}S_3$=839

Reference Example 9

Synthesis of Compound I

In the same manner as in Reference Example 7, a condensate (3.59 g, yield 51%) was obtained from benzyl 4-aminobutyrate hydrochloride (4.65 g, 20.2 mmol), 2,2-bis (hydroxymethyl)propionic acid diisopropylidene acetal (3.52 g, 20.2 mmol), DCC (7.51 g, 36.4 mmol), and triethylamine (3.1 ml). All the condensate was dissolved in ethanol (200 ml), and 10% palladium/carbon (containing 50 wt % water; 1.13 g) was added thereto. This mixture was stirred in a hydrogen atmosphere at 25° C. for 4 hours. The reaction mixture was filtered, and the filtrate was concentrated to obtain the corresponding carboxylic acid (2.67 g, quantitative yield).

From the whole carboxylic acid obtained above and chloromethyl chlorosulfonate (1.96 g, 10.3 mmol) was obtained the corresponding chloromethyl ester (2.05 g, yield 65%) through 5-hour reaction.

¹H NMR (CDCl₃, 270 MHz) δ ppm; 7.18 (br s, 1H), 5.71 (s, 2H), 3.90 (d, J=12.4 Hz, 2H), 3.77 (d, J=12.4 Hz, 2H), 3.38 (m, 2H), 2.49 (t, J=7.4 Hz, 2H), 1.92 (m, 2H), 1.48 (s, 3H), 1.43 (s, 3H), 1.00 (s, 3H)

FABMS m/z 308 (M+H)⁺ calcd for $C_{13}H_{22}{}^{35}ClNO_5$=307

To a solution of the above chloromethyl ester (308 mg, 1.00 mmol) and DC107 (51 mg, 0.10 mmol) in acetone (2.5 ml) were added powdered potassium iodide (166 mg, 1.00 mmol) and potassium carbonate (69 mg, 0.50 mmol). The resultant suspension was stirred at 25° C. for 17.5 hours. The reaction mixture was subjected to the ordinary post-treatment and then purified by thin-layer chromatography (silica gel; developed with chloroform/methanol=20/1) to obtain Compound I (34 mg, yield 44%).

¹H NMR (CDCl₃, 270 MHz) δ ppm; 8.46 (dd, J=11.6, 16.7 Hz, 1H), 7.36 (s, 1H), 7.17 (m, 1H), 6.59 (d, J=11.9 Hz, 1H), 6.23 (t, J=11.7 Hz, 1H), 6.17 (d, J=16.7 Hz, 1H), 5.71 (br d, J=ca. 10 Hz, 1H), 5.69 (br s, 1H), 5.41 (q, J=6.9 Hz, 1H), 5.40 (s, 2H), 4.94 (br d, J=8.6 Hz, 1H), 4.0–3.8 (2 H, overlapped with other peaks), 3.89 (d, J=12.5 Hz, 2H), 3.74 (d, J=12.5 Hz, 2H), 3.33 (m, 2H), 2.5–1.6 (m, 9H), 2.01 (d, J=6.9 Hz, 3H), 1.76 (d, J=1.3 Hz, 3H), 1.73 (s, 3H), 1.46 (s, 3H), 1.41 (s, 3H), 0.98 (s, 3H)

FABMS m/z 782 (M+H)⁺ calcd for $C_{35}H_{47}N_3O_{11}S_3$=781

Reference Example 10

Synthesis of Compound J 1-(2-Hydroxylethyl)-2-pyrrolidone (3.87 g, 30.0 mmol) was dissolved in dichloromethane (15 ml) and triethylamine (4.2 ml). While this solution was kept being stirred with cooling with ice, a solution of chloromethyl chloroformate (2.8 ml) in dichloromethane (45 ml) was added dropwise thereto over a period of 50 minutes. Subsequently, the reaction mixture was continuously stirred with cooling with ice for 4.5 hours. The salt formed in the resultant reaction mixture was separated by filtration, subsequently subjected to the ordinary post-treatment, and then sufficiently dried under vacuum to obtain chloromethyl 2-oxa-4-(2-oxopyrrolidinyl)butyrate (4.46 g, yield 67%).

¹H NMR (CDCl₃, 270 MHz) δ ppm; 5.73 (s, 2H), 4.36 (t, J=5.1 Hz, 2H), 3.60 (t, J=5.1 Hz, 2H), 3.48 (t, J=6.9 Hz, 2H), 2.39 (t, J=8.1 Hz, 2H), 2.05 (m, 2H)

FABMS m/z 222 (M+H)$^+$ calcd for $C_8H_{12}{}^{35}ClNO_4$=221

To a solution of the above chloromethyl 2-oxa-4-(2-oxopyrrolidinyl)butyrate (225 mg, 1.02 mmol) and DC107 (55 mg, 0.11 mmol) in acetone (2.5 ml) were added powdered potassium iodide (166 mg, 1.00 mmol) and potassium carbonate (69 mg, 0.50 mmol). The resultant suspension was stirred at 25° C. for 14 hours. The reaction mixture was subjected to the ordinary post-treatment and then purified by thin-layer chromatography (eluted with chloroform/methanol=20/1) to obtain Compound J (20 mg, yield 27%).

$^1$H NMR (CDCl$_3$, 270 MHz) δ ppm; 8.46 (dd, J=11.2, 16.5 Hz, 1H), 7.35 (s, 1H), 6.59 (d, J=11.9 Hz, 1H), 6.23 (t, J=11.7 Hz, 1H), 6.17 (d, J=16.5 Hz, 1H), 5.93 (br s, 1H), 5.71 (br d, J=8.6 Hz, 1H), 5.47 (d, J=11.2 Hz, 1H), 5.42 (d, J=11.2 Hz, 1H), 5.41 (q, J=6.9 Hz, 1H), 4.95 (d, J=8.9 Hz, 1H), 4.4–4.2 (m, 2H), 3.91 (d, J=17.8 Hz, 1H), 3.7–3.4 (m, 5H), 2.5–1.7 (m, 8H), 2.31 (d, J=17.8 Hz, 1H), 2.01 (d, J=6.6 Hz, 3H), 1.76 (d, s=1.0 Hz, 3H), 1.72 (s, 3H)

FABMS m/z 696 (M+H)$^+$ calcd for $C_{30}H_{37}N_3O_{10}S_3$=695

Reference Example 11

Synthesis of Compound K

Diethylene glycol monomethyl ether (12.0 g, 100 mmol) was dissolved in dichloromethane (50 ml) and triethylamine (15 ml). While this solution was kept being stirred with cooling with ice, a solution of chloromethyl chloroformate (9.25 ml) in dichloromethane (150 ml) was added dropwise thereto over a period of 1.5 hours. Subsequently, the reaction mixture was continuously stirred with cooling with ice for 5 hours. The salt formed in the resultant reaction mixture was separated by filtration, and then subjected successively to washing with saturated aqueous sodium bicarbonate solution, washing with saturated brine, drying with sodium sulfate, and distillation for solvent removal. The residue was sufficiently dried under vacuum to obtain the target compound (18.9 g, 88.9 mmol, 89%) as a colorless, transparent, oily substance.

$^1$H NMR (CDCl$_3$, 270 MHz) δ ppm; 5.74 (s, 2H), 4.38 (m, 2H), 3.75 (m, 2H), 3.66 (m, 2H), 3.38 (s, 3H)

FABMS m/z 213 (M+H)$^+$ calcd for $C_7H_{13}{}^{35}ClO_5$=212

To a solution of the above chloromethyl ester (1.06 g, 5.00 mmol) and DC107 (255 mg, 0.500 mmol) in acetone (13 ml) were added powdered potassium iodide (830 mg, 5.00 mmol) and potassium carbonate (345 mg, 2.5 mmol). The resultant suspension was stirred at 25° C. for 16.5 hours. The reaction mixture was subjected to the ordinary post-treatment, and the residue was purified by silica gel chromatography (eluted with chloroform/methanol=100/1 to 50/1) and then by HPLC for fractionation (ODS; eluted with acetonitrile/water=45/55) to obtain Compound K (64 mg, yield 20%).

$^1$H NMR (CDCl$_3$, 270 MHz) δ ppm; 8.49 (dd, J=11.5, 16.7 Hz, 1H), 7.36 (s, 1H), 6.59 (d, J=11.9 Hz, 1H), 6.24 (t, J=11.7 Hz, 1H), 6.17 (d, J=16.7 Hz, 1H), 5.74 (br d, J=ca. 9 Hz, 1H), 5.60 (br s, 1H), 5.44 (s, 2H), 5.42 (q, J=6.9 Hz, 1H), 4.95 (br d, J=ca. 9 Hz, 1H), 4.31 (m, 2H), 3.90 (d, J=17.8 Hz, 1H), 3.82 (br s, 1H), 3.54 (m, 2H), 3.62 (m, 2H), 3.71 (m, 2H), 3.37 (s, 3H), 2.4–1.6 (m, 4H), 2.30 (d, J=17.8 Hz, 1H), 2.02 (d, J=6.9 Hz, 3H), 1.77 (s, 3H), 1.75 (d, J=1.3 Hz, 3H)

FABMS m/z 687 (M+H)$^+$ calcd for $C_{29}H_{38}N_2O_{11}S_3$=686

Reference Example 12

Synthesis of Compound L

Water (8.0 ml) and sodium hydroxide (60% oily suspension, 8.0 g) were added to ethylene glycol (22.2 g, 209 mmol), and the mixture was stirred at 130° C. for 30 minutes. Thereto was added 4-methoxybenzyl chloride (7.82 g, 49.9 mmol). This mixture was stirred at 130° C. for 11 hours. The reaction mixture was subjected to the ordinary post-treatment, and the resultant residue was purified by silica gel chromatography (eluted with n-hexane/ethyl acetate=2/1 to 1/1) to obtain the corresponding monoether (5.75 g, yield to 51%).

Sodium hydride (60% oily suspension, 5.3 g) was suspended in THF (50 ml). The above monoether (5.75 g, 25.4 mmol) and a solution of chloroacetic acid (5.00 g, 52.9 mmol) in THF (100 ml) were added to the suspension with stirring and cooling with ice. This mixture was stirred with heating and refluxing for 18 hours. Water was added to the reaction mixture, and the aqueous layer was washed with diethyl ether and acidified with concentrated hydrochloric acid. This aqueous layer was subjected successively to extraction with chloroform, drying with magnesium sulfate, distillation for solvent removal, and drying under vacuum to obtain the corresponding carboxylic acid (6.36 g, yield 88%). From this carboxylic acid (6.36 g, 22.4 mmol) and chloromethyl chlorosulfonate (4.32 g, 22.7 mmol) was obtained the corresponding chloromethyl ester (4.36 g, yield 58%) through 3-hour reaction.

$^1$H NMR (CDCl$_3$, 270 MHz) δ ppm; 7.27 (m, 2H), 6.87 (m, 2H), 5.74 (s, 2H), 4.49 (s, 2H), 424 (s, 2H), 3.80 (s, 3H), 3.8–3.5 (m, 8H)

FABMS m/z 333 (M+H)$^+$ calcd for $C_{15}H_{21}{}^{35}ClO_6$=332

To a solution of the above chloromethyl ester (3.32 g, 10.0 mmol) and DC107 (512 mg, 1.00 mmol) in acetone (25 ml) were added powdered potassium iodide (1.69 g, 10.0 mmol) and potassium carbonate (690 mg, 5.00 mmol). The resultant suspension was stirred at 25° C. for 26.5 hours. The reaction mixture was subjected to the ordinary post-treatment and then purified by silica gel chromatography (eluted with chloroform/methanol=100/1) and by HPLC for fractionation (ODS; eluted with acetonitrile/water=45/55) to obtain Compound L (288 mg, yield 36%).

$^1$H NMR (CDCl$_3$, 270 MHz) δ ppm; 8.46 (dd, J=11.4, 16.3 Hz, 1H), 7.35 (s, 1H), 7.26 (m, 2H), 6.87 (m, 2H), 6.58 (d, J=11.9 Hz, 1H), 6.23 (t, J=11.9 Hz, 1H), 6.17 (d, J=16.3 Hz, 1H), 5.73 (br d, J=8.4 Hz, 1H), 5.53 (br s, 1H), 5.45 (s, 2H), 5.41 (q, J=6.9 Hz, 1H), 4.95 (dd, J=4.0, 8.4 Hz, 1H), 4.48 (s, 2H), 4.15 (s, 2H), 3.88 (d, J=17.8 Hz, 1H), 3.8–3.5 (m, 9H), 3.80 (s, 3H), 2.4–1.6 (m, 4H), 2.26 (d, J=17.8 Hz, 1H), 2.02 (d, J=6.9 Hz, 3H), 1.77 (s, 3H), 1.75 (d, J=1.0 Hz, 3H)

FABMS m/z 807 (M+H)$^+$ calcd for $C_{37}H_{46}N_2O_{12}S_3$=806

While the invention has been described in detail and with reference to specific embodiments thereof, it will be apparent to one skill in the art that various changes and modifications can be made therein without departing from the spirit and scope thereof.

What is claimed is:

1. A compound of formula (I) or a pharmaceutically acceptable salt thereof:

(I)

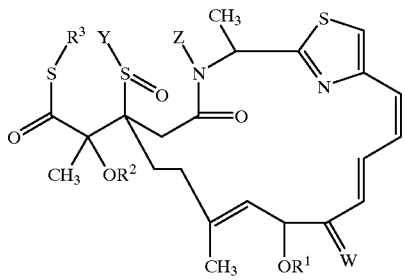

wherein $R^1$ represents: $CO(CR^{4A}R^{4B})_{n1}(O(CH_2)_{p1})_{n2}OR^5$ {wherein n1 represents an integer of 1 or 2; $R^{4A}$ and $R^{4B}$ independently represent hydrogen or lower alkyl; p1 represents an integer of 1 to 10; n2 represents an integer of 1 to 10; and $R^5$ represents hydrogen, lower alkyl, $-SiQ^1Q^2Q^3$ (wherein $Q^1$, $Q^2$, and $Q^3$ independently represent lower alkyl or aryl), or $CO(CR^{5A}R^{5B})_{m1}(O(CH_2)_{p2})_{m2}OR^{5C}$ (wherein m1 represents an integer of 1 or 2; $R^{5A}$ and $R^{5B}$ independently represent hydrogen or lower alkyl; p2 represents an integer of 1 to 10; m2 represents an integer of 1 to 10; and $R^{5C}$ represents lower alkyl)}; or

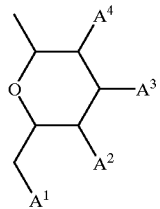

{wherein $A^1$, $A^2$, $A^3$, and $A^4$ independently represent hydrogen, hydroxy, lower alkanoyloxy, substituted or unsubstituted aralkyloxy, or $-OSiA^5A^6A^7$ (wherein $A^5$, $A^6$, and $A^7$ independently represent lower alkyl), or $A^3$ and $A^4$ may be combined with each other to represent a bond};

$R^2$ represents: hydrogen; or $COR^6$ (wherein $R^6$ represents lower alkyl, aralkyl, substituted or unsubstituted aryl, a substituted or unsubstituted heterocyclic group, or $-(CR^{6A}R^{6B})_{n3}(O(CH_2)_{p3})_{n4}OR^{6C}$ (wherein n3, p3, and n4 have the same meaning as n1, p1, and n2, respectively; and $R^{6A}$, $R^{6B}$, and $R^{6C}$ have the same meaning as $R^{4A}$, $R^{4B}$ and $R^5$, respectively)}, $R^3$ represents: lower alkyl; lower alkenyl; substituted or unsubstituted aralkyl; lower alkoxyalkyl; aralkyloxyalkyl; substituted or unsubstituted aryloxyalkyl; lower alkoxycarbonylalkyl; lower alkanoyloxyalkyl; alicyclic alkanoyloxyalkyl; $-CH_2OCOR^7$ <wherein $R^7$ represents $-(CH_2)_{n5}R^{7A}$ (wherein n5 represents an integer of 1 to 5; and $R^{7A}$ represents hydroxy, lower alkoxy, substituted or unsubstituted aralkyloxy, lower alkanoyloxy, $-OPO(OH)_2$, $-OSO_3H$, $-OSiR^{7B}_3$ (wherein $R^{7B}$ are independently lower alkyl or aryl), lower alkanoyl, carboxy, lower alkoxycarbonyl, lower alkoxycarbonylamino, aralkyloxycarbonylamino, lower alkoxycarbonyloxy, lower dialkylaminocarbonyloxy, halogen, nitro, maleimido, 2-pyrrolidinon-1-yl, or $-NHCOR^{7C}$ (wherein $R^{7C}$ represents a substituted or unsubstituted lower alkyl, substituted or unsubstituted alicyclic alkyl, substituted or unsubstituted aryl, substituted or unsubstituted aralkyl, a substituted or unsubstituted heterocyclic group,

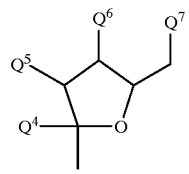

{wherein $Q^4$ to $Q^7$ independently represent hydrogen, hydroxy, lower alkanoyloxy, or $-OSiQ^8_3$ (wherein $Q^8$ has the same meaning as $R^{7B}$), or $Q^4$ and $Q^5$, or $Q^6$ and $Q^7$ are combined with each other to represent $-OC(CH_3)_2O-$}, or

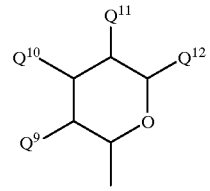

(wherein $Q^9$ to $Q^{12}$ have the same meaning as $Q^4$ to $Q^7$, respectively)>), $-C(CH_3)_2R^{7D}$ {wherein $R^{7D}$ represents lower alkoxycarbonylamino, aralkyloxycarbonylamino, or $-NHCOR^{7E}$ (wherein $R^{7E}$ has the same meaning as $R^{7C}$)} $-(CH_2)_{6n}CHR^{7F}R^{7G}$ (wherein n6 represents an integer of 0 to 3; $R^{7F}$ represents lower alkanoyl, carboxy, lower alkoxycarbonyl, substituted or unsubstituted aryl, substituted or unsubstituted lower alkyl, or substituted or unsubstituted aralkyl; and $R^{7G}$ has the same meaning as $R^{7D}$), substituted alicyclic alkyl, substituted or unsubstituted aryl, substituted or unsubstituted aralkyl, or $-CH_2(OCH_2CH_2)_{n7}OR^{7H}$ (wherein $R^{7H}$ represents hydrogen, lower alkyl, substituted or unsubstituted aryl, or substituted or unsubstituted aralkyl; and n7 represents an integer of 1 to 10)>;

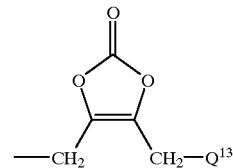

(wherein $Q^{13}$ represents hydrogen, halogen, hydroxy, lower alkoxyalkyl, $-OSiR^{7I}_3$ (wherein $R^{7I}$ has the same meaning as $R^{7B}$), $-OCOQ^{14}$ {wherein $Q^{14}$ represents hydrogen, alkyl, alicyclic alkyl, aralkyl, substituted or unsubstituted aryl, a substituted or unsubstituted heterocyclic group, lower alkoxy, alicyclic alkoxy, 9-fluorenylmethoxy, aralkyloxy, substituted or unsubstituted aryloxy, alkylamino, (hydroxyalkyl) amino, $-(CH_2)_{n8}Q^{14A}$ (wherein n8 represents an integer of 1 to 3, and $Q^{14A}$ represents carboxy, or lower dialkylamino), $CQ^{14B}_2NQ^{14C}COQ^{14D}$ (wherein $Q^{14B}$s are independently hydrogen or lower alkyl, $Q^{14C}$ represents hydrogen or lower alkyl, and $Q^{14D}$ represents lower alkyl, lower alkoxy, aralkoxy, aryl, aryloxy, or 9-fluorenylmethoxy), or —CH$_2$(OCH$_2$CH$_2$)$_{n9}$OCH$_3$ (wherein n9 represents an integer of 1 to 10)}, or

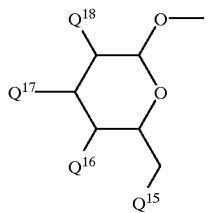

{wherein Q$^{15}$ represents hydrogen, hydroxy, —OSiR$^{7J}{}_3$ (wherein R$^{7J}$ has the same meaning as R$^{7B}$), or lower alkanoyloxy; and Q$^{16}$ to Q$^{18}$ independently represent hydroxy, —OSiR$^{7J}{}_3$, or lower alkanoyloxy, and Q$^{17}$ and Q$^{18}$ may be combined with each other to represent a bond}>;

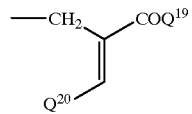

(wherein Q$^{19}$ represents hydroxy, lower alkoxy, or a substituted or unsubstituted heterocyclic group; and Q$^{20}$ represents hydrogen, lower alkyl, or aryl);

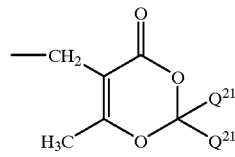

(wherein Q$^{21}$ represents alkyl);

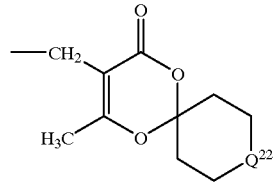

(wherein Q$^{22}$ represents CH$_2$, O, or N—CO$_2$Q$^{23}$ (wherein Q$^{23}$ represents lower alkyl)}; or
phthalimidomethyl, or is combined with Y to represent a bond;
Y is combined together with R$^3$ to represent a bond or is combined together with Z to represent a bond;
Z represents a hydrogen atom, or is combined together with Y to represent a bond; and W represents: oxygen; or NR$^8$ (wherein R$^8$ represents hydroxy, lower alkoxy, lower alkenyloxy, aralkyloxy, substituted or unsubstituted arylsulfonylamino, or lower alkoxycarbonylamino), wherein the substituent on said substituted lower alkyl, substituted alicyclic alkyl, substituted aralkyl, substituted aralkyloxy, substituted aryl, substituted aryloxy, substituted aryloxyalkyl, substituted arylsulfonylamino and substituted heterocyclic group is 1 to 3 substituents independently selected from the group consisting of halogen, nitro, hydroxy, lower alkanoyl, lower alkanoyloxy, lower alkyl, lower alkoxy, aroyl, aroyloxy, lower alkoxycarbonyl, lower alkoxycarbonylamino, lower alkoxycarbonyloxy, lower dialkylcarbamoyloxy, lower alkoxyaralkyloxycarbonyl, —OPO (OH)$_2$, —OSO$_3$H, —OSiR$^{7B}{}_3$ and carboxy.

2. The compound or a pharmaceutically acceptable salt thereof according to claim 1, wherein R$^3$ is combined together with Y to represent a bond; and Z is hydrogen.

3. The compound or a pharmaceutically acceptable salt thereof according to claim 1, wherein Y and Z are combined with each other to represent a bond.

4. The compound or a pharmaceutically acceptable salt thereof according to any one of claims 1–3, wherein R$^1$ is CO(CR$^{4A}$R$^{4B}$)$_{n1}$(O(CH$_2$)$_{p1}$)$_{n2}$OR$^5$.

5. The compound or a pharmaceutically acceptable salt thereof according to claim 4, wherein n2 is 2 or 5.

6. A pharmaceutical composition comprising the compound or a pharmaceutically acceptable salt thereof according to claim 1 and a pharmaceutically acceptable carrier.

7. A method for treating a tumor or a bacterial infection in a patient comprising administering an effective amount of the compound or a pharmaceutically acceptable salt thereof according to claim 1.

8. The compound or a pharmaceutically acceptable salt thereof according to any one of claims 1–3, wherein R$^1$ is CO(CR$^{4A}$R$^{4B}$)$_{n1}$(O(CH$_2$)$_{p1}$)$_{n2}$OR$^5$; or

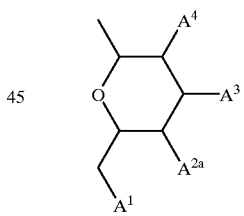

{wherein A$^{2a}$ represents hydroxy, lower alkanoyloxy, substituted or unsubstituted aralkyloxy, or —OSiA$^{5a}$A$^{6a}$A$^{7a}$ (wherein A$^{5a}$, A$^{6a}$, and A$^{7a}$ independently represent lower alkyl)}.

* * * * *

UNITED STATES PATENT AND TRADEMARK OFFICE
CERTIFICATE OF CORRECTION

PATENT NO.    : 6,080,771
DATED         : June 27, 2000
INVENTOR(S)   : Yutaka Kanda et al.

It is certified that error appears in the above-identified patent and that said Letters Patent is hereby corrected as shown below:

Column 3,
Line 26, "respectively )))," should read -- respectively ))), --.

Column 5,
Line 6, "with" should read -- will --;
Line 25, "alkyloxyalkyl," should read -- alkoxyalkyl, --.

Column 15,
Line 41, "$OR_{5b}$" should read -- $OR^{5b}$ --.

Column 18,
Line 12, "diiisopropylethylamine." should read -- diisopropylethylamine. --;
Line 56, "R" should read -- $R^8$ --.

Column 20,
Line 22, "$R_{5c}$" should read -- $R^{5c}$ --;
Line 52, "compounds" (second occurrence) should be deleted.

Column 24,
Line 7, "(e.g.," should read --{e.g., --;
Line 8, "(1989)" should read -- (1989)} --;
Line 15, "chromatography," should read -- chromatographies, --.

Column 25,
Line 25, "14    $COCH_2\ (OCH_2CH_2)_4OCH_3$        DMDO
         15    $COCOH_2\ (OCH_2CH_2)_5OCH_3$       DMDO
         16    $COCH_2\ (OCH_2CH_2)_2OSi(C_2H_5)_2C(CH_3)_3$    DMDO"
(second occurrence) should be deleted.

Column 33,
Line 26, "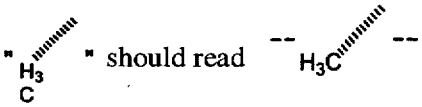" should read -- 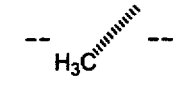 --;

Line 65, "11 OF water." should read -- 1ℓ of water. --.

Column 37,
Line 21, "a400" should read -- α400 --;
Line 36, "with" (first occurrence) should be deleted.

UNITED STATES PATENT AND TRADEMARK OFFICE
CERTIFICATE OF CORRECTION

PATENT NO.   : 6,080,771
DATED        : June 27, 2000
INVENTOR(S)  : Yutaka Kanda et al.

It is certified that error appears in the above-identified patent and that said Letters Patent is hereby corrected as shown below:

Column 38,
Line 19, "1-ethyl- 3-(3" should read -- 1-ethyl-3-(3 --;
Line 26, "(br 5, 1H)" should read -- (br s, 1H) --.

Column 39,
Line 28, "J=1. OHz," should read -- J=1.0 Hz, --;
Line 30, "H51" should read -- $H_{51}$ --.

Column 40,
Line 44, "isomer8.73" should read -- isomer 8.73 --.

Column 41,
Line 8, "(brs," should read -- (br s, --.

Column 43,
Line 24, "H41" should read -- $H_{41}$ --.

Column 45,
Line 8, "857 #" should read -- 857 --.

Column 47,
Line 60, "$O_4$" should read -- $O_{14}$ --.

Column 51,
Line 2, "(br s, 1H-)," should read -- (br s, 1H), --.

Column 56,
Line 21, "(dd,,=16.6," should read -- (dd, J=16.6 --.

Column 57,
Line 38, "3.7.3" should read -- 3.73 --.

Column 61,
Line 31, "at25°C." should read -- at 25°C. --.

Column 62,
Line 56, 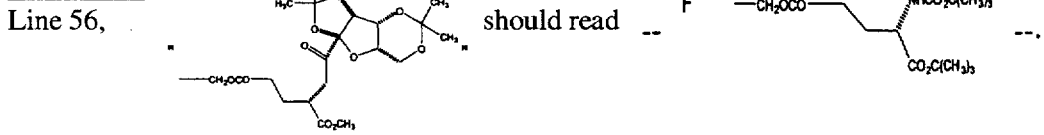

UNITED STATES PATENT AND TRADEMARK OFFICE
CERTIFICATE OF CORRECTION

PATENT NO.  : 6,080,771
DATED       : June 27, 2000
INVENTOR(S) : Yutaka Kanda et al.

It is certified that error appears in the above-identified patent and that said Letters Patent is hereby corrected as shown below:

Column 64,
Line 46, "(br s, 1H)" should read -- (br s, 1H), --;
Line 49, "$O_1O$" should read -- $O_{10}$ --.

Column 66,
Line 50, "OMe.HCl" should read -- OMeHCl --.

Column 67,
Line 36, "OMe.HCl" should read -- OMeHCl --;
Line 64, "7.36(s, 1H)," should read -- 7.36 (s, 1H), --.

Column 68,
Line 54, "was" should be deleted.

Column 69,
Line 25, "was" should read should be deleted.

Column 71,
Line 22, "$R^5C$" should read -- $R^{5c}$ --.

Column 72,
Line 33, "$_{6n}C$" should read -- $_{n6}C$ --.

Signed and Sealed this

Twenty-seventh Day of November, 2001

Attest:

NICHOLAS P. GODICI
Attesting Officer    Acting Director of the United States Patent and Trademark Office